(12) United States Patent
Decaux et al.

(10) Patent No.: US 10,953,237 B2
(45) Date of Patent: Mar. 23, 2021

(54) METHODS OF PROVIDING SKIN CARE USING PHOTOTHERAPY

(71) Applicant: InDerm, Paris (FR)

(72) Inventors: Géraldine Decaux, Paris (FR);
Jean-Alexis Grimaud, Paris (FR)

(73) Assignee: InDerm, Paris (FR)

( * ) Notice: Subject to any disclaimer, the term of this patent is extended or adjusted under 35 U.S.C. 154(b) by 327 days.

(21) Appl. No.: 15/558,774

(22) PCT Filed: Mar. 17, 2016

(86) PCT No.: PCT/EP2016/055873
§ 371 (c)(1),
(2) Date: Sep. 15, 2017

(87) PCT Pub. No.: WO2016/146778
PCT Pub. Date: Sep. 22, 2016

(65) Prior Publication Data
US 2018/0071547 A1    Mar. 15, 2018

(30) Foreign Application Priority Data

Mar. 17, 2015  (EP) ..................................... 15305393
Mar. 19, 2015  (EP) ..................................... 15305404
Apr. 17, 2015  (EP) ................... PCT/EP2015/058457

(51) Int. Cl.
*A61N 5/06*     (2006.01)
*A61Q 19/00*    (2006.01)
(Continued)

(52) U.S. Cl.
CPC ......... *A61N 5/0616* (2013.01); *A45D 34/041* (2013.01); *A61K 8/4913* (2013.01); *A61Q 19/00* (2013.01); *A61Q 19/008* (2013.01); *A61Q 19/08* (2013.01); *A45D 2200/055* (2013.01); *A45D 2200/205* (2013.01); *A61K 2800/81* (2013.01); *A61M 35/003* (2013.01); *A61N 2005/063* (2013.01); *A61N 2005/067* (2013.01); *A61N 2005/0629* (2013.01);
(Continued)

(58) Field of Classification Search
None
See application file for complete search history.

(56) References Cited

U.S. PATENT DOCUMENTS 4,930,504 A * 6/1990 Diamantopoulos .. A61N 5/0616
250/494.1
2003/0004499 A1* 1/2003 McDaniel ............ A61B 18/203
606/3
(Continued)

FOREIGN PATENT DOCUMENTS

CN    103505816 A    1/2014
JP    2005-521432 A  7/2005
(Continued)

*Primary Examiner* — Lynsey C Eiseman
(74) *Attorney, Agent, or Firm* — Banner & Witcoff, Ltd.

(57) ABSTRACT

The present invention relates inter alia to a cosmetic method for providing skin care comprising illuminating the skin of a subject with one or more light beams, said beams together providing light to the skin having a discontinuous spectrum. The invention also relates to a method for treating a skin-related disorder and relates to a light-emitting device for use in these methods.

11 Claims, 25 Drawing Sheets

(51) Int. Cl.
  *A61K 8/49* (2006.01)
  *A61Q 19/08* (2006.01)
  *A45D 34/04* (2006.01)
  *A61N 5/067* (2006.01)
  *A61M 35/00* (2006.01)
(52) U.S. Cl.
  CPC ............. *A61N 2005/0644* (2013.01); *A61N 2005/0652* (2013.01); *A61N 2005/0653* (2013.01); *A61N 2005/0659* (2013.01); *A61N 2005/0663* (2013.01); *A61N 2005/0667* (2013.01)

(56) References Cited

U.S. PATENT DOCUMENTS

| | | |
|---|---|---|
| 2003/0083720 A1 | 5/2003 | Peterson et al. |
| 2004/0191729 A1* | 9/2004 | Altshuler ............ A46B 15/0002 433/215 |
| 2004/0193235 A1 | 9/2004 | Altshuler et al. |
| 2005/0177093 A1* | 8/2005 | Barry ................. A61N 5/0616 604/20 |
| 2006/0129211 A1* | 6/2006 | Canitano ............ A61N 5/0616 607/89 |
| 2006/0178713 A1* | 8/2006 | Maricle .............. A61N 5/0617 607/89 |
| 2006/0217690 A1* | 9/2006 | Bastin ................ A61N 5/0616 606/9 |
| 2006/0241726 A1* | 10/2006 | Whitehurst ......... A61N 5/0616 607/86 |
| 2007/0185553 A1 | 8/2007 | Kennedy |
| 2007/0233209 A1* | 10/2007 | Whitehurst ......... A61N 5/0613 607/93 |
| 2008/0027516 A1 | 1/2008 | Wu et al. |
| 2008/0031833 A1 | 2/2008 | Oblong et al. |
| 2008/0103563 A1* | 5/2008 | Powell ................ A61N 5/0616 607/89 |
| 2009/0132011 A1 | 5/2009 | Altshuler et al. |
| 2009/0270848 A1 | 10/2009 | Weckwerth et al. |
| 2010/0121131 A1* | 5/2010 | Mathes ............... A61H 23/0236 600/14 |
| 2010/0179469 A1* | 7/2010 | Hammond .......... A61N 5/0603 604/20 |
| 2011/0144410 A1* | 6/2011 | Kennedy ............. A61B 18/203 600/2 |
| 2012/0022618 A1* | 1/2012 | Lum ................... A61N 5/0616 607/90 |
| 2012/0271383 A1* | 10/2012 | Ogasawara ......... A61N 5/0617 607/88 |
| 2014/0155961 A1 | 6/2014 | Morariu |
| 2015/0112411 A1* | 4/2015 | Beckman ............ A61M 21/02 607/90 |
| 2015/0127073 A1* | 5/2015 | Thiberg .............. A61N 5/0624 607/90 |
| 2016/0016001 A1* | 1/2016 | Loupis ................ A61N 5/0624 604/20 |
| 2017/0216619 A1* | 8/2017 | Beerwerth .......... A61N 5/0616 |

FOREIGN PATENT DOCUMENTS

| | | |
|---|---|---|
| JP | 2007-203038 A | 8/2007 |
| JP | 2010-259736 A | 11/2010 |
| JP | 2010-284399 A | 12/2010 |
| KR | 2014-0053487 A | 5/2014 |
| WO | 2014/091035 A1 | 6/2014 |

* cited by examiner

|  | Morphology | COL III |
|---|---|---|
| Illumination 2x15s Standard power | - Slight increase in epidermis thickness<br>- Slight increase of the dermis density | +339% |
| Illumination 1x15s Standard power | Slight increase of the dermis density | - |

METHODS OF PROVIDING SKIN CARE USING PHOTOTHERAPY

RELATED APPLICATION DATA

This application is a National Stage Application under 35 U.S.C. 371 of co-pending PCT application number PCT/EP2016/055873 designating the United States and filed Mar. 17, 2016; which is a continuation in part of PCT application number PCT/EP2015/058457 and filed Apr. 17, 2015; which claims the benefit of EP application number 15305404.4 and filed Mar. 19, 2015; and EP application number 15305393.9 and filed Mar. 17, 2015 each of which are hereby incorporated by reference in their entireties.

FIELD OF THE INVENTION

The invention is in the field of cosmetic skin care and medical treatment of skin. In particular, the invention relates to light-emitting devices for illuminating the skin of a subject by phototherapy, and to cosmetic and medical methods for improving the condition of skin of a subject or treating skin disorders by phototherapy, and to methods for improving skin treatment. The invention further relates to compositions for use in such methods.

BACKGROUND OF THE INVENTION

Sunlight was already exploited by ancient cultures to treat skin diseases. This early form of phototherapy, using the sun as light source, was rediscovered in the early 19$^{th}$ century, when it was found that "suntherapy" has a therapeutic effect on the skin disease lupus vulgaris, which is characterized by painful cutaneous tuberculosis skin lesions. As a consequence, phototherapy, or light therapy involving the application and modification of a natural light source is now used as a therapeutic modality to treat a vast array of health conditions and clinical syndromes.

Following the availability of lasers that emit monochromatic and coherent light rays, it was found in the 1960's that a low-power laser could induce hair growth in mice, presumably due to the induction of an intracellular signaling cascade and a resulting cellular photoresponse in skin cells.

The human skin is divided in two layers, epidermis and dermis. The epidermis is a stratified squamous epithelium, acting as a barrier against foreign entities such as infectious agents. The epidermis further regulates the amount of water released from the body into the atmosphere through transepidermal water loss. The epidermis is composed of proliferating basal and differentiated suprabasal keratinocytes. The dermis, a layer of skin between the epidermis (with which it makes up the cutis) and subcutaneous tissues, consists of connective tissue and cushions the body from stress and strain. It is composed of three major types of cells: fibroblasts, macrophages, and adipocytes.

Keratinocytes in the stratum basal, the deepest layer of the epidermis, proliferate through mitosis and the daughter cells move up the strata (layers of the epidermis) changing shape and composition as they undergo multiple stages of cell differentiation to eventually become anucleated. During that process, keratinocytes secrete keratin proteins and lipids which contribute to the formation of an extracellular matrix and provide mechanical strength to the skin. Fibroblasts are cell types that synthesize extracellular matrix such as collagen. Both fibroblasts and keratinocytes play major roles in wound healing and in maintaining the integrity, elasticity and appearance of skin (see FIG. 1), while collagen and elastin are produced. These molecules are known to have a positive effect on wound healing and on increasing the elasticity and appearance of skin. Photoaged skin (e.g. prematurely aged skin resulting from chronic exposure to solar radiation) contains reduced amounts of collagen and contains damaged collagen. Further, photoaged skin contains less fibroblasts or less productive fibroblasts and therefore exhibits diminished contractile and mechanical strength. These characteristics are common for aged skin types, and affect the regenerative capacity of the aged skin after trauma as well as its condition and appearance.

There is a need for additional means and methods for improving the condition and appearance of the aging skin and for means and methods for treating skin of subjects suffering from skin disorders. It is an aim of this invention to provide means and methods for cosmetic and therapeutic skin care based on phototherapy.

SUMMARY OF THE INVENTION

It was now surprisingly found that light of a combination of specific wavelengths in a narrow range has a superior effect on the skin, and can beneficially be used in phototherapy. In particular, it was found that the illumination of skin cells by light having a discontinuous spectrum with peaks in wavelengths corresponding to green light, red light and near infrared light is very beneficial for skin activation processes involving proliferation and migration of skin cells, such as occurring in wound healing, and for production of extracellular matrix fibers such as collagen, especially collagen III. It was also surprisingly found that a specific illumination regimen provides for increased collagen production.

The present invention therefore provides, in a first aspect, a cosmetic (e.g. aesthetic) method for providing skin care, the method comprising illuminating the skin of a subject with one or more light beams, said beams together providing light to the skin having a discontinuous spectrum with peaks in wavelengths corresponding to green light, red light and near infrared light, wherein said skin is illuminated simultaneously or successively with said wavelength peaks.

In a preferred embodiment of a cosmetic method according to the invention, said method further comprises the application, preferably topical application, of a skin care active ingredient prior, during or after the step of illuminating the skin, preferably, said skin care active ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as transretinoic acid, hyaluronic acid, triethanolamine, resveratrol, plant or algae extracts including phytomolecules such as polysaccharides, hydroquinone, mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51), azelaic acid, lactic acid, phytic acid, salicylic acid, trichloro acid, enzymes eg papain, bromelain, dipalmitoyl-hydroxyproline (DPHP) and moisturizers.

In another preferred embodiment of a cosmetic method according to the invention the fluence or power (irradiance) provided to said skin by said illumination is sufficient to induce collagen and/or elastin production by skin cells, and/or to induce activation, proliferation and/or cell migration of keratinocytes, fibroblasts, proto-myofibroblast and/or myofibroblast, preferably in a keratinocyte or fibroblast cell culture.

In another preferred embodiment said one or more light beams are provided by one or more LED light sources.

In still another preferred embodiment, the cosmetic method according to the invention provides skin rejuvenation, moisturization and/or tightening of skin, superficial and deep skin repair, firming and lifting skin, improving eye contour, skin radiance boost; and/or results in prevention, reduction and/or treatment of wrinkles, fine lines, age spots, scars, stretch marks, cellulite, sallow skin, eye puffiness, eye dark circles, chronically- or photodamaged skin, dry skin, hyperpigmented skin, lax skin, skin redness leathery skin, actinic elastosis and baldness.

In yet another aspect, the present invention provides a method for treating a skin-related disorder by phototherapy comprising illuminating the skin of a subject with one or more light beams, said beams together providing light to the skin having a discontinuous spectrum with peaks in wavelengths corresponding to green light, red light and near infrared light, wherein said skin is illuminated simultaneously or successively with said wavelength peaks.

In a preferred embodiment of a treatment method according to the invention, said method further comprises the application, preferably topical application, of a topical pharmaceutical ingredient prior, during or after the step of illuminating the skin, preferably, said topical pharmaceutical ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including fytomolecules such as polysaccharids, hydroquinone, mequinol, kojic acid, salicylic acid, arbutin, vitamin A derived including as example, adapalene, tazarotene, tetrinoin, benzoyl peroxide, isotretinoin, dipalmitoylhydroxyproline (DPHP) and moisturizers.

In another preferred embodiment of a treatment method according to the invention, the fluence or power (irradiance) provided to said skin by said illumination by phototherapy is sufficient to induce collagen and/or elastin production by skin cells, and/or to induce activation, proliferation and/or cell migration of keratinocytes, fibroblasts, proto-myofibroblast and/or myofibroblast, preferably in a keratinocyte or fibroblast cell culture, or, and preferably, in ex vivo integrated skin when compared to a reference skin.

In another preferred embodiment of a treatment method according to the invention said one or more light beams are provided by one or more LED light sources.

In still another preferred embodiment of a treatment method according to the invention, the skin-related disorder is selected from the group formed by acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and leucoplakiform conditions or lichen and lichen planus, cutaneous, mucosal or ungual psoriases, psoriatic rheumatism, cutaneous atopy including eczema, dry skin, inflammation of the skin, red flushes, solar skin erythema, actinic keratosis, skin allergies and allergic or irritant contact dermatitis, atopic dermatitis, rosacea, hyperpigmentation, benign pigmented lesions (lentigines, freckles, brown spots, melasma), aged skin and lupus erythematous.

In another aspect, the present invention provides a skin care active ingredient, preferably DPHP, for use in a method of activating skin processes including collagen induction and wound healing, wherein said skin care active ingredient, preferably DPHP, is topically administered prior to, during and/or after phototherapy comprising illuminating the skin of a subject with one or more light beams, said beams together providing light to the skin having a discontinuous spectrum with peaks in wavelengths corresponding to green light, red light and near infrared light, wherein said skin is illuminated simultaneously or successively with said wavelength peaks.

In yet another aspect, the present invention provides a light-emitting device for illuminating the skin of a subject by phototherapy, the device comprising one or more light sources adapted for emitting a beam of light having a discontinuous spectrum with peaks in wavelengths corresponding to green light, red light and near infrared light; and wherein said one or more light sources are adapted for simultaneously or successively emitting said wavelength peaks in said beam of light so as to illuminate the surface of the skin.

In a preferred embodiment of a light-emitting device according to the invention said separate peaks in wavelengths are emitted by separate light sources, and/or said light sources are adapted for illuminating the surface of the skin at a fluence or power (irradiance) sufficient to induce collagen and/or elastin production in said skin, and/or to induce activation, proliferation and/or cell migration of keratinocytes, fibroblasts, proto-myofibroblast and/or myofibroblasts in said skin, when compared to a reference skin.

In another preferred embodiment of a light-emitting device according to the invention said one or more light sources are provided in the form of LEDs.

In still another preferred embodiment of a light-emitting device according to the invention, the device further comprises a dispenser adapted for topical application of a skin care active ingredient or pharmaceutical ingredient prior, during or after illumination of the skin by said device, preferably, said skin care active ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including phytomolecules such as polysaccharides, hydroquinone, mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51, azelaic acid, lactic acid, phytic acid, salicylic acid, trichloro acid, enzymes e.g. papain, bromelain, dipalmitoylhydroxyproline (DPHP) and moisturizers.

The present invention provides a light-emitting device for illuminating the skin of a subject by phototherapy, the device comprising one or more light sources adapted for emitting one or more beams of light having a discontinuous spectrum with peaks in wavelengths in the range of 510-536 nm, 650-670 nm and 768-792 nm, preferably said peaks having a half-band width between 15 and 35 nm. In more preferred embodiments of this aspect of the invention, said light has a discontinuous spectrum with peaks in wavelengths in the ranges of 510-530 nm, 650-670 nm and 770-790 nm.

In a preferred embodiment of the light-emitting device according to the invention said one or more light sources are adapted for simultaneously or successively emitting said wavelength peaks in said one or more beams of light so as to illuminate the surface of the skin.

In another preferred embodiment of the light-emitting device according to the invention, said one or more light sources are adapted for emitting one or more beams of light having a discontinuous spectrum with peaks in wavelengths at 520 nm, 660 nm, and 780 nm and a half-band width between 15 and 35 nm.

In yet another preferred embodiment of the light-emitting device according to the invention, said one or more light sources are provided in the form of LEDs, preferably a first LED set at emitting light at 520 nm, a second LED set at emitting light at 660 nm and a third LED set at emitting light at 780 nm.

In yet another preferred embodiment of the light-emitting device according to the invention, said device comprises at least three light-sources adapted for emitting one or more beams of light having a discontinuous spectrum with peaks in wavelengths in the range of 510-536 nm, 650-670 nm and 768-792 nm, preferably said peaks having a half-band width between 15 and 35 nm, or comprises at least three light-sources adapted for emitting one or more beams of light consisting of a discontinuous spectrum with peaks in wavelengths in the range of 510-536 nm, 650-670 nm and 768-792 nm, preferably said peaks having a half-band width between 15 and 35 nm.

In yet another preferred embodiment of the light-emitting device according to the invention, said device comprises a single light-source adapted for emitting a combination of peaks in wavelengths in the range of 510-536 nm, 650-670 nm and 768-792 nm simultaneously, preferably said peaks having a half-band width between 15 and 35 nm, optionally by using a series of blocking filters to remove unwanted wavelength ranges, or by using a single light-source that is adapted for changing its emission spectrum between the required combination of three wavelength ranges subsequently.

In a preferred embodiment of the light-emitting device according to the invention, said device further comprises a dispenser adapted for topical application of a skin care active ingredient or pharmaceutical ingredient prior, during or after illumination of the skin by said device, preferably, said skin care active ingredient is selected from antioxidants, carotenoids, flavonoids, polyphenols, estrogen, vitamins, peptides, palmitoyl-lysine-threonine-threonine-lysine-serine, acetyl-glutamate-glutamate-methionine-glutamine-arginine-arginine, the tripeptide copper glycine-histidine-lysine, hydroxy acids, sugar amines, ceramides, metals, minerals, monoethanolamine, diethanolamine, sodium laureth sulfate, retinoids, trans-retinoic acid, hyaluronic acid, triethanolamine, resveratrol, plant extracts, algae extracts, phytomolecules, polysaccharides, hydroquinone, dipalmitoylhydroxyproline (DPHP) and moisturizers.

In another aspect, the present invention provides a skin care active ingredient for use in the prevention, reduction and/or treatment of a skin-related disorder by phototherapy, said use by phototherapy comprises the steps of:
    illuminating the skin of a subject with one or more beams of light having a discontinuous spectrum with peaks in wavelengths in the range of 510-536 nm, 650-670 nm and 768-792 nm, preferably said peaks having a half-band width between 15 and 35 nm, wherein said skin is illuminated simultaneously or successively with said wavelengths, and
    applying said skin care active ingredient to the skin;
wherein said step of illuminating is performed prior to, simultaneous with, or after the step of applying said skin care active ingredient to the skin.

In more preferred embodiments of this aspect of the invention, said light has a discontinuous spectrum with peaks in wavelengths in the ranges of 510-530 nm, 650-670 nm and 770-790 nm.

In a preferred embodiment of the skin care active ingredient for use according to the present invention, said light has a discontinuous spectrum with peaks in wavelengths at 520 nm, 660 nm, and 780 nm and a half-band width between 15 and 35 nm, preferably wherein said light is provided by LED light sources, more preferably by a first LED set at emitting light at 520 nm, a second LED set at emitting light at 660 nm and a third LED set at emitting light at 780 nm.

In another preferred embodiment of the skin care active ingredient for use according to the present invention, said use by phototherapy comprises the use of the light-emitting device according to the present invention.

In yet another preferred embodiment of the skin care active ingredient for use according to the present invention, said skin care active ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including phytomolecules such as polysaccharides, hydroquinone, mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51), azelaic acid, lactic acid, phytic acid, salicylic acid, trichloro acid, enzymes e.g. papain, bromelain, dipalmitoylhydroxyproline (DPHP), lightening ingredients, brightening ingredients, exfoliants, anti-acne drugs and moisturizers.

In another aspect, the present invention provides DPHP for use in a method of treating a skin-related disorder, the DPHP is topically administered prior to, during and/or after phototherapy, wherein said use by phototherapy comprises the steps of:

illuminating the skin of a subject one or more beams of light having a discontinuous spectrum with peaks in wavelengths in the range of 510-536 nm, 650-670 nm and 768-792 nm, preferably said peaks having a half-band width between 15 and 35 nm, wherein said skin is illuminated simultaneously or successively with said wavelengths, and applying said skin care active ingredient to the skin; wherein said step of illuminating is performed prior to, simultaneous with, or after the step of applying said skin care active ingredient to the skin, preferably thereafter. In more preferred embodiments of this aspect of the invention, said light has a discontinuous spectrum with peaks in wavelengths in the ranges of 510-530 nm, 650-670 nm and 770-790 nm.

In a preferred embodiment of the DPHP for use according to the present invention, said light has a discontinuous spectrum with peaks in wavelengths at 520 nm, 660 nm, and 780 nm and a half-band width between 15 and 35 nm, preferably wherein said light is provided by LED light sources, more preferably by a first LED set at emitting light at 520 nm, a second LED set at emitting light at 660 nm and a third LED set at emitting light at 780 nm.

In another preferred embodiment of the DPHP for use according to the present invention, said use by phototherapy comprises the use of the light-emitting device according to the present invention.

In yet another preferred embodiment of the DPHP for use according to any the present invention, the skin-related disorder is selected from the group formed by acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and luecoplakiform conditions or lichen and lichen planus, cutaneous, mucosal or ungual psoriasis, psoriatic rheumatism, cutaneous atopy including eczema, dry skin, inflammation of the skin, red flushes, solar skin erythema, actinic keratosis, skin allergies and allergic or irritant contact dermatitis, atopic dermatitis, rosacea, and lupus erythematosus, benign pigmented lesions, such as solar lentigo, actinic lentigo, freckles, brown spots.

In another aspect, the present invention provides a skin care active composition for use in a method of treating a skin-related disorder, said composition is topically administered prior to, during and/or after phototherapy, wherein said use by phototherapy comprises the steps of:

illuminating the skin of a subject with one or more beams of light having a discontinuous spectrum with peaks in wavelengths in the range of 510-536 nm, 650-670 nm and 768-792 nm, preferably said peaks having a half-band width between 15 and 35 nm, wherein said skin is illuminated simultaneously or successively with said wavelengths, and applying said skin care active composition to the skin; wherein said step of illuminating is performed prior to, simultaneous with, or after the step of applying said skin care active composition to the skin, preferably thereafter. In more preferred embodiments of this aspect of the invention, said light has a discontinuous spectrum with peaks in wavelengths in the ranges of 510-530 nm, 650-670 nm and 770-790 nm.

In another aspect, the present invention provides a cosmetic method for providing skin care by phototherapy comprising illuminating the skin of a subject with light having a discontinuous spectrum with peaks in wavelengths in the range of 510-536 nm, 650-670 nm and 768-792 nm, preferably said peaks having a half-band width between 15 and 35 nm, wherein said skin is illuminated simultaneously or successively with said wavelengths. In more preferred embodiments of this aspect of the invention, said light has a discontinuous spectrum with peaks in wavelengths in the ranges of 510-530 nm, 650-670 nm and 770-790 nm.

In a preferred embodiment of the cosmetic method for providing skin care according to the present invention, said light has a discontinuous spectrum with peaks in wavelengths at 520 nm, 660 nm, and 780 nm and a half-band width between 15 and 35 nm, preferably wherein said light is provided by LED light sources, more preferably by a first LED set at emitting light at 520 nm, a second LED set at emitting light at 660 nm and a third LED set at emitting light at 780 nm.

In another preferred embodiment of the cosmetic method for providing skin care according to the present invention, wherein said phototherapy comprises the use of the light-emitting device according to the present invention.

In a preferred embodiment of the cosmetic method for providing skin care according to the present invention, said method further comprises the application, preferably topical application, of a skin care active ingredient prior, during or after the step of illuminating the skin, preferably, said skin care active ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including phytomolecules such as polysaccharides, hydroquinone, mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51, azelaic acid, lactic acid, phytic acid, salicylic acid, trichloro acid, enzymes e.g. papain, bromelain, dipalmitoyl-hydroxyproline (DPHP), lightening ingredients, brightening ingredients, exfoliants, anti-acne drugs and moisturizers.

In yet another preferred embodiment of the cosmetic method for providing skin care according to the present invention, the fluence or power (irradiance) provided to said skin by said illumination is sufficient to induce collagen and/or elastin production in said skin, and/or to induce activation, proliferation and/or cell migration of keratinocytes, fibroblasts, proto-myofibroblast and/or myofibroblasts in said skin, when compared to a reference skin.

In yet another preferred embodiment of the cosmetic method for providing skin care according to the present invention said method provides skin rejuvenation, moisturization and/or tightening of skin, superficial and deep skin repair, firming, filling, shaping and lifting skin, improving eye contour, skin radiance boost; and/or results in prevention, reduction and/or treatment of wrinkles, fine lines, age spots, scars, stretch marks, cellulite, sallow skin, eye puffiness, eye dark circles, chronically- or photodamaged skin, dry skin, hyperpigmented skin, lax skin, skin redness leathery skin, actinic elastosis and baldness.

In another aspect, the present invention provides a method for treating a skin-related disorder by phototherapy comprising illuminating the skin of a subject with light having a discontinuous spectrum with peaks in wavelengths in the range of 510-536 nm, 650-670 nm and 768-792 nm, preferably said peaks having a half-band width between 15 and 35 nm, wherein said skin is illuminated simultaneously or successively with said wavelengths. In more preferred embodiments of this aspect of the invention, said light has a discontinuous spectrum with peaks in wavelengths in the ranges of 510-530 nm, 650-670 nm and 770-790 nm.

In a preferred embodiment of the method for treating a skin-related disorder by phototherapy according to the present invention, said light has a discontinuous spectrum with peaks in wavelengths at 520 nm, 660 nm, and 780 nm and a half-band width between 15 and 35 nm, preferably wherein said light is provided by LED light sources, more preferably by a first LED set at emitting light at 520 nm, a second LED set at emitting light at 660 nm and a third LED set at emitting light at 780 nm.

In another preferred embodiment of the method for treating a skin-related disorder by phototherapy according to the present invention, said phototherapy comprises the use of the light-emitting device according to the present invention.

In yet another preferred embodiment of the method for treating a skin-related disorder by phototherapy according to the present invention, said method further comprises the application, preferably topical application, of a topical pharmaceutical ingredient prior, during or after the step of illuminating the skin, preferably, said topical pharmaceutical ingredient is selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including phytomolecules such as polysaccharides, hydroquinone, mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51, azelaic acid, lactic acid, phytic acid, salicylic acid, trichloro acid, enzymes e.g. papain, bromelain, dipalmitoyl-hydroxyproline (DPHP), lightening ingredients, brightening ingredients, exfoliants, anti-acne drugs and moisturizers.

In yet another preferred embodiment of the method for treating a skin-related disorder by phototherapy according to the present invention, the fluence or power (irradiance) provided to said skin by said illumination by phototherapy is sufficient to induce collagen and/or elastin production in said skin, and/or to induce activation, proliferation and/or cell migration of keratinocytes, fibroblasts, proto-myofibroblast and/or myofibroblasts in said skin, when compared to a reference skin.

In yet another preferred embodiment of the method for treating a skin-related disorder by phototherapy according to the present invention, the skin-related disorder is selected from the group formed by acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and leukoplakiform conditions or lichen and lichen planus, cutaneous, mucosal or ungual psoriases, psoriatic rheumatism, cutaneous atopy including eczema, dry skin, inflammation of the skin, inflammation of the skin after dermatology and or aesthetic procedure, inflammation of the skin due to radiotherapy exposure, sensitive skin, red flushes, solar skin erythema, actinic keratosis, actinic lentigo, solar lentigo, freckles, brown spot, melasma, radiodermitis, skin allergies and allergic or irritant contact dermatitis, atopic dermatitis, rosacea, and lupus erythematous.

DESCRIPTION OF THE DRAWINGS

FIG. 1 exemplifies the interplay between keratinocytes and fibroblasts in skin of a subject. The importance of cross-talk follows from the circumstance that, if either keratinocytes or fibroblasts are not present, or present in reduced amounts, fibroblast differentiation is hampered. As a result, deposition of connective tissue components, such as collagen and elastin, is impaired.

FIG. 6 shows 3-LED and individual LED illumination of keratinocytes, and FIG. 7 shows 3-LED and individual LED illumination of fibroblasts, CTRL in FIGS. 6 and 7 refer to no-illumination. The results clearly show that a different combination of three wavelength ranges, not corresponding to the combination of the present invention, does not advantageously increase wound healing as compared to the control (no illumination). An alternative combination of three wavelengths using a combination of 590 nm, 635 nm and 735 nm LEDS has no photobiomodulatory effect on keratinocytes or fibroblasts. There is a similar experimental wound closure profile when compared to control and when compared to each single wavelength (590 nm or 635 nm or 735 nm separately).

FIG. 8 shows the increase in collagen III in the dermis upon daily illumination with a LED set at emitting light of 520 nm (151 W/m$^2$ or 0.45 J/cm$^2$), 660 nm (224 W/m$^2$ or 0.67 J/cm$^2$) or 780 nm (42 W/m$^2$ or 0.13 J/cm$^2$) at a standard power (irradiance) for 2×15 seconds as compared to illuminating 1×15 seconds. On a 7 days basis the irradiances included 3.2 J/cm$^2$ (520 nm); 4.7 J/cm$^2$ (660 nm); and 0.89 J/cm$^2$ (780 nm) for a total of 8.8 J/cm$^2$ for all 3 LEDs together. Collagen III increased by 339% when illuminating for 2×15 seconds. It is noted that some preferred embodiments in aspects of this invention, ranges of power (irradiance) may include for instance power (irradiance) for the 520 nm emitting LED illumination between 113 and 189 W/m$^2$, between 168 and 280 W/m$^2$ for the 660 nm emitting LED or between 31 and 52 W/m$^2$ for the 780 nm emitting LED.

DETAILED DESCRIPTION OF THE INVENTION

Definitions

Figure 1:
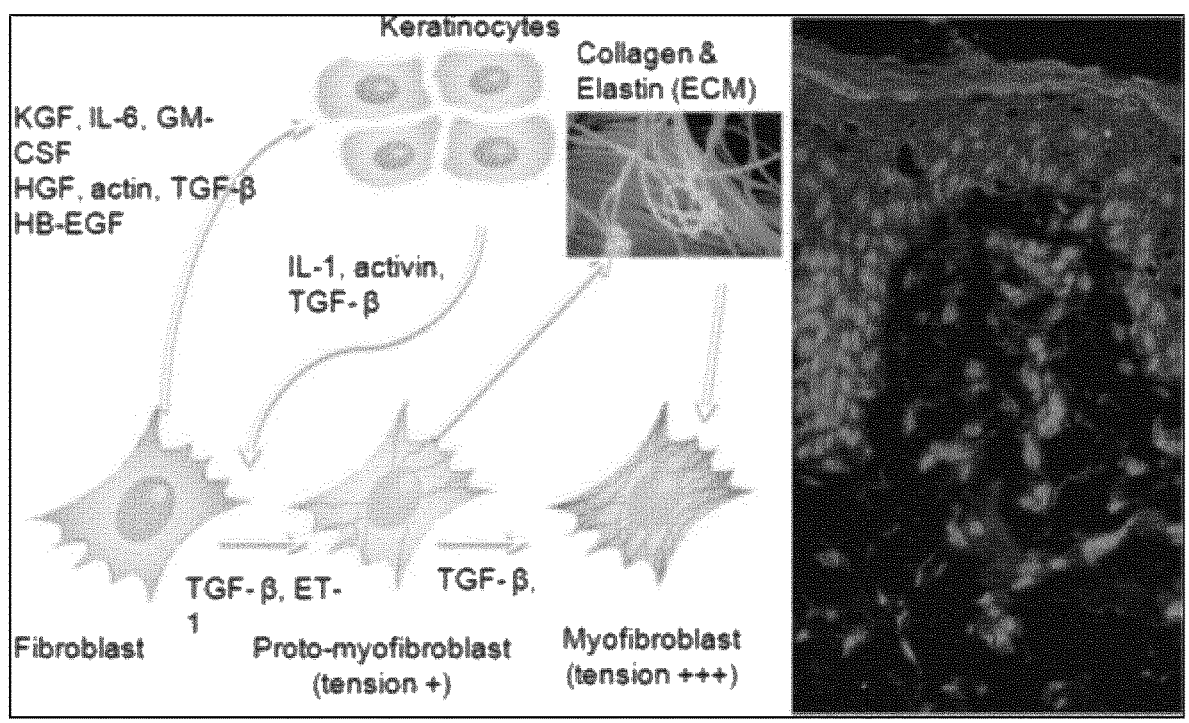
FIG. 1 shows the phenomenon of crosstalk between keratinocytes and fibroblasts.

The term "light", as used herein, refers to electromagnetic radiation of a specific wavelength or a group of wavelengths. In the context of the invention, the term "light" refers in particular to visible light and infrared, preferably near infrared, light.

In the context of the invention, the electromagnetic spectrum is referred to herein as including visible light and infrared light. Said spectrum includes visible light such as violet light (380-436 nm), blue light (436-495 nm), green light (495-566 nm), yellow light (566-589 nm), orange light (589-627 nm) and red light (627-780 nm) and (ii) infrared light (78 nm-1000 nm). Infrared light includes near-infrared light (700 nm-3000 nm).

The term "green light", as used herein, refers to light of wavelengths in the range of 495-566 nm. More preferably, the term "green light", as used herein and also referred to as range (i), refers to light of wavelengths in the range of 496-565 nm, 497-564 nm, 498-563 nm, 499-562 nm, 500-561 nm, 501-560 nm, 502-559 nm, 503-558 nm, 504-557 nm, 505-556 nm, 506-555 nm, 507-554 nm, 508-553 nm, 509-552 nm, 510-551 nm, 511-550 nm, 512-549, 512-545 nm, 512-540, 512-538 nm or 512-536 nm. Even more preferably, said light has a peak wavelength in the range of 512-536 nm, most preferably 510-530 nm. In addition, preferably, at least 50%, preferably at least 55%, 60%, 65%, 70%, 75%, 80%, 85%, 90%, 95%, 96%, 97%, 98%, 99% or 100% of light energy emitted by a light-emitting device, preferably a light-source, is within the range of 496-565 nm, 497-564 nm, 498-563 nm, 499-562 nm, 500-561 nm, 501-560 nm, 502-559 nm, 503-558 nm, 504-557 nm, 505-556 nm, 506-555 nm, 507-554 nm, 508-553 nm, 509-552 nm, 510-551 nm, 511-550 nm, 512-549 nm, 512-545 nm, 512-540 nm, 512-538 nm, 510-530 nm, or 512-536 nm. All possible combinations of wavelength ranges and light energy percentages are envisaged and intended to be individualized in this paragraph. The skilled person understands that, in the context of the invention, the larger the wavelength range, the higher the percentage of light energy emitted by a light-emitting device falling in said range.

The term "red light", as used herein, refers to light of wavelengths in the range of 627-780 nm. More preferably, the term "red light", also referred to as range (ii), refers to light of wavelengths in the range of 630-750 nm, 630-740 nm, 630-730 nm, 630-720 nm, 630-710 nm, 630-700 nm, 635-695 nm, 640-690 nm, 645-685 nm, 645-680 nm, 650-675 nm, 652-670 nm, 652-668 nm. Even more preferably, said light has a peak wavelength in the range of 652-668 nm, most preferably 650-670 nm. In addition, preferably, at least 50%, more preferably at least 55%, 60%, 65%, 70%, 75%, 80%, 85%, 90%, 95%, 96%, 97%, 98%, 99% or 100% of light or light energy emitted by a light-emitting device, preferably a light-source, is within the range of 630-750 nm, 630-740 nm, 630-730 nm, 630-720 nm, 630-710 nm, 630-700 nm, 635-695 nm, 640-690 nm, 645-685 nm, 645-680 nm, 650-675 nm, 652-670 nm, 650-670 nm, or 652-668 nm. All possible combinations of wavelength ranges and light energy percentages are envisaged and intended to be individualized in this paragraph. The skilled person understands that, in the context of the invention, the larger the wavelength range, the higher the percentage of light energy emitted by a light-emitting device falling in said range.

The term "near infrared light", as used herein, refers to light of a discontinuous spectrum with a peak in wavelengths in the range of 700 nm-3000 nm. In other words, said term includes reference, but does not relate exclusively, to a combination of parts of the spectra of red and infrared light. Preferably, said near infrared light, also referred to as range (iii), is light of wavelengths in the range of 700-3000 nm. Even more preferred is the situation wherein said term refers to light wavelengths in the range of 710-2000 nm, 710-1500 nm, 710-1000 nm, 720-1000 nm, 725-1000 nm, 730-900 nm, 735-850 nm, 735-830 nm, 735-820 nm, 740-815 nm, 745-815 nm, 750-810 nm, 755-805 nm, 760-800 nm, 765-795 nm, 765-792 nm or 768-788 nm. Even more preferably, said light has a peak wavelength in the range of 768-788 nm, most preferably 770-790 nm. In addition, preferably, at least 50%, more preferably at least 55%, 60%, 65%, 70%, 75%, 80%, 85%, 90%, 95%, 96%, 97%, 98%, 99% or 100% of light or light energy emitted by a light-emitting device or light-source, is within the range of 700-3000 nm, 710-2000 nm, 710-1500 nm, 710-1000 nm, 720-1000 nm, 725-1000 nm, 730-900 nm, 735-850 nm, 735-830 nm, 735-820 nm, 740-815 nm, 745-815 nm, 750-810 nm, 755-805 nm, 760-800 nm, 765-795 nm, 765-792 nm, 770-790 nm or 768-788 nm. All possible combinations of wavelength ranges and light energy percentages are envisaged and intended to be individualized in this paragraph. The skilled person understands that, in the context of the invention, the larger the wavelength range, the higher the percentage of light energy emitted by a light-emitting device falling in said range.

The term "light-emitting device", as used herein, includes reference to an electrically- or electromagnetically-powered apparatus adapted or configured for producing or providing light of any specific wavelength or any group of wavelengths. Unless specified otherwise, a light-emitting device of the invention transmits or transfers said emitted light in a direction away from the device and into the space directly surrounding the device. Said space is preferably air.

The term "light-source", as used herein, includes reference to one or more light-emitting elements or lamps that, upon receiving an electrical or electromagnetical signal and as a consequence thereof, emit light of any specific wavelength or group of wavelengths. Preferred light sources are LEDs (light emitting diodes) or equivalents thereof, although a light source may also be a laser. The "light-source" may continuously emit the light or it may do so in a pulsed mode. The light source used in aspects of this invention is adapted for emitting a beam of light having a discontinuous spectrum with peaks in wavelengths in specific ranges. The term "discontinuous spectrum" as used herein, refers to a light source that does not emit light evenly across the color spectrum, but instead has spikes or peaks at particular wavelengths and emits little or no light at other wavelengths.

The term "half-band width", as used herein, refers to the width (in nm) of a peak of wavelengths at half its height.

The term "range", as used herein, includes end values of the range.

The term "transmission", or "transmitted", as used herein, refers to emitted light of one or more wavelengths illuminating the skin of a subject. The skilled person understands that emitted light can be identical to transmitted light if optical filters are not present. If optical filters are present, the wavelength composition of transmitted light is different from that of emitted light. In the context of the present invention, unless specified otherwise, the light that is emitted is also the light illuminating skin.

The term "photobiomodulation", as used herein, refers to the use of light for stimulating cells present in skin to initiate light-altered signaling pathways, preferably via an endogenous photoreceptor, thereby providing a physiological effect in skin. For example, photobiomodulation results in the increased proliferation and/or migration of keratinocytes, and to an increase in the production of extracellular matrix proteins such as type I and/or as type III collagen and elastin by fibroblasts.

The term "subject", as used herein, refers to an animal, preferably a mammal, most preferably a human. In particular, the term "subject" relates to a mammal or human in need of a cosmetic method according to the invention or a method for treating a skin-related disorder according to the invention. The skilled person will appreciate that the illumination method as presently revealed and as described in the context of the invention, can be applied for cosmetic purposes (i.e. non-therapeutic purposes) and therapeutic purposes, the latter of which are related to treating or preventing a disease or disorder. When reference is made to the term phototherapy, as used herein, no specific limitation to either a cosmetic or medical method is intended. In aspects of this invention, the subject may be a mammal, and is preferably a human. If the skin is hairy, it is preferably treated in such a way that light can fall on, and penetrate said skin, for example by shaving of hair prior to illumination of skin.

The term "skin" refers to the tissue representing the outer covering of vertebrates on any part of the subject's body, including, but not limited to the skin of the face, neck, chest, skin of the abdomen, back, arms, axilla, hands, buttock, legs, and/or scalp. The term "skin" comprises the epidermal, dermal and/or hypodermal tissue.

The phrase "illuminating skin", or any form thereof as used herein, refers to the application of light on the surface of skin. Preferably, the illumination of skin is effected by a light-emitting device that is located outside the body and emits light penetrating (i) the epidermis, (ii) the epidermis and dermis, or (iii) the epidermis, dermis and hypodermis. The phrasing "wherein said skin is illuminated simultaneously or successively with said wavelengths" refers to the simultaneous or successive illumination with light from any one of the said three wavelengths of green, red and near infrared as defined herein. Preferably, said illumination is simultaneous with light from said three wavelengths.

As used herein, "cosmetic", refers to a beautifying substance or handling which preserves, restores, bestows, simulates, or enhances the appearance of bodily beauty or appears to enhance the beauty or youthfulness, specifically as it relates to the appearance of skin tissue.

As used herein, the term "cosmetically effective amount" means an amount of a skin care active ingredient, composition or illumination by phototherapy sufficient for treating one or more signs of skin aging, but low enough to avoid serious side effects, such as permanent scarring. The cosmetically effective amount of the skin care active ingredient, composition or illumination will vary with the particular condition being treated, the age and physical condition of the subject, the severity of the condition being treated or prevented, the duration of the treatment, the nature of other treatments, the specific skin care active ingredient or product/composition employed, and like factors. Preferably, a cosmetic method according to the invention provides a cosmetic effective amount of illumination and/or skin care active ingredient to the skin of a subject.

As used herein, the term "therapeutically effective amount" means an amount of an skin care active ingredient or pharmaceutical ingredient, composition or illumination by phototherapy sufficient for treating one or more signs of skin damage, but low enough to avoid serious side effects, such as permanent scarring. The therapeutically effective amount of the active agent, preferably skin care active ingredient or pharmaceutical ingredient, composition or illumination will vary with the particular disorder being treated, the age and physical condition of the subject, the severity of the disorder being treated or prevented, the duration of the treatment, the nature of other treatments, the specific compound or product/composition employed, and like factors. Preferably, a method for treatment according to the invention, or DPHP for use according to the invention, provides a therapeutically effective amount of illumination and/or skin care ingredient or pharmaceutical ingredient to the skin of a subject.

In order to achieve a therapeutically or cosmetically effective amount in a method of this invention (which amount may suitably be expressed as power (also referred herein as irradiance) in $W/m^2$), the step of illuminating the surface of the skin is performed at a power (irradiance) sufficient to induce collagen and/or elastin production by skin cells, in particular fibroblasts. In addition thereto, or alternatively, the step of illuminating the surface of the skin is performed at a power (irradiance) sufficient to induce activation, proliferation and/or cell migration of keratinocytes, fibroblasts, proto-myofibroblast and/or myofibroblast. In order to determine if the power (irradiance) is sufficient to induce said production, activation, proliferation and/or cell migration, appropriate tests can be performed in a keratinocyte or fibroblast cell culture, for instance as described in the Examples below.

The term "cosmetic method", as used herein, refers to a method for cosmetic purposes or aesthetic purposes. A cosmetic method of the invention is essentially non-therapeutic and is solely intended to cover handlings that have no medical necessity and do not involve substantial physical intervention on the body in order to maintain the life and health of the subject. A cosmetic method of the invention prevents, reduces, treats and/or removes any skin phenotype characterized in having a reduction, preferably age-related or UV-exposure related, of dermal connective tissue fibers such as collagen and/or elastin, and/or reduction in proto-myofibroblasts and myofibroblasts. In the context of the invention, such skin phenotypes are for example wrinkles, scars or scar formation, cellulite, sallow skin, chronically- or photodamaged skin, dry skin, hyperpigmented skin, lax skin, leathery skin, actinic elastosis and baldness. It is clear that a cosmetic method of the invention fulfills a need of healthy subjects desirous to improve cosmetic and aesthetic appearance.

The (topical) compositions used in aspects of the present invention further preferably comprises a dermatologically acceptable carrier. Herein, the phrase "dermatologically acceptable carrier" means that the carrier is suitable for topical application to the skin, has good aesthetic properties, is compatible with the actives used in aspects of the present invention and any other components, and will not cause any safety or toxicity concerns. The compositions of the present invention comprise from about 50% to about 99.99% of the dermatologically acceptable carrier, alternatively from about 60% to about 99.9% of the carrier, alternatively from about 70% to about 98% of the carrier, and alternatively from about 80% to about 95% of the carrier.

The dermatologically acceptable carrier can be in a wide variety of forms. Non-limiting examples include simple solutions (water-based or oil-based), solid forms (for example, gels or sticks) and emulsions. Herein, "emulsions" generally contain an aqueous phase and a lipid or oil. Lipids and oils may be derived from animals, plants, or petroleum and may be natural or synthetic. Emulsion carriers include, but are not limited to, oil-in-water, water-in-oil, water-in-oil-in-water, and oil-in-water-in-silicone emulsions. In one embodiment, the dermatologically acceptable carrier comprises oil-in-water emulsions and water-in-oil emulsions. In yet another embodiment, the dermatologically acceptable carrier is an oil-in-water emulsion.

The term "skin care", in the context of the invention, refers to the use of phototherapy or combination therapy as indicated herein in order to achieve a cosmetic or therapeutic effect on skin by inducing the production of collagen, and/or elastin, and/or by inducing activation, proliferation and/or cell migration of keratinocytes, fibroblasts, proto-myofibroblast and/or myofibroblast thereby resulting in preventing, reducing, treating and/or removing of one or more of the aforementioned skin phenotypes or skin-related disorder. Preferably, the skin care provides skin rejuvenation, moisturization and/or tightening of skin, deep skin repair, firming and lifting skin, improving eye contour, skin radiance boost; prevention, and/or reduction and/or treatment of wrinkles, fine lines, age spots, scars, stretch marks, cellulite, sallow skin, eye puffiness, eye dark circles, chronically- or photodamaged skin, dry skin, hyperpigmented skin, lax skin, skin redness leathery skin, actinic elastosis and baldness.

The term "phototherapy" is used herein as a generic term to refer to any processes in which skin is illuminated with light for therapeutic or cosmetic purposes.

The term "fluence", as used herein, is also commonly referred to as radiant exposure and is a measure for the amount of light energy delivered per unit area skin for a defined amount of time (power (irradiance) in $W/m^2 \times$ time in seconds), expressed in $J/m^2$. In the context of the invention, power (irradiance) is suitably expressed in $W/m^2$. The skilled person readily will understand that power (irradiance) is dependent on the electric current, voltage, and the specific efficacy ratio of the LED or LEDSs. The skilled person readily will understand that fluence is dependent on the electric current, voltage, illumination period, distance between skin and illumination device and unit area illuminated. Power (irradiance) is controlled by adjusting appropriate settings on a light-emitting device, including, for example, voltage. In addition, the distance to the area that is illuminated can be adjusted to control power (irradiance). The power (irradiance) provided to the skin in a cosmetic or therapeutic method according to the invention is preferably sufficient to induce collagen and/or elastin production in said skin, and/or to induce activation, proliferation and/or cell migration of keratinocytes, fibroblasts, proto-myofibroblast and/or myofibroblasts in said skin. Such a power (irradiance) is preferably determined in a keratinocyte or fibroblast cell culture. The distance between a light-emitting device and the skin preferably less than 10 cm, more preferably less than 5 cm, more preferably less than about 3 cm. Most preferably the light-emitting device is in direct contact with the skin such that the area of the skin that is to be treated is directly illuminated. The distance between the skin and a light source of a light-emitting device is preferably less than 30 cm, more preferably less than 20 cm, more preferably less than 10 cm, more preferably less than 5 cm, in some embodiments preferably about 0.05-29 mm from the skin surface, in alternative or embodiments preferably at skin contact. In the context of this invention, the treatments may be expressed in terms of fluence, or in terms of power (irradiance).

The term "illumination period", as used herein, refers to the period that skin is illuminated with light of any wavelength originating from a light-emitting device according to the invention. In a simple situation, when skin is illuminated continuously, without intervals, the illumination period may be calculated as the time lapsed between t=0 (start of illumination) and t=x (end of illumination). In the case of a session of illumination by pulsed light, said period is calculated as the illumination period of one pulse, multiplied by the number of pulses. The skilled person will understand that light from other sources, such as sunlight, is not taken into account for the illumination period. In fact, in methods of this invention, light from other sources than the light-emitting device of this invention, or light of different wavelengths, is preferably blocked from reaching the skin during a phototherapy illumination period according to the invention. The illumination period is preferably 10, 11, 12, 13, 14, 15, 16, 17, 18, 19, 20, 21, 22, 23, 24, 25, 26, 27, 28, 29, 30, 31, 32, 33, 34, 35, 40, 45, 50, 55 or 60 seconds, more preferably 15 seconds. Most preferably, the illumination period is a multitude of illumination periods, such as for example 2 or more times, 3 or more times, 4 or more times a period of 10, 11, 12, 13, 14, 15, 16, 17, 18, 19, 20, 21, 22, 23, 24, 25, 26, 27, 28, 29, 30, 31, 32, 33, 34, 35, 40, 45, 50, 55 or 60 seconds, preferably 2×15 seconds, with an interval of no illumination in-between, i.e. discontinued illumination. Said interval is preferably at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 to 50, 51 to 59 or 60 seconds or at least 2, 3, 4, 5, 6, 7, 8, 9, 10, 11, 12, 13, 14, 15 minutes. In aspects of this invention the illumination period is repeated preferably about 2 or more times, 3 or more times, 4 or more times daily during a period of 10, 11, 12, 13, 14, 15, 16, 17, 18, 19, 20, 21, 22, 23, 24, 25, 26, 27, 28, 29, 30, 31, 32, 33, 34, 35, 40, 45, 50, 55 or 60 seconds, preferably 1-2× daily, preferably 1× daily, for about 10-20 sec, preferably about 2×15 sec. Light provided in a cosmetic or therapeutic method according to the invention is preferably applied between 1 time and 5 times, preferably once or twice a day, for a period of at least three days, preferably at least one week, preferably at least four weeks up to a lifelong period.

The term "collagen", as used herein, refers to any type of collagen that is produced and deposited in any form in skin of a subject. In particular, the term "collagen" refers to mammalian, preferably human, collagen type I and or collagen type III.

The term "elastin", as used herein, refers to any type of elastin that is produced and deposited in any form in skin of a subject. In particular, the term "elastin" refers to mammalian, preferably human, elastin.

The term "fibroblast" refers to the most common cell type of connective tissue in animals, that synthesizes the extracellular matrix, the structural framework (stroma) for animal tissues. Fibroblasts produce inter alia collagens, glycosaminoglycans, hyaluronic acid, reticular and elastic fibers such as elastin. Dermal fibroblasts are cells within the dermis layer of skin which are responsible for generating connective tissue fibers and allow skin to recover from injury, thereby playing an important role in skin activation processes such as wound healing. The term includes reference to proto-myofibroblasts and myofibroblasts. The proto-myofibroblast differentiates into the myofibroblast under influence of inducing factors released inter alia by keratinocytes. The (proto) myofibroblast provides for increased tension in skin as compared to a fibroblast.

The term "keratinocyte" refers to the predominant cell type in the epidermis, the outermost layer of the skin. Keratinocyte proliferation and migration plays an important role in skin activation processes such as wound healing.

The term "reference skin", as used herein, refers to a skin that has not been illuminated, or that has been illuminated with one or more light beams providing light with peaks in wavelengths not corresponding to green light, red light and near infrared light, and wherein induction of collagen and/or elastin production in said skin, and/or induction of activation, proliferation and/or cell migration of keratinocytes, fibroblasts, proto-myofibroblast and/or myofibroblasts does not occur, due to illumination with insufficient photons in said wavelengths corresponding to green light, red light and near infrared light as disclosed herein, or due to illumination with photons in other wavelengths, i.e., not corresponding to green light, red light and near infrared light as disclosed herein. The induction of collagen and/or elastin production in skin can be measured as an increased collagen and/or elastin (respectively) production by fibroblast cells (expressed as the amount of collagen and/or elastin in arbitrary units measured per nucleus) as described in the experimental section herein below. Essentially anti collagen (e.g. anti-procollagen III) and/or anti-elastin antibodies may be used in an enzyme-linked immunoassay (e.g. ELISA), the performance of which is well known in the art (e.g. Giro et al. 1981. Collagen Rel Res 15:108). Such tests may be performed by using an appropriate control antibody. Proliferation and/or cell migration of keratinocytes, fibroblasts, proto-myofibroblast and/or myofibroblasts may be measured by using immunostaining of skin cells in combination video-microscopy or time-lapse photography and subsequent video analysis or image analysis. Wound healing may be measured by similar methods.

The term "wrinkle", as used herein, refers to a sign of aging of the skin associated with a loss of elasticity or structural integrity of the skin tissue, including but not limited to sagging, lax and loose tissue, and resulting in the presence of lines, including fine lines, fine wrinkles, or coarse wrinkles in the skin. Examples of wrinkles include, but are not limited to, lines around the eyes (e.g. "crow's feet"), brow droop, tear troughs, bunny lines, forehead and cheek, frown lines, nasolabial folds, vertical lip lines, Marionette lines around the mouth, and mental crease. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

The term "scar", as used herein, refers to areas of fibrous tissue (fibrosis) that replace normal skin after injury. A scar results from the biological process of wound repair in the skin.

The term "cellulite", as used herein, refers generally to skin, particularly skin of the abdomen, thighs, and/or buttocks that exhibits a padded and orange-peel appearance generally from the protrusion of adipose lobules through unstretchable conjunctive tissue.

The term "hyperpigmentation", as used herein, refers to skin having an increased amount of melanin in the dermis or epidermis which may, for example, result from exposure to sunlight.

The phrase "tightening of skin", as used herein, refers to an increase in firmness of skin and/or a decrease in the amount and/or extent of wrinkles.

The term "cosmetic composition", as used herein refers in particular to cosmetic compositions comprising an active agent that can be topically applied to mammalian keratinous tissue such as human skin.

The term "skin care active ingredient" or "pharmaceutical ingredient", as used interchangeable herein, preferably refers to a compound (e.g., a synthetic compound or a compound isolated from a natural source or a natural extract) that has a cosmetic or therapeutic effect on skin, respectively. The skin care active ingredient or pharmaceutical ingredient that may be provided in a dispenser of the device, or in a (disposable) capsule or cartridge for releasable coupling to the device of the present invention, may in principle be any skin care ingredient. Non-limiting examples are indicated herein above, including mequinol, kojic acid, arbutin, mulberry, blueberry, cranberry, Glycyrrhia Glaba, Glycyrrhizate, Glabridin, pycnogenol, pinus pinaster, phyllanthus emblica, ascophyllum nodosum, aspergillus ferment, ferula foetida, mitracarpus scaber, nasturlium officinale, palmaria plamato, ramex crispus, salvia miltiorrhyiza, saxifrage samentosa, sophira angustifolia, hydroxypropyl tetrahydropyrantriaol, ferulic acid, phloretin, epilobium angustifolium, niacimide, glucosamine, resorcinol, peptides (nanopeptide 1, oligopeptide 68, oligopeptide 34, oligopeptide 51), azelaic acid, lactic acid, phytic acid, salicylic acid, trichloro acid, enzymes e.g. papain, and bromelain. Very suitable examples of skin care active ingredients or pharmaceutical ingredients include antioxidants (including carotenoids, flavonoids and polyphenols), hormones (including estrogen), skin anti-ageing agents such as green tea, skin lightening agents such as bearberry leaves extract and undecylenoyl phenylalanine, vitamins, peptides (including palmitoyl-lysine-threonine-threonine-lysine-serine, acetyl-glutamate-glutamate-methionine-glutamine-arginine-arginine and the tripeptide copper glycine-histidine-lysine), hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including fytomolecules such as polysaccharides, hydroquinone, dipalmitoylhydroxyproline (DPHP) and moisturizers. The skin care active ingredient or pharmaceutical ingredient may comprise occlusives, including but not limited to petrolatum, lanolin, mineral oil, silicones, and zinc oxide; humectants, including but not limited to glycerin, propylene glycol, sorbitol, hexylene glycol, butylene glycol, urea, and alpha hydroxy acids; emollients, including but not limited to plant oils, polyisobutene, squalene, fatty acids, and ceramide; proteins, including but not limited to collagen, keratin, elastin, and protein mixtures (e.g. wheat protein); anti-aging agents, including but not limited to grape seed extract, hydrolyzed collagen, jojoba protein, elastin, gelatin, chondroitin sulphate, oligopeptides, phytic acid, spirulina extract, calcium PCA, ceramides, Zea mays kernel extract, DHEA, pullulan, ferulic acid, hyaluronic acid, genistein, kojic acid dipalmitate, phyllanthus emblica, coenzyme Q10, ectoin, TIMP2, L-ascorbic acid (Vit. C), argireline, dipalmitoyl hydroxyproline (DPHP), allantoin (2,5-dioxo-4-imidazolidinylurea), retinol palmitate (Vit. A), and provitamin B5; anti-acne agents, including but not limited to tretinoin, isotretinoin, adapalene, tazarotene, azelaic acid, clindamycin, erythromycin, tetracycline, benzyl peroxide, salicylic acid, citric acid, and glycolic acid; an UGT enzyme inducer, including but not limited to chrysin (5,7-dihydroxyflavone) and other flavonoids including, techtochrysin, chrysin 5-methylether, galangin, galangin 5-methylether, pinocembrin, pinobanksin, apigenin, fisetin, hesperitin, kaempferol, morin, myrecetin, naringenin, quercetin, quercitin, rutin, etc. as disclosed in detail in WO2005102266. The CTFA Cosmetic Ingredient Handbook, Ninth Edition (2002) describes a wide variety of non limiting cosmetic and pharmaceutical ingredients, commonly used in the skin care industry, which are suitable for use as skin care active ingredient or pharmaceutical ingredient in aspects of the present invention. Non-limiting examples of these ingredient classes include: healing agents, anti-aging agents, anti-wrinkle agents, moisturizers, antibacterial agents, antifongic agents, anti-inflammatory drugs, anti-pruriginous agents, anaesthetic, antiviral agents, keratolytic agents, free radicals scavengers, antiseborrheic, antidandruff agents, anti-acne agents, exfoliant agents, the agents modulating the differentiation, proliferation or pigmentation of the skin and agents accelerating penetration, skin conditioning agents, pharmaceutical drugs, humectants, emollients, antiseptic agents, antimicrobial agents, antioxidants, enzymes, enzymatic inhibitors, enzyme-inducing agents, coenzymes, plant extracts, ceramides, peptides, external analgesics, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents and derivatives (e.g., panthenol and derivatives (e.g., ethyl panthenol), aloe vera, pantothenic acid and its derivatives, bisabolol, and dipotassium glycyrrhizinate), and vitamins and derivatives thereof, and lignans. A preferred skin care active ingredient is DPHP. The skin care active ingredient is preferably selected from the group consisting of skin care active ingredients mentioned in this paragraph. A skin care active ingredient may be useful in the prevention, reduction or treatment of a skin related disorder.

It will be clear to the skilled person that these compounds, depending on their specific use, are pharmaceutical ingredients or skin care active ingredients.

A skin care active ingredient is preferably formulated in a composition for topical application to the skin. Such a composition includes a gel, cream, lotion, shampoo, spray and/or serum. It was unexpectedly found that a skin care active ingredient, for example formulated in a serum and topically applied to skin of a subject, can elicit skin regeneration. This phenomenon is called "biostimulation" or "bioinduction". More specifically, a skin care active ingredient, preferably formulated in a composition for topical application, can heal wounds and induce collagen production. Preferably, application of a skin care active ingredient, preferably formulated in composition for topical application, is combined with the illumination of skin with light in a method according to the invention.

The term "skin-related disorder", as used herein, broadly refers to undesirable skin conditions, including those that are cosmetically, aesthetically, or medically undesirable. The term includes reference to any undesirable condition, preferably (medical) disorder or disease affecting or relating to the skin. Preferably, the skin-related disorder is selected from the group formed by acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and luecoplakiform conditions or lichen and lichen planus, cutaneous, mucosal or ungual psoriasis, psoriatic rheumatism, cutaneous atopy including eczema, dry skin, inflammation of the skin, red flushes, skin erythema, actinic keratosis, skin allergies and allergic or irritant contact dermatitis, atopic dermatitis, rosacea, and lupus erythematous. The skin-related disorder may comprise any one or more of acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and leukoplakiform conditions or lichen and lichen planus, cutaneous, mucosal or ungual psoriasis, psoriatic rheumatism, cutaneous atopy including eczema, dry skin, inflammation of the skin, inflammation of the skin after dermatology and or aesthetic procedure, inflammation of the skin due to radiotherapy exposure, sensitive skin, red flushes, solar skin erythema, actinic keratosis, actinic lentigo, solar lentigo, freckles, brown spot, melasma, radiodermitis, skin allergies and allergic or irritant contact dermatitis, atopic dermatitis, rosacea, lupus erythematosus, aging skin, wrinkles, fine lines, age spots, scars, stretch marks, cellulite, sallow skin, eye puffiness, eye dark circles, chronically- or photodamaged skin, dry skin, hyperpigmented skin, lax skin, skin redness leathery skin, actinic elastosis and baldness, preferably aging skin, wrinkles, fine lines, age spots, scars, stretch marks, cellulite, sallow skin, eye puffiness, eye dark circles, chronically- or photodamaged skin, dry skin, hyperpigmented skin, lax skin, skin redness leathery skin, and actinic elastosis, more preferably aging skin, wrinkles, and fine lines.

The term "skin wounds", as used herein, refers broadly to injuries to the skin and underlying tissues initiated in any one of a variety of ways, for example wounds induced by trauma, cuts, ulcers, burns, and with varying characteristics. The term "skin wounds" encompasses different grades of wounds depending on the depth of the wound, such as wounds extending into the epidermis, dermis and/or hypodermis.

The term "topical" as used herein refers to the application of a composition or active agent directly onto at least a portion or region of the skin.

PREFERRED EMBODIMENTS

Phototherapy

The use of light-emitting diodes (LEDs) in phototherapeutic applications emerged relatively recently. LED phototherapy is considered to be a safe, non-thermal and atraumatic treatment which stimulates cell activity and cell function. In addition to LEDs, laser light sources have been used in phototherapy, preferably a laser that provides low-level laser therapy (LLLT). Both LED phototherapy and LLLT are, in contrast to high-level laser therapy (HLLT), capable of stimulating cell activity in skin tissue, since almost none of the energy of the photon is lost as heat in the tissue but is transferred directly to the absorbing cell, chromophore and/or photoacceptor.

In preferred embodiments of aspects of this invention LEDs are used. The difference between a laser light and LED light is that a LED light emits non-coherent, quasi-monochromatic light rays. This means that a LED, in contrast to a laser, does not emit in-phase light of only one specific wavelength, but rather emits light in a wavelength spectrum or range. For example, a LED set at emitting light of 632 nm may produce 94% of its light output in light having a wavelength between 630 and 634 nm, whereas a corresponding laser only produces in-phase light of a wavelength of 632 nm. It is clear to the skilled person that a LED set at emitting light of a wavelength that is not within the wavelength range as claimed, may well provide part of its light output as light having a wavelength falling within the claimed wavelength range. Next generation LEDs are characterized by a phenomenon called "photon interference" resulting from intersecting beams of LED energy from individual LEDs by which photon intensity is increased dramatically as compared to the older generation of LEDs.

At present, the biochemical mechanism of phototherapy is not precisely understood. It is, however, known that phototherapy can induce an intracellular biochemical reaction, whereby emitted photons are absorbed by photoacceptors or molecular chromophores such as porphyrins, flavins and other light-absorbing moieties within the mitochondria and membranes of skin cells. There is evidence that the effect of phototherapy can be attributed to the activation of mitochondrial respiratory chain components, which result in the initiation of a cascade of cellular reactions, with cytochrome c oxidase playing a central role in absorbing photons and relaying the biochemical signal.

It is further known that fibroblasts and keratinocytes play major roles as effectors and mediators in skin activation processes such as wound healing and in maintaining the integrity, elasticity and appearance of skin (see FIG. 1), while collagen and elastin are produced. These molecules are known to have a positive effect on skin activation processes such as wound healing and increase the elasticity and appearance of skin.

It was surprisingly found that the illumination of keratinocytes and fibroblasts in tissue-cultures with light composed of a specific combination of wavelengths has a positive effect on the proliferation and migration of these cells, that is even more beneficial than illumination with the individual wavelengths, and that this may have important utility in the context of methods for improving skin activation processes such as wound healing or cosmetic methods for improving skin appearance. It was further discovered that light of this combination of wavelengths has a positive effect on collagen production. Higher amounts of collagen are cosmetically beneficial effects as they provide for a tighter, denser and firmer skin.

Methods for determining cell proliferation and cell migration are known in the art and include the use of a cell counter, for example Coulter® counter, and the use of an Essen Woundmaker (Essen Bioscience), whereby the time required to close scratches in confluent cell cultures is determined.

Methods for determining the synthesis of different isotypes of collagen, especially collagen III, by fibroblasts are known in the art and include, for example, immunohistochemistry and image analysis using collagen III-specific antibodies, for example LS-B693 (LifeSpan, Seattle, USA), and quantitative amplification of expression products of collagen.

The present inventors have now surprisingly found that a combination of green, red and near infrared illumination as defined herein provides a very beneficial effect to skin. This is surprising, because the antagonistic effect or synergistic effect of different wavelengths on cells of the skin cannot easily be predicted. For instance, light of a second wavelength may neutralize the beneficial cell activating effect caused by light of a first wavelength.

In addition, it was found that a combination of yellow/orange (590 nm), orange/red (635 nm) and near infrared (735 nm) does not provide the beneficial results obtained when using the combination green (520 nm), red (660 nm), and near infrared (780 nm) according to the invention.

The combination of the this 3-LED combination could also not be matched by the 2-LED combination of green (520 nm) plus red (660 nm), green (520 nm) plus near infrared (780 nm), and red (660 nm) plus near infrared (780 nm). These 2-LED combinations also did not necessarily provided better results than each wavelength alone, as shown in the experimental results below.

Without wishing to be bound by any theory, the present inventors believe they have found a possible mechanisms by which the green (520 nm) wavelength acts on skin. The experimental results provided herein indicate that green (520 nm) wavelengths acts through activation of keratinocytes, and that compounds excreted by these keratinocytes in response to this illumination stimulates or activates skin fibroblasts. Illumination of skin fibroblasts by green (520 nm) wavelengths does itself not result in a response by these fibroblasts. This finding was made by illuminating a keratinocyte cell culture and bringing the isolated keratinocyte supernatant in contact with fibroblasts culture which triggered fibroblasts activation/migration. Direct fibroblasts illumination by 520 nm light did not trigger such an effect.

It was further found that bioinduction of skin, for example by application of DPHP, is synergistically enhanced by photobiomodulation resulting from illuminating the skin of a subject with one or more light beams, said beams together providing light to the skin having a discontinuous spectrum with peaks in wavelengths corresponding to green light, red light and near infrared light, wherein said skin is illuminated simultaneously or successively with said wavelength peaks Light-Emitting Device The present invention provides inter alia to a phototherapeutic device or light-emitting device for illuminating the skin of a subject by phototherapy. The device comprises one or more light sources adapted for emitting a beam of light so as to illuminate the surface of the skin. The light in said beam has a discontinuous spectrum with peaks in wavelengths corresponding to green light, red light and near infrared light. Preferably, the light in said beam has a discontinuous spectrum with peaks in wavelengths in the ranges of (i) 495, 496, 497, 498, 499, 500, 501, 502, 503, 504, 505, 506, 507, 508, 509, 510, 511 or 512 nm, preferably 512 nm, more preferably 510 nm, to 566, 560, 555, 550, 545, 540, 536 nm, preferably 536 nm, more preferably 530 nm; (ii) 630, 635, 640, 645, 645, 650, 652 nm, preferably 652 nm, more preferably 650 nm to 780, 750, 740, 730, 720, 710, 700, 695, 690, 685, 680, 675, 670 or 668 nm, preferably 668 nm, more preferably 670 nm and (iii) 700, 710, 720, 725, 730, 735, 740, 745, 750, 755, 760, 765 or 768 nm, preferably 768 nm, more preferably 770 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm, more preferably 790 nm. All possible combinations of wavelength ranges from (i), (ii) and (iii) mentioned in this paragraph are envisaged and intended to be individualized. Preferably, at least 50%, more preferably at least 55%, 60%, 65%, 70%, 75%, 80%, 85%, 90%, 95%, 96%, 97%, 98%, 99% or 100% of light output or light energy emitted by a light-emitting device according to the invention, is within the range of (i) 495, 496, 497, 498, 499, 500, 501, 502, 503, 504, 505, 506, 507, 508, 509, 510, 511 nm or 512 nm, preferably 512 nm, more preferably 510 nm, to 566, 560, 555, 550, 545, 540, 536 nm, preferably 536 nm, more preferably 530 nm; (ii) 630, 635, 640, 645, 645, 650, 652 nm, preferably 652 nm, more preferably 650 nm, to 780, 750, 740, 730, 720, 710, 700, 695, 690, 685, 680, 675, 670 or 668 nm, preferably 668 nm, more preferably 670 nm, and (iii) 700, 710, 720, 725, 730, 735, 740, 745, 750, 755, 760, 765 or 768 nm, preferably 768 nm, more preferably 770 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm, more preferably 790 nm. All possible combinations of wavelength ranges and light energy percentages are envisaged and intended to be individualized in this paragraph. The wavelength ranges in this aspect, including preferred embodiments thereof as described herein below, are equally applicable to other aspects of this invention.

In certain embodiments of this aspect, the light source(s) may be adapted to emit light of wavelengths consisting essentially of one or more wavelengths in the range of (i) 495, 496, 497, 498, 499, 500, 501, 502, 503, 504, 505, 506, 507, 508, 509, 510, 511 or 512 nm, preferably 512 nm, more preferably 510 nm, to 566, 560, 555, 550, 545, 540, 536 nm, preferably 536 nm, more preferably 530 nm; (ii) one or more wavelengths in the range of 630, 635, 640, 645, 645, 650, 652 nm, preferably 652 nm, more preferably 650 nm, to 780, 750, 740, 730, 720, 710, 700, 695, 690, 685, 680, 675, 670 or 668 nm, preferably 668 nm, more preferably 670 nm and (iii) one or more wavelengths in the range of 700, 710, 720, 725, 730, 735, 740, 745, 750, 755, 760, 765 or 768 nm, preferably 768 nm, more preferably 770 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm, more preferably 790 nm. All possible combinations of wavelength ranges from (i), (ii) and (iii) mentioned in this paragraph are envisaged and intended to be individualized. Preferably, at least 50%, more preferably at least 55%, 60%, 65%, 70%, 75%, 80%, 85%, 90%, 95%, 96%, 97%, 98%, 99% or 100% of light output or light energy emitted by a light-emitting device according to the invention, is within the range of (i) 495, 496, 497, 498, 499, 500, 501, 502, 503, 504, 505, 506, 507, 508, 509, 510, 511 nm or 512 nm, preferably 512 nm, more preferably 510 nm, to 566, 560, 555, 550, 545, 540, 536 nm, preferably 536 nm, more preferably 530 nm; (ii) 630, 635, 640, 645, 645, 650, 652 nm, preferably 652 nm, more preferably 650 nm, to 780, 750, 740, 730, 720, 710, 700, 695, 690, 685, 680, 675, 670 or 668 nm, preferably 668 nm, more preferably 670 nm, and (iii) 700, 710, 720, 725, 730, 735, 740, 745, 750, 755, 760, 765 or 768 nm, preferably 768 nm, more preferably 770 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm, more preferably 790 nm. All possible combinations of wavelength ranges and light energy percentages are envisaged and intended to be individualized in this paragraph.

The light sources in a device of this invention are further adapted for simultaneously or successively emitting the above-referenced wavelength peaks in said beam of light.

A light-emitting device of the invention is preferably an electrically- or electromagnetically-powered apparatus, preferably an electromagnetically-powered apparatus, and may for instance be battery-powered. Further, a light-emitting device according to the invention preferably transmits or transfers emitted light in a direction away from the device and towards the skin.

The light-emitting device may comprise or consist of at least one, more preferably at least three, light-sources adapted for emitting light having wavelength peaks in the ranges as indicated herein above, or may comprise or consist of at least one, more preferably at least three, light-sources adapted for emitting light of wavelengths consisting essentially of one or more wavelengths in the ranges as indicated herein above.

Suitable light-sources, as envisaged herein, include any type of LED (light emitting diode), for example an organic LED (OLED), or an equivalent thereof, or a laser. With an equivalent of a LED is intended any light-source that is adapted for emitting light of equivalent characteristics as light emitted or produced by a LED.

A skilled person will understand that light in aspects of this invention, may be light of one wavelength or a combination of wavelengths in the indicated range, e.g. light consisting essentially of one or more wavelengths in a particular range, such as one or more wavelengths of 512, 513, 514, 515, 516, 517, 518, 519, 520, 521, 522, 523, 524, 525, 526, 527, 527, 528, 529, 530, 531, 532, 533, 534, 535 and/or 536 nm in the range of 512 to 536 nm, or 510, 511, 512, 513, 514, 515, 516, 517, 518, 519, 520, 521, 522, 523, 524, 525, 526, 527, 527, 528, 529, and/or 530 nm in the range of 510 to 530 nm; and one or more wavelengths of 652, 653, 654, 655, 656, 657, 658, 659, 660, 661, 662, 663, 664, 665, 666, 667 668 nm in the range of 652-668 nm, or 650, 651, 652, 653, 654, 655, 656, 657, 658, 659, 660, 661, 662, 663, 664, 665, 666, 667, 668, 669 and/or 670 nm in the range of 650 to 670 nm; and one or more wavelengths of 768, 769, 770, 771, 772, 773, 774, 775, 776, 777, 778, 779, 780, 781, 782, 783, 784, 785, 786, 787 or 788 nm in the range of 768-788 nm, or 770, 771, 772, 773, 774, 775, 776, 777, 778, 779, 780, 781, 782, 783, 784, 785, 786, 787, 788, 789, and/or 790 in the range of 770-790 nm.

Further, in order to provide for the required wavelength peaks in the aforementioned ranges, preferably the ranges of 512 to 536 nm, 652-668 nm and 768 to 788 nm, preferably 510 to 530 nm, 650-670 nm and 770 to 790 nm, the light emitted by the device may consist essentially of one or more wavelengths in the range of 512 to 536 nm, preferably 510 to 530 nm, essentially of one or more wavelengths in the range of 652 nm to 668 nm, preferably 650-670 nm, and essentially of one or more wavelengths in the range of 768 to 788 nm, preferably 770 to 790 nm. It is possible to provide for the appropriate wavelength combination by using a single light-source that is capable of emitting the required combination of the three wavelengths or wavelength ranges simultaneously, optionally by using a series of blocking filters to remove unwanted wavelength ranges, or by using a single light-source that is capable of changing its emission spectrum between the required combination of three wavelengths or wavelength ranges subsequently, whereby, for instance, wavelengths in the individual ranges is provided in a pulsed manner.

The light-source of a light-emitting device according to the invention more preferably comprises at least a first LED set at emitting light at 520 nm, at least a second LED set at emitting light at 660 nm; and at least a third LED set at emitting light at 780 nm. It is thus preferred that a single light-emitting element is set at emitting light of a single wavelength distribution. With wavelength distribution is meant at least one wavelength, or a group of wavelengths. LEDs, do not emit monochromatic light, but quasi-monochromatic light. Such light is not of a single wavelength, but is of a range of wavelengths. Such light can have a wavelength distribution or range that is defined as a certain percentage of emitted light within a wavelength range. The skilled person understands that when a light-emitting device is "set at" emitting light of a certain wavelength, the generated light is in a range of wavelengths, provided that a non-monochromatic light source is used. As defined herein, light of a diode laser is considered monochromatic. The bandwidth of a LED (e.g. having 16 nm FWHM or Full Width Half Max) is not as narrow as that of a diode laser (e.g. for a red diode laser, 1.5 nm FWHM). The LEDs as used in aspects of this invention are preferably narrow bandwidth, or narrow spectrum LEDs (bandwidth 5-50 nm). LEDs can be designed to emit a specific narrow-band wavelength centered around a peak light wavelength, which is the wavelength of highest intensity emitted from the LED. The wavelength that a LED emits is related to the bandgap energy of the semiconductor materials used in its manufacture. An array of LED colors can be readily purchased from the commercial market. The wavelengths as reported in the context of this invention are preferably provided using commercial LEDs (narrow bandwidth). Reported wavelengths of commercial LEDs generally refer to the peak wavelength (wavelength at the maximum spectral band energy) at which the diode is set. The band width is conventionally defined as the full width at half maximum (FWHM) or the width of a spectrum curve measured between those points on the y-axis which are half the maximum amplitude, also known as the half band width (HBW). A narrow bandwidth LEDs comprises a mid spectrum wavelength centered around a specific value, and rapidly falls away in intensity on either side to a full width half maximum (FWHM) wavelength range that extends from 10 nm to 35 nm around a mid spectrum wavelength. In aspects of this invention, the wavelength indicated herein for a LED may refer to the peak wavelength or mid spectrum wavelength.

The half-band width of peaks in wavelengths as produced by a light-emitting device according to the invention, corresponding to green light, red light and near infrared light is preferably between 10 and 50 nm, more preferably between 12 and 38 nm, most preferably between 15 and 35 nm, suitably between 10 and 35 nm. In further preferred embodiments of aspects of this invention, the half-band width of peaks in wavelengths as produced by a light-emitting device according to the invention, or as used in methods of this invention corresponding to green light, red light and near infrared light is preferably between 10 and 25 or between 10 and 35 nm, preferably less, and such narrow values may be attained by higher quality LEDs. Bandwidth may also be expressed as referring to the peak wavelength+/−5-25 nm, in the case of a half-band width between 10 and 50 nm.

Preferably, the light-source of a light-emitting device or as used in aspects of the present invention comprises one or more light sources adapted for emitting a beam of light having a discontinuous spectrum with peaks in wavelengths corresponding to 520 nm+/−5-15 nm, 660 nm+/−5-15 nm; and 780 nm+/−5-15 nm, preferably 520 nm+/−10 nm, 660 nm+/−10 nm; and 780 nm+/−10 nm.

Preferably, the light-source of a light-emitting device or as used in aspects of the present invention comprises at least a first LED set at emitting light at 520 nm+/−5-15 nm, at least a second LED set at emitting light at 660 nm+/−5-15 nm; and at least a third LED set at emitting light at 780 nm+/−5-15 nm, preferably 520 nm+/−10 nm, 660 nm+/−10 nm; and 780 nm+/−10 nm.

LED sources used in aspects of this invention preferably provide light substantially exclusively in a narrow bandwidth, wavelength range of approximately 10 to 30, or 10 to 35, such as 15 to 35 or 15 to 20 nm around the wavelengths of 520 nm, 660 nm and 780 nm as indicated herein.

This light may be emitted simultaneously, for instance by using three separate light sources converging their light into a single beam, or the light may be emitted successively, such that the beam of light changes color during the illumination in accordance with the invention.

Preferably, the light-sources of a light-emitting device according to the invention include, more preferably consist of, at least a first LED set at emitting light at 520 nm; at least a second LED set at emitting light at 660 nm; and at least a third LED set at emitting light at 780 nm, taking into account the half-band width of commercially available LEDs.

A light-emitting device according to the invention (embodiments of which are provided in FIG. 9) further preferably comprises light-direction means adapted or configured for at least partial mixing or bundling of light, and directing said light to at least one area on the skin of a subject that is to be subjected to phototherapy, wherein said mixing or bundling of light at least occurs in the skin of a subject and/or in the light beam prior to said beam illuminating the skin of a subject. More preferably, said light-direction means are an integral part of the light-sources. The light-source can be positioned in a light-emitting device of the invention in such a way that emitted light is forced to converge and thus to at least partially mix or bundle. In FIG. 9, the light-direction means associated with the light-source (9) comprises one or more light guides 113.

The light source(s) is/are preferably adapted for illuminating the surface of the skin at a power (irradiance) sufficient to induce collagen and/or elastin production by skin cells, in particular fibroblasts. In addition thereto, or alternatively, the light sources are preferably adapted for illuminating the surface of the skin at a power (irradiance) sufficient to induce activation, proliferation and/or cell migration of keratinocytes, fibroblasts, proto-myofibroblast and/or myofibroblast, when compared to a reference skin. In order to determine if the power (irradiance) is sufficient to induce said production, activation, proliferation and/or cell migration, appropriate tests can be performed in a keratinocyte or fibroblast cell culture, for instance as described in the examples below.

A light-emitting device according to the present invention is preferably a hand-held device. Preferably, the device comprises a housing for mounting at least one light source, preferably said housing incorporating a handle, a power source for powering the at least one light-source, and a control member for controlling the power to said at least one light source, preferably the device comprises at least one light guide for guiding the light from the at least one light source to an end of the light guide for emitting the light to a surface of the skin.

A light-emitting device according to the present invention preferably further comprises a dispenser or cartridge, releasably coupled to the housing, said dispenser being adapted for topical application of a skin care active ingredient or composition to the surface of skin prior or during illumination of the skin by the device. An embodiment of such a device is detailed in FIG. 9.

The skin care active ingredient or composition that may be provided in a dispenser of the device may in principle be any skin care ingredient. Very suitable examples include antioxidants (including carotenoids, flavonoids and polyphenols), skin anti-ageing agents such as green tea, skin lightening agents such as bearberry leaves extract and undecylenoyl phenylalanine, hormones (including estrogen), vitamins, peptides (including palmitoyl-lysine-threonine-threonine-lysine-serine, acetyl-glutamate-glutamate-methionine-glutamine-arginine-arginine and the tripeptide copper glycine-histidine-lysine), hydroxy acids, sugar amines, ceramides, metals, minerals, monoethanolamine, diethanolamine, sodium laureth sulfate, retinoids such as trans-retinoic acid, hyaluronic acid, triethanolamine, resveratrol, plant or algae extracts including fytomolecules such as polysaccharides, hydroquinone, dipalmitoylhydroxyproline (DPHP), allantoïne (2,5-dioxo-4-imidazolidinylureum) and moisturizers. The skin care active ingredient or composition may comprise occlusives, including but not limited to petrolatum, lanolin, mineral oil, silicones, and zinc oxide; humectants, including but not limited to glycerin, propylene glycol, sorbitol, hexylene glycol, butylene glycol, urea, and alpha hydroxy acids; emollients, including but not limited to plant oils, polyisobutene, squalene, fatty acids, and ceramide; proteins, including but not limited to collagen, keratin, elastin, and protein mixtures (e.g. wheat protein); anti-aging agents, including but not limited to grape seed extract, hydrolyzed collagen, jojoba protein, elastin, gelatin, chondroitin sulphate, oligopeptides, phytic acid, spirulina extract, calcium PCA, ceramides, Zea mays kernel extract, DHEA, pullulan, ferulic acid, hyaluronic acid, genistein, kojic acid dipalmitate, phyllanthus emblica, coenzyme Q10, ectoin, TIMP2, L-ascorbic acid (Vit. C), argireline, dipalmitoyl hydroxyproline (DPHP), retinol palmitate (Vit. A), and provitamin B5; anti-acne agents, including but not limited to tretinoin, isotretinoin, adapalene, tazarotene, azelaic acid, clindamycin, erythromycin, tetracycline, benzyl peroxide, salicylic acid, citric acid, and glycolic acid; an UGT enzyme inducer, including but not limited to chrysin (5,7-dihydroxyflavone) and other flavonoids including, techtochrysin, chrysin 5-methylether, galangin, galangin 5-methylether, pinocembrin, pinobanksin, apigenin, fisetin, hesperitin, kaempferol, morin, myrecetin, naringenin, quercetin, quercitin, rutin, etc. as disclosed in detail in WO2005102266. The CTFA Cosmetic Ingredient Handbook, Ninth Edition (2002) describes a wide variety of nonlimiting cosmetic and pharmaceutical ingredients, commonly used in the skin care industry, which are suitable for use as skin care active ingredient in aspects of the present invention. Non-limiting examples of these skin care active ingredient classes include: healing agents, anti-aging agents, anti-wrinkle agents, moisturizers, antibacterial agents, antifongic agents, anti-inflammatory drugs, anti-pruriginous agents, anesthetic, antiviral agents, keratolytic agents, free radicals scavengers, antiseborrheic, antidandruff agents, anti-acne agents, the agents modulating the differentiation, proliferation or pigmentation of the skin and agents accelerating penetration, skin conditioning agents, pharmaceutical drugs, humectants, emollients, antiseptic agents, antimicrobial agents, antioxidants, enzymes, enzymatic inhibitors, enzyme-inducing agents, coenzymes, plant extracts, ceramides, peptides, external analgesics, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents and derivatives (e.g., panthenol and derivatives (e.g., ethyl panthenol), aloe vera, pantothenic acid and its derivatives, allantoin, bisabolol, and dipotassium glycyrrhizinate), and vitamins and derivatives thereof, lignans and combinations thereof. The skin care active ingredient is preferably selected from the group consisting of skin care active ingredients mentioned in this paragraph.

A light-emitting device according to the invention preferably includes means for setting the illumination period.

A light-emitting device in conformity with the invention will preferably have (i) a power (irradiance) output of between 130-200, or a power (irradiance) output of between 90-150 W/m$^2$, more preferably between 140-150, or 110-133 W/m$^2$, most preferably about 151 or 121 W/m$^2$, for a light source having a discontinuous spectrum with peaks in wavelengths corresponding to green light (range (i)), (ii) a power (irradiance) output of between 100-300 W/m$^2$, more preferably between 215-130 or 160-195 W/m$^2$, most preferably about 224 or 177 W/m$^2$, for a light source having a discontinuous spectrum with peaks in wavelengths corresponding to red light (range (ii)) and (iii) a power (irradiance) output of between 20-60, or 20-50 W/m$^2$, more preferably between 40-50 or 30-40 W/m$^2$, most preferably about 42 or 34 W/m$^2$, for a light source having a discontinuous spectrum with peaks in wavelengths corresponding to near infrared light (range (iii)).

A light-emitting device in conformity with the invention will preferably have (i) a fluence (or radiant exposure) of between 0.05-1 J/cm$^2$, more preferably between 0.1-0.4 J/cm$^2$, most preferably about 0.36 J/cm$^2$, for a light source having a discontinuous spectrum with peaks in wavelengths corresponding to green light (range (i)), (ii) a power fluence (or radiant exposure) of between 0.05-1 J/cm$^2$, more preferably between 0.4-0.7 J/cm$^2$, most preferably about 0.53 J/cm$^2$, for a light source having a discontinuous spectrum with peaks in wavelengths corresponding to red light (range (ii)) and (iii) a fluence (or radiant exposure) of between 0.05-1 J/cm$^2$, more preferably between 0.05-0.2 J/cm$^2$, most preferably about 0.10 J/cm$^2$, for a light source having a discontinuous spectrum with peaks in wavelengths corresponding to near infrared light (range (iii)). The said dosages may be applied in other aspects of this invention. Dosages are daily, but may also be expressed as a dosage (fluence) per week. Suitable fluences as radiant exposure or radiant energy received by a surface per unit area on a weekly basis include 2.5-3.2 J/cm$^2$ for the wavelength range having a peak at 520 nm; 3.7-4.7 J/cm$^2$ for the wavelength range having a peak at 660 nm; and 0.7-1.0 J/cm$^2$ for the wavelength range having a peak at 780 nm. Suitably, the total fluence may range from of 6.9 J/cm$^2$ or 8.8 J/cm$^2$, when using or applying the 3 illumination wavelengths (e.g. 3 LEDs) together.

In the context of aspects according to the invention, the distance between a light-emitting device and the skin is more preferably less than 10 cm, more preferably less than 5 cm, more preferably less than about 3 cm. Most preferably the light-emitting device is in direct contact with the skin such that the area of the skin that is to be treated is directly illuminated. The distance between the skin and a light source of a light-emitting device is preferably less than 30 cm, more preferably less than 20 cm, more preferably less than 10 cm, preferably about 0.05-29 mm from the skin surface, most preferably in direct contact (0 cm).

In the context of aspects according to the invention, the distance between a light-emitting device according to the invention and the skin of a subject is preferably between 5-50 cm, more preferably between 5-20 cm, most preferably about 10 cm. The distance between a light-emitting device and the skin is more preferably less than 10 cm, more preferably less than 5 cm, more preferably less than about 3 cm. Most preferably the light-emitting device is in direct contact with the skin such that the area of the skin that is to be treated is directly illuminated. The distance between the skin and a light source of a light-emitting device is preferably less than 30 cm, more preferably less than 20 cm, more preferably less than 10 cm, more preferably less than 5 cm, more preferably about 0.05-29 mm from the skin surface, preferably in direct contact with the skin (in all aspects herein).

Topical application of a skin care active ingredient or pharmaceutical ingredient on the skin of a subject, and illuminating said skin with one or more light beams can be done separately, but preferably, these steps are performed simultaneously.

Figure 9A:
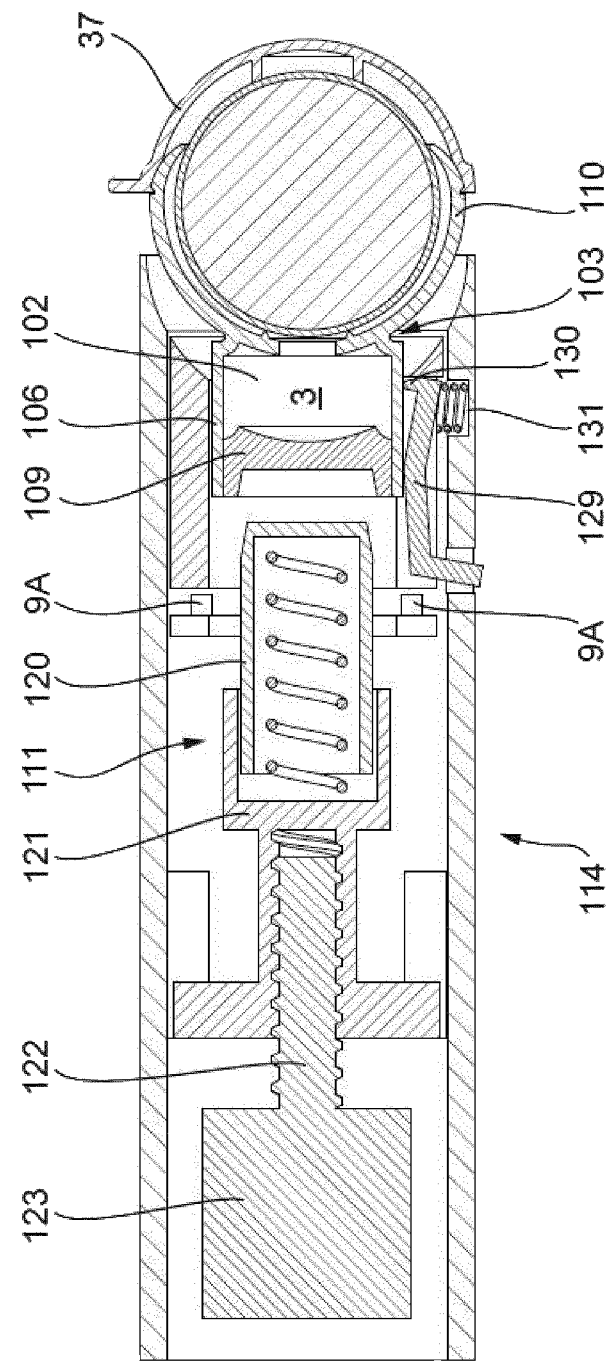
FIG. 9 shows exemplary embodiments of a device according to the present invention (9A-9D). For a detailed description reference is made to other sections in this description. It is to be understood that a device according to the present invention may, in one embodiment, take the form of a device having movable applicator as disclosed in WO2014/091035 and WO2015/193303, the disclosures of which are incorporated herein by reference in their entirety.
Figure 9B:
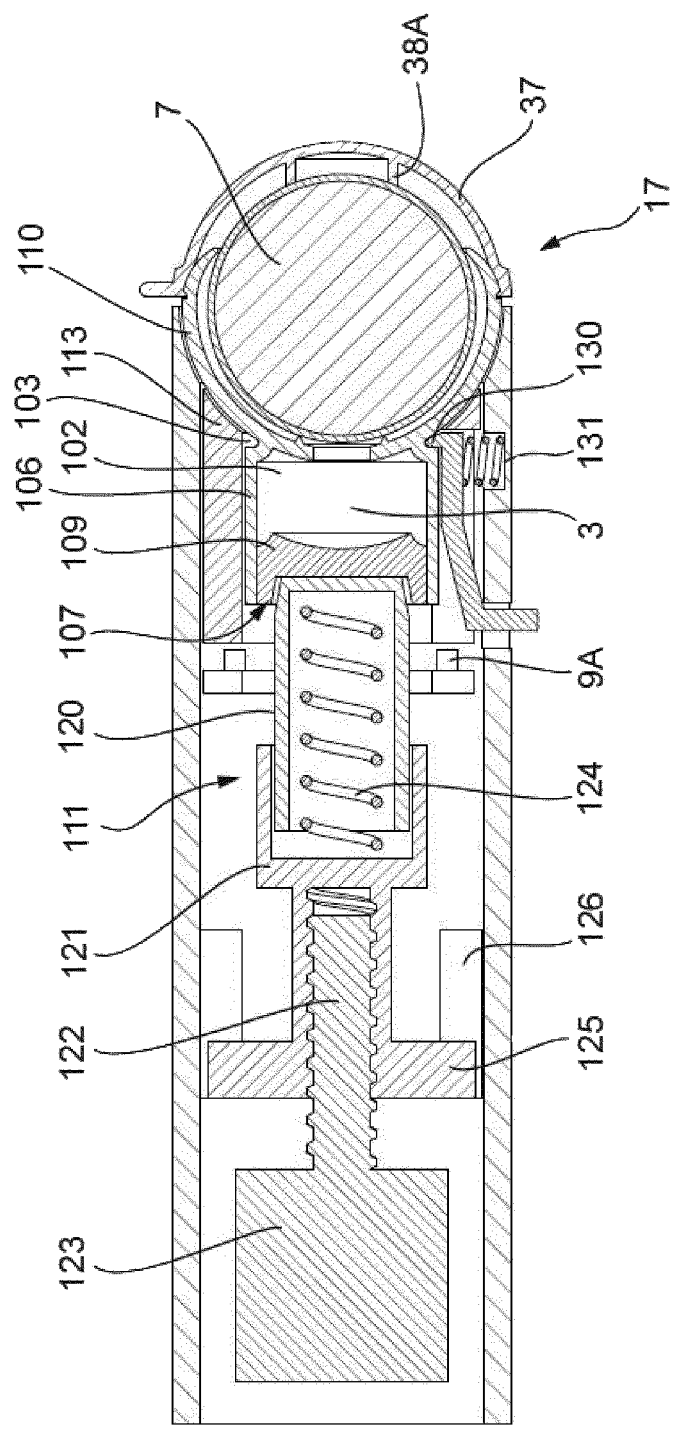

FIGS. 9A and B show an embodiment of a device for both applying such a skin care active ingredient or pharmaceutical ingredient and illuminating the skin.

As illustrated in FIGS. 9A and B, the device, as embodied and referenced as 1 in this figure, for providing skin care using phototherapy can comprise a casing 15 which includes a light-emitting device, and a capsule 17 to apply or distribute a product, such as product 3 to be delivered to the skin. The capsule can be removable from or engaged with the casing 15. It can be pushed (by means of a rod 111 in the casing) or pressed in an axial direction along the axis 13 of the casing 15. A reservoir 102 contains cosmetic product 3 to be delivered to the skin 5. The cosmetic product 3 includes active ingredient or pharmaceutical ingredient. For distributing the product and optimally activating it, the device 1 can comprise an applicator element, or dispenser, 7, such as a ball, and a light source 9 for emitting light rays towards the surface of the skin 5, through or around the element 7. Dispenser 7 is adapted for topical application of a skin care active ingredient or pharmaceutical ingredient included in product 3. Dispenser 7 can especially be a ball rolling freely in a concave housing 110 of the casing 15. A piston 109 pushed axially and forwardly by a motorized spindle 122 pushes the cosmetic product 3 contained in the reservoir 102. One or more openings 108 can be provided for connecting the reservoir 102 with a space 11B around part of the element 7. The light-emitting device includes a light source 9, here shown as a plurality of LED's 9A, for providing the requested light for the phototherapy. One or more light guides 113 can be positioned around the wall of the reservoir, extending between a position close to the light source 9, here shown as a plurality of LED's 9A, and a position closed to or in abutment with the housing 110 of the capsule 17. Thus light from the light source 9, especially the LED's, can be transferred to the capsule 17 by the light guide(s) passed the reservoir 102, unhindered by the product 3 in the reservoir 102.

Figure 9C:
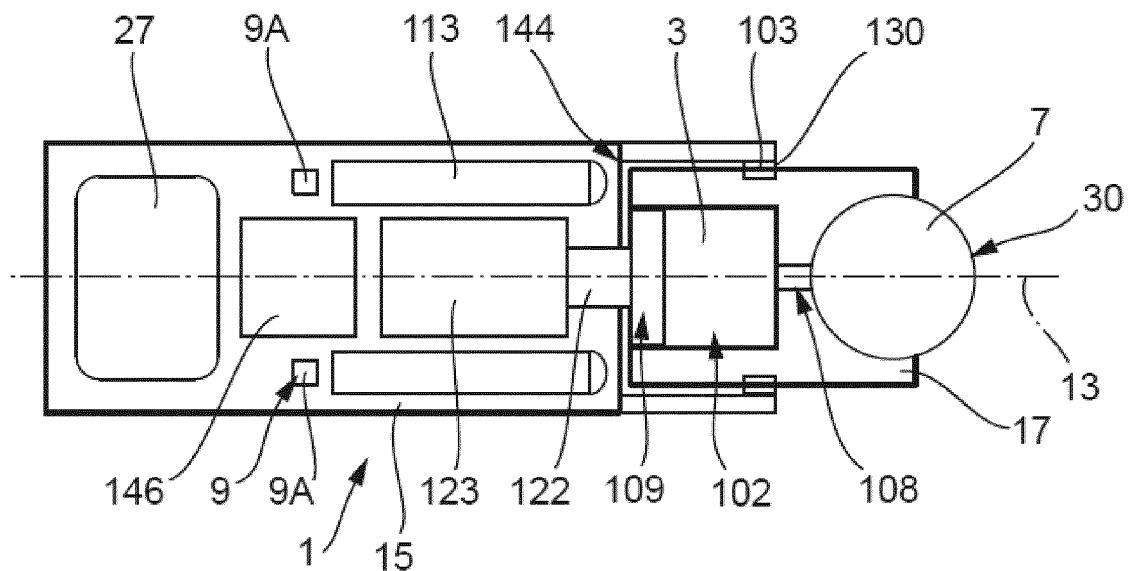
Figure 9D:
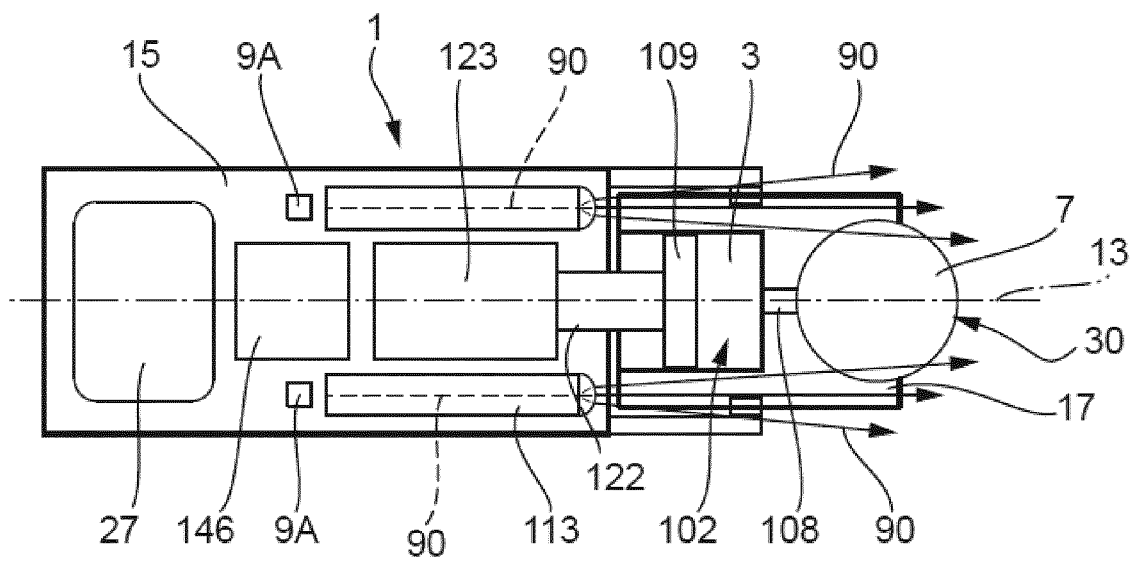

FIGS. 9C and D disclose an embodiment of the present disclosure in which again a cartridge 17 is provided and a housing 15. This embodiment will be described mainly as far as it is different from the previous embodiments. The same or similar parts are indicated with the same or similar reference signs as used in FIG. 1-15. In this embodiment the cartridge 17 is inserted partly into an end of the housing 15, and can be connected thereto releasably in any suitable way, as for example discussed in the previous embodiments. In this embodiment lights 9, such as LED's are provided inside the housing 15, which can radiate light through part of the cartridge 17 towards a surface of skin (not shown). In FIG. 9D light rays 90 are shown schematically, partly passing along side the applicator element 7, here shown as a ball 7 as discussed before. In this embodiment at least part of the light is irradiated on an area around the application zone 30 between the movable element 7 and the surface 5 such as the skin. Part of the light could pass through the applicator element 7 as well, if the element 7 is made transparent for said light. If different light frequencies are used, the applicator element could be made of a plastic material transparent for one or more of these frequencies but not for one or more other frequencies. Thus part of the light can pass through the ball and other another part of the light can only pass alongside the ball. Similarly the cartridge can at least partly be made of a material only transparent for part of the light used, such that a further part cannot pass through that part of the cartridge and for example can only exit the applicator through the applicator element, such as through the ball 7. In this embodiment, as in the previous embodiments, the lights 9, 9A can be positioned directly near an end of the cartridge 17, or can be positioned further into the housing 15, wherein one or more light guides 113 can be provided for transferring the light from the light source 9, 9A to the cartridge 17.

A Cosmetic Method for Providing Skin Care by Using Phototherapy.

The present invention relates further inter alia to a cosmetic method for providing skin care to a subject by using phototherapy, comprising the step of illuminating the skin of a subject with one or more light beams, said beams together providing light to the skin having a discontinuous spectrum with peaks corresponding to green light, red light and near infrared light; wherein said skin is illuminated simultaneously or successively with said wavelength peaks. Preferably, said beams together provide light to the skin having a discontinuous spectrum with peaks in wavelengths in the ranges of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm. All possible combinations of wavelength ranges from (i), (ii) and (iii) mentioned in this paragraph are envisaged and intended to be individualized. Preferably, at least 50%, more preferably at least 55%, 60%, 65%, 70%, 75%, 80%, 85%, 90%, 95%, 96%, 97%, 98%, 99% or 100% of light or light energy emitted by a light-emitting device or light-source, is within the range of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm. All possible combinations of wavelength ranges and light energy percentages are envisaged and intended to be individualized in this paragraph. The wavelength ranges useful in this aspect can be the same as used in other aspects of this invention.

A cosmetic method of the invention may for instance be performed by using a light-emitting device according to the invention as described above. Preferably, in a cosmetic method of the invention, said light-emitting device provides light of wavelengths consisting essentially of one or more wavelengths in the range of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) one or more wavelengths in the range of 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) one or more wavelengths in the range of 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm and illuminates skin of a subject with said light. All possible combinations of wavelength ranges from (i), (ii) and (iii) mentioned in this paragraph are envisaged and intended to be individualized. The wavelength ranges useful in this aspect can be the same as used in other aspects of this invention.

The step of illuminating the skin of a subject may include illumination of the skin with light of a single wavelength, or a combination of wavelengths, in the indicated range, e.g. light consisting essentially of one or more wavelengths in the indicated range, such as one or more wavelengths of 512, 513, 514, 515, 516, 517, 518, 519, 520, 521, 522, 523, 524, 525, 526, 527, 527, 528, 529, 530, 531, 532, 533, 534, 535 or 536 nm in the range of 512 to 536 nm; and one or more wavelengths of 652, 653, 654, 655, 656, 657, 658, 659, 660, 661, 662, 663, 664, 665, 666, 667 or 668 nm in the range of 652-668 nm; and one or more wavelengths of 768, 769, 770, 771, 772, 773, 774, 775, 776, 777, 778, 779, 780, 781, 782, 783, 784, 785, 786, 787 or 788 nm in the range of 768-788 nm. The wavelength ranges useful in this aspect can be the same as used in other aspects of this invention.

Preferably, a cosmetic method according to the invention comprises the step of illuminating skin of a subject with light from a first LED set at emitting light at 520 nm; and light from a second LED set at emitting light at 660 nm; and light from a third LED set at emitting light at 780 nm. The skilled person understands that when a light-emitting device is "set at" emitting light of a certain wavelength, the generated light is in a range of wavelengths, provided that a non-monochromatic light source is used.

Further, in order to illuminate the skin with light having the required wavelength peaks in the aforementioned ranges, the illumination occurs by using light comprising of a discontinuous spectrum of the required combination of the three wavelengths or wavelength ranges simultaneously, optionally by using a series of blocking filters to remove unwanted wavelength ranges from a single light source. Alternatively, the illumination may occur by illuminating the skin with the three wavelengths or wavelength ranges subsequently, one after the other, whereby, for instance, wavelengths in the individual ranges is provided in a pulsed manner.

In embodiments wherein the skin is illuminated successively with said three wavelength peaks, the skin may be illuminated for a first illumination period with light of wavelengths consisting essentially of one or more wavelengths in the aforementioned range (i), preferably 510-536 nm, then, for a second illumination period with light consisting essentially of one or more wavelengths in the aforementioned range (ii), preferably 650-670 nm and then, for a third illuminated period, with one or more wavelengths in the aforementioned range (iii), preferably 770-790 nm.

In fact, the illumination may occur using every possible combination of successive illumination regimes. One example of an alternative successive illumination regime is the situation wherein skin is illuminated for a first illumination period with light of wavelengths consisting essentially of one or more wavelengths in the range of 770-790 nm, then, for a second illumination period with light of one or more wavelengths in the range of 510-536 nm, and then, for a third illuminated period, with one or more wavelengths in the range of 650-670 nm. The wavelength ranges in this aspect can be the same as used in other aspects of this invention.

A most preferred form of illumination of skin in a cosmetic method of the invention is by simultaneous illumination with light having a discontinuous spectrum with peaks in wavelengths in the aforementioned range (i), preferably 510-536 nm, aforementioned range (ii), preferably 650-670 nm, and aforementioned range (iii), preferably 770-790 nm. The wavelength ranges in this aspect can be the same as used in other aspects of this invention.

Preferably, illumination of skin in a cosmetic method of the invention refers to illuminating skin with light having a discontinuous spectrum with peaks in wavelengths in the aforementioned range (i), preferably 510-536 nm, aforementioned range (ii), preferably 650-670 nm, and aforementioned range (iii), preferably 770-790 nm; wherein said peaks are mixed or combined into a single beam prior to illuminating the skin of a subject. Again, the wavelength ranges used in this aspect can be the same as used in other aspects of this invention.

A cosmetic method according to the invention is preferably performed on skin having a phenotype such as wrinkles, scars or scar formation, cellulite, sallow skin, chronically- or photodamaged skin, dry skin, hyperpigmented skin, lax skin, leathery skin, actinic elastosis and baldness.

Illumination of skin in a cosmetic method according to the invention is preferably performed using a power (irradiance) of light at the individual wavelength ranges that results in a cosmetically effective amount of the illumination, e.g. such that collagen and/or elastin is produced in fibroblast. More preferably, illumination of skin in a cosmetic method according to the invention provides to said skin a power (irradiance) of between 130-180 W/m$^2$, preferably between 135-165 W/m$^2$, more preferably about 150-W/m$^2$ for light having the wavelength peak in aforementioned range (i), preferably 512-538 nm; a power (irradiance) of between 150-900 W/cm$^2$, preferably between 180-270 W/cm$^2$, more preferably about 220 W/m$^2$ for light having the required wavelength peak in the aforementioned range (ii), preferably 652-668 nm; and a power (irradiance) of between 20-60 W/m$^2$, preferably between 30-50 W/m$^2$, more preferably about 40 W/m$^2$ for light having the required wavelength peak in aforementioned range (iii), preferably 768-788 nm. The wavelength ranges in this aspect can be the same as used in other aspects of this invention.

More preferably, illumination of skin in a cosmetic method according to the invention provides to said skin a power (irradiance) of between 90-150 W/m$^2$, preferably between 110-133 W/m², more preferably about 121 W/m² for light having the wavelength peak in aforementioned range (i), preferably 510-530 nm; a power (irradiance) of between 150-300 W/cm², preferably between 160-195 W/cm², more preferably about 177 W/m² for light having the required wavelength peak in the aforementioned range (ii), preferably 650-670 nm; and a power (irradiance) of between 20-50 W/m², preferably between 30-40 W/m², more preferably about 34 W/m² for light having the required wavelength peak in aforementioned range (iii), preferably 770-790 nm. The wavelength ranges in this aspect can be the same as used in other aspects of this invention.

Illumination of skin in a cosmetic method according to the invention is preferably performed using a power (irradiance) of light at the individual wavelength ranges that results in a cosmetically effective amount of the illumination, e.g. such that collagen and/or elastin is produced in fibroblast. More preferably, illumination of skin in a cosmetic method according to the invention provides to said skin a power (irradiance) of between 0.05-1 J/cm², preferably between 0.1-0.4 J/cm² more preferably about 0.36 J/cm² for light having the wavelength peak in aforementioned range (i), preferably 512-538 nm; a power (irradiance) of between 0.05-1 J/cm², preferably between 0.4-0.7 J/cm², more preferably about 0.53 J/cm² for light having the required wavelength peak in the aforementioned range (ii), preferably 652-668 nm; and a power (irradiance) of between 0.05-1 J/cm², preferably between 0.05-0.2 J/cm², more preferably about 0.10 J/cm² for light having the required wavelength peak in aforementioned range (iii), preferably 768-788 nm. The wavelength ranges used in this aspect can be the same as used in other aspects of this invention.

A cosmetic method of the invention preferably further comprises the step of administering a cosmetic composition comprising an active agent to said subject, wherein said composition is administered prior to, and/or during and/or after illumination of skin. A cosmetic composition of a cosmetic method of the invention is preferably administered on skin of a subject or accumulates in skin of a subject, more preferably administered on, or accumulated in, that part of skin that is being illuminated, and/or is to be illuminated, and/or was illuminated. Most preferably, a cosmetic composition of a cosmetic method of the invention is preferably applied topically on that part of skin of a subject that is at that moment illuminated, and/or is to be illuminated, and/or was illuminated.

A cosmetic composition of a cosmetic method of the invention preferably comprises an active agent such as carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, trans-retinoic acid, triethanolamine, phytomolecules and moisturizers.

Alternatively, the invention provides a cosmetic method for preventing, reducing, and/or treating, and/or removing any skin phenotype characterized in having a reduction, preferably age-related or UV-exposure related, in dermal connective tissue such as collagen and/or elastin, and/or reduction in proto-myofibroblasts and myofibroblasts. In the context of the invention, such skin phenotypes are for example wrinkles, scars or scar formation, cellulite, sallow skin, chronically- or photodamaged skin, dry skin, hyper-pigmented skin, lax skin, leathery skin, actinic elastosis and baldness.

Method for Treating a Skin-Related Disorder by Using Phototherapy.

The present invention further provides a method for treating a skin-related disorder by using phototherapy, comprising the step of illuminating the skin of a subject with one or more light beams, said beams together providing light to the skin having a discontinuous spectrum with peaks in wavelengths corresponding to green light, red light and near infrared light; wherein said skin is illuminated simultaneously or successively with said wavelength peaks. Preferably, said beams together provide light to the skin having a discontinuous spectrum with peaks in wavelengths in the ranges of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm. All possible combinations of wavelength ranges from (i), (ii) and (iii) mentioned in this paragraph are envisaged and intended to be individualized. Preferably, at least 50%, more preferably at least 55%, 60%, 65%, 70%, 75%, 80%, 85%, 90%, 95%, 96%, 97%, 98%, 99% or 100% of light or light energy emitted by a light-emitting device or light-source, is within the range of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm. All possible combinations of wavelength ranges and light energy percentages are envisaged and intended to be individualized in this paragraph. The wavelength ranges useful in this aspect can be the same as used in other aspects of this invention.

The step of illuminating skin of a subject in a method of treating a skin-related disorder by using phototherapy according to this invention is essentially the same as the step of illumination as described for the cosmetic method above. Hence, these steps are interchangeable between the methods.

A method for treating a skin-related disorder of the invention is preferably performed on skin in need thereof, e.g. skin comprising skin-related disorders such as skin wounds, telangiectasia, atrophy, premalignant skin lesions and inflammatory diseases such as allergic or irritant contact dermatitis, atopic dermatitis, rosacea, inflammatory acne, recalcitrant treatment resistant psoriasis and lupus erythematous.

The present inventors unexpectedly found that light of a specific combination of wavelengths increases the rate of skin activation processes such as wound healing and can therefore be used to treat skin wounds. A method for treating a skin-related disorder of the invention is preferably performed on skin comprising skin wounds. Such a method can alternatively be defined as a method for reducing skin wound area or healing a skin wound area.

Illumination of skin in a method for treating a skin-related disorder according to the invention is preferably performed using a power (irradiance) of light at the individual wavelength ranges that results in a therapeutically effective amount of the illumination, e.g. such that collagen and/or elastin is produced in fibroblast. More preferably, illumination of skin in a therapeutic method according to the invention provides to said skin a power (irradiance) of between 90-150 or 130-180 W/m$^2$, preferably between 135-165 or 110-133 W/m$^2$, more preferably about 150 or 121 W/m$^2$ for light having the wavelength peak in aforementioned range (i), preferably 510-540 nm; a power (irradiance) of between 100-300 W/cm$^2$, preferably between 160-195 W/cm$^2$, more preferably about 177 or 224 W/m$^2$ for light having the required wavelength peak in the aforementioned range (ii), preferably 650-670 nm; and a power (irradiance) of between 20-50 W/m2, preferably between 30-40 W/m2, more preferably about 34 or 42 W/m$^2$ for light having the required wavelength peak in aforementioned range (iii), preferably 770-790 nm. The wavelength ranges in this aspect can be the same as used in other aspects of this invention.

Illumination of skin in a method for treating a skin-related disorder according to the invention is preferably performed using a power (irradiance) of light at the individual wavelength ranges that results in a therapeutically effective amount of the illumination, e.g. such that collagen and/or elastin is produced in fibroblast. More preferably, illumination of skin in a therapeutic method according to the invention provides to said skin a power (irradiance) of between 0.05-1 J/cm$^2$, preferably between 0.1-0.4 J/cm$^2$, more preferably about 0.36 J/cm$^2$ for light having the wavelength peak in aforementioned range (i), preferably 512-538 nm; a power (irradiance) of between 0.05-1 J/cm$^2$, preferably between 0.4-0.7 J/cm$^2$, more preferably about 0.53 J/cm$^2$ for light having the required wavelength peak in the aforementioned range (ii), preferably 652-668 nm; and a power (irradiance) of between 0.05-1 J/cm2, preferably between 0.05-0.2 J/cm$^2$, more preferably about 0.10 J/cm$^2$ for light having the required wavelength peak in aforementioned range (iii), preferably 768-788 nm. The wavelength ranges used in this aspect can be the same as used in other aspects of this invention.

A method for treating a skin-related disorder of the invention preferably further comprises the step of administering a composition comprising a skin care active ingredient, such as a pharmaceutically active agent to said subject, wherein said composition is administered prior to, and/or during and/or after illumination of skin. A composition as administered in a method for treating a skin-related disorder of the invention is preferably administered on skin of a subject or is administered through other routes but accumulates in skin of a subject, more preferably a part of skin that is illuminated, and/or is to be illuminated, and/or was illuminated. Most preferably, a composition of a method for treating a skin-related disorder of the invention is preferably applied topically on that part of skin of a subject that is at that moment illuminated, and/or is to be illuminated, and/or was illuminated.

A composition of a method for treating a skin-related disorder of the invention preferably comprises a skin care active ingredient as described above, preferably an active agent selected from antioxidants, including carotenoids, flavonoids and polyphenols, estrogen, vitamins and derivates thereof, peptides, including palmitoyl-lysine-threonine-threonine-lysine-serine, acetyl-glutamate-glutamate-methionine-glutamine-arginine-arginine and the tripeptide copper glycine-histidine-lysine, hydroxy acids, sugar amines, ceramides, metals, minerals, monoethanolamine, diethanolamine, sodium laureth sulfate, trans-retinoic acid, triethanolamine, phytomolecules, dipalmitoylhydroxyproline (DPHP), moisturizers and combinations thereof. An active agent of a composition of a method for treating a skin-related disorder of the invention described hereinabove can be administered for therapeutic or cosmetic purposes.

In a preferred embodiment, an active agent of a composition of a method for treating a skin-related disorder of the invention is DPHP. Preferably DPHP is present in a skin care active composition in a concentration of 0.0001 to 5 wt %, preferably 0.0010 to 4 wt %, more preferably 0.0015 to 3 wt %, even more preferably 0.0020 to 2 wt %, still more preferably 0.0025 to 1 wt % most preferably 0.175 wt % or 0.105 wt % based on the weight of the composition. DPHP is a powerful activator of the synthesis of different isotypes of collagen, especially collagen III, by fibroblasts. It simultaneously reduces the synthesis of metalloproteinases.

The invention also relates to DPHP for use in the treatment of skin wounds, wherein DPHP is topically applied to the surface of skin of a subject and wherein said skin is illuminated with light having a discontinuous spectrum with peaks corresponding to green light, red light and near infrared light; wherein said skin is illuminated simultaneously or successively with said wavelength peaks; and wherein said DPHP is applied prior to, and/or during and/or after illumination of said skin. Said illumination with light in DPHP for use in the treatment of skin wounds, may be performed by a light-emitting device according to the invention. The step of illuminating skin of a subject in DPHP for use according to the invention is essentially the same as the step of illumination as described for the cosmetic method above. Hence, features regarding illumination are interchangeable between the two.

In a further aspect, the present invention provides the use of a light-emitting device according to the invention for manufacturing, producing or providing one or more light beams; wherein said beams are for administration to the skin or illumination of the skin of a subject suffering, or suspected of suffering from a skin-related disorder, said light having a discontinuous spectrum with peaks corresponding to green light, red light and near infrared light, preferably wherein said skin is illuminated simultaneously or successively with said wavelength peaks. The step of illuminating skin of a subject in a use of a light-emitting device according to the invention is essentially the same as the step of illumination as described for the cosmetic method above. Hence, features regarding illumination are interchangeable between the two.

In an even further aspect, the present invention provides photons or light, preferably emitted from a light-emitting device according to the invention, having a discontinuous spectrum with peaks in wavelengths corresponding to green light, red light and near infrared light for use as a medicament.

The invention further provides photons or light, preferably emitted from a light-emitting device or light source, having a discontinuous spectrum with peaks in wavelengths in the ranges of (i) 495, 496, 497, 498, 499, 500, 501, 502, 503, 504, 505, 506, 507, 508, 509, 510, 511 or 512 nm, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm, for use as a medicament; wherein said skin is illuminated simultaneously or successively with said wavelength peaks. All possible combinations of wavelength ranges from (i), (ii) and (iii) mentioned in this paragraph are envisaged and intended to be individualized. Preferably, at least 50%, more preferably at least 55%, 60%, 65%, 70%, 75%, 80%, 85%, 90%, 95%, 96%, 97%, 98%, 99% or 100% of light or light energy emitted by a light-emitting device or light-source, is within the range of (i) 495, 496, 497, 498, 499, 500, 501, 502, 503, 504, 505, 506, 507, 508, 509, 510, 511 or 512, preferably 512 nm, to 566, 560, 555, 550, 545, 540, 536 nm, preferably 536 nm; (ii) 630, 635, 640, 645, 645, 650, 652 nm, preferably 652 nm, to 780, 750, 740, 730, 720, 710, 700, 695, 690, 685, 680, 675, 670 or 668 nm, preferably 668 nm and (iii) 700, 710, 720, 725, 730, 735, 740, 745, 750, 755, 760, 765 or 768 nm, preferably 768 nm, to 3000 nm, 2000 nm, 1500 nm, 1000 nm, 900 nm, 850 nm, 830 nm, 820 nm, 815 nm, 810 nm, 805 nm, 800 nm, 795 nm, 792 nm or 788 nm, preferably 788 nm. All possible combinations of wavelength ranges and light energy percentages are envisaged and intended to be individualized in this paragraph. The wavelength ranges useful in this aspect can be the same as used in other aspects of this invention.

In a preferred embodiment of photons for use according to the invention, the photons are for use in treating a skin-related disorder, preferably selected from the group formed by acute skin wounds, chronical skin wounds such as skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne and secondary acnes such as solar, drug or occupational acne, ichthyoses, ichthyosiform conditions, Darier's disease, palmoplantar keratoderma, leukoplakia and lueeoplakiform conditions or lichen and lichen planus, cutaneous, mucosal or ungual psoriasis, psoriatic rheumatism, cutaneous atopy including eczema, dry skin, inflammation of the skin, red flushes, solar skin erythema, actinic keratosis, skin allergies and allergic or irritant contact dermatitis, atopic dermatitis, rosacea, and lupus erythematous, and are directed to the skin of subject suffering, or suspected to suffer, from a skin-related disorder.

In a further aspect, the invention provides a method, preferably cosmetic or therapeutic, for providing skin care or for increasing collagen, preferably collagen III, content in the skin of a subject, comprising illuminating the skin of a subject with one or more light beams, said beams together providing light to the skin having a discontinuous spectrum with peaks in wavelengths corresponding to green light, red light and/or near infrared light, wherein said skin is illuminated simultaneously or successively with said wavelength peaks during an illumination period. The method for providing skin care as described above preferably comprises the combination of the application of a skin care active ingredient or composition together with phototherapy according to the present invention. Preferably the skin care active ingredient is as described herein above, and the skin care active composition for use in aspects of this invention may include such commercial preparations as Advanced Night repair (Estée Lauder), Perfectionist (Estée Lauder), Capture Totale (Dior), Capture XP (Dior), Lancôme—Advanced Génifique (L'Oréal), Lancôme—Absolue l'extrait (L'Oréal), Lancôme—Visionnaire (L'Oréal), Lancôme—Rënergie multilift (L'Oréal), Skinceuticals—CE Ferulic (L'Oréal), NTG—Rapide Wrinkles Repair (Neutrogena). Preferred examples of skin care active compositions in aspects of this invention include InDerm AF4036 (vide below in Example 10), Advanced Night repair (Estée Lauder), Perfectionist (Estée Lauder), Capture Totale (Dior), Capture XP (Dior), Lancôme—Advanced Génifique (L'Oréal), NTG—Rapide Wrinkles Repair (Neutrogena). Skin care active compositions in aspects of this invention can include any combination of skin care active ingredients described in aspects of this invention and in the examples herein below. The above compositions are envisioned for use in the second medical use or cosmetic aspects of this invention, including the skin care active composition for use in a method of treating a skin-related disorder as described herein above.

In a further aspect, the present invention provides the use of a light-emitting device according to the invention for manufacturing, producing or providing one or more light beams; wherein said beams are for administration to the skin or illumination of the skin of a subject suffering, or suspected of suffering from a skin-related disorder, said light having a discontinuous spectrum with peaks corresponding to green light, red light and near infrared light, preferably wherein said skin is illuminated simultaneously or successively with said wavelength peaks, whereby said skin-related disorder is cancer.

In a preferred embodiment, said use of a of a light-emitting device according to the invention for treating skin cancer is combined with a photosensitizer. A photosensitizer is defined as a compound that can be promoted to an excited state upon absorption of light and undergo intersystem crossing with oxygen to produce singlet oxygen. The singlet oxygen is highly cytotoxic. A wide array of photosensitizers exist and can be included for use of a light-emitting device according to the invention. Suitable photosensitizers included porphyrins, chlorophylls and dyes Preferred photosensitizers are aminolevulinic acid (ALA), 5 aminolevulinic acid (5-ALA) and ruthenium-based tethers, but the invention is not limited thereto.

For the purpose of clarity and a concise description, features are described herein as part of the same or separate aspects and preferred embodiments thereof, however, it will be appreciated that the scope of the invention may include embodiments having combinations of some or all of the features described.

The invention will now be illustrated by the following example, which is provided by way of illustration and not of limitation and it will be understood that many variations in the methods described and the amounts indicated can be made without departing from the spirit of the invention and the scope of the appended claims.

EXAMPLES

Materials and Methods
General Materials and Methods

In vitro cell culturing of keratinocytes and fibroblasts was performed by SAS Matriscience (Cochin hospital) in incubators set at 37° C. which are humidified and of which the atmosphere contains a 5% $CO_2$ atmosphere. The in vitro culture conditions are intended to represent the environment of the cells in vivo and the cells were cultivated under recommended or optimal growth conditions.

HEK cells are human skin keratinocytes obtained from different donors and cultured in the Celloneer KC/CC (Base Medium for keratinocytes and corneal cells). HEK cells are maintained in an incubator at 37° C. in a humid atmosphere (85-90% humidity) containing 5% $CO_2$. The medium was renewed four days after culturing, and then twice a week.

Fibroblasts (FPH) were obtained via surgical removal from healthy skin of a 42 year old woman—primary culture dated 5 Apr. 2011—cultured in Dulbecco's Modified Eagle's Medium (DMEM) supplemented with 10% fetal calf serum (FCS), 1% L-Glutamine (essential amino acid), salts, glucose and vitamins necessary for the stimulation of the cells and 1% penicillin-streptomycin. Cells are maintained in an incubator at 37° C. in a humid atmosphere (85-90% humidity) containing 5% $CO_2$. The medium was changed every 3-4 days.

At confluence, the cells in culture boxes T175 (Falcon) or T75 were passed, counted, and then returned to as much culture 24-well or 98-well boxes (Costar) as needed or passaged into new dish cultures. To this effect, cells were washed in 1× Phosphate Buffered Saline (PBS), then 4 ml of trypsin was added (for a T175 box) and 2 ml trypsin (for a T75 box) and left for 3 min at 37° C. The amount of trypsin to detach the cells introduced depends on the nature of the cells. Trypsin cleaves membrane adhesion proteins, and the cells are then left in suspension. The cells are collected in a volume of complete culture medium wherein FCS inhibits the action of trypsin and centrifuged at 200 g for 5 min. The supernatant was removed and the cell pellet was then suspended for recultivation.

Wound Repair Experiments

The cells were cultured in a 24-well box (20 to 30 000 cells per well). At confluence, a "wound" was made at the center of the well using an "Essen Woundmaker" (Essen Bioscience, Ann Arbor, USA). After rinsing the wells with PBS to remove detached cells, the optional test agent was applied and illumination was started.

Cell migration was followed by two types of instrumentation, (i) videomicroscopy or (ii) Incucyte (Essen Bioscience): whereby a photo from the culture well is recorded every 30 minutes or every hour over a period of 48 hours.

Healing of wounds was studied by dynamic microscopy using a Nikon Eclipse Ti microscope allowing the taking of pictures at intervals of 30 minutes for 24 hours on primary cultures of human fibroblasts and keratinocytes. In this way, it was possible to assess the level of healing.

Incucyte is a device for visualizing and quantifying cell migration in a $CO_2$ incubator at 37° C. The device is used with the Essen Woundmaker. The equipment was calibrated to produce wounds in cell cultures with high reproducibility. The device featured integrated processing software acquisition and image analysis allowing for quantification of the migration rate of cells.

Illumination by LEDs

Illumination was performed using a housing containing 11 different LEDs connected to a lighting test bench (Domteknica, Neuveville, Switzerland) for setting the desired power (irradiance) and illumination time. The test bench provided illumination of 11 wells of a culture dish (Costar) of 24 wells. The wavelengths of the LEDs in the test bench were selected to cover the spectral range of 450 nm to 1200 nm. The LEDs were procured from a single supplier (Thor Newtown, N.J., USA). Illumination overflow between wells was avoided by using black caps incorporated in illuminated adjacent wells and plates were placed on a black non-reverberating background. Each LED was connected to a generator, providing the ability to vary the power (irradiance) and fluence by varying voltage and current applied.

DPHP

Dipalmitoylhydroxyproline (DPHP or ASCIII), is a powerful activator of synthesis of different isotypes of collagen, especially collagen III, by fibroblasts. DPHP simultaneously reduces the synthesis of metalloproteinases and is marketed under the name RonaCare® (Merck KaG laboratories). DPHP was provided in the form of a serum for dilution in cell culture medium, in order to be administered to cells to perform the necessary tests. DPHP as used in the in vitro cell culture experiments, was comprised in a serum (AF3243bis) in a concentration of 0.175 wt % based on the weight of the serum.

Serum

A large number of commercial sera were tested as skin care active composition in ex vivo experiments as described in Example 10. One serum used in ex-vivo experimental sections of this invention is herein indicated as (InDerm AF4036), and contains (in wt % based on the weight of the serum): aqua (water): 79.55067%; butylene glycol: 8.4849%; glycerin: 4.6485%; pentylene glycol: 3%; *Euglena gracilis* extract: 2.971950%; sodium polyacrylate: 0.5%; chlorphenesin: 0.3%; dipalmitoyl hydroxyproline: 0.105% (unless otherwise indicated); hydrogenated lecithin: 0.09%; hydrogenated phosphatidylcholine: 0.06%; biosaccharide gum-1: 0.055%; lecithin: 0.03%; phenoxyethanol: 0.0297%; alcohol: 0.021%; hydroxypropyl cyclodextrin: 0.02%; glyceryl caprylate: 0.02%; potassium sorbate: 0.018%; sodium levulinate: 0.018%; sodium anisate: 0.018%; *Centella asiatica* extract: 0.0135%; citric acid: 0.01%; sodium benzoate: 0.009%; mannitol: 0.0075%; beta-sitosterol: 0.0072%; sodium hydroxide: 0.0045%; tocopherol: 0.00255; linoleic acid: 0.0015%; sodium ascorbate: 0.0015%; darutoside: 0.0015%; palmitoyl tripeptide-38: 0.0005%, biotin: 0.00003%. This serum is a separate aspect of this invention, e.g. as an example of a skin care active composition for use in aspects of this invention. Glycerin; *Euglena gracilis* extract; chlorphenesin; dipalmitoyl hydroxyproline; hydroxypropyl cyclodextrin; *Centella asiatica* extract; citric acid; tocopherol; sodium ascorbate; darutoside; palmitoyl tripeptide-38; and biotin are considered the core elements of this serum, and a serum based on these ingredients (in a suitable carrier) is considered an aspect of this invention, e.g. as an example of a skin care active composition for use in aspects of this invention.

Immunocytochemical Staining

The immunocytochemical staining allows the in situ identification of a cellular component with an antigen/antibody reaction specific to locate a protein or a complex in the cell by an indirect method comprising two steps: Initially, the cells are contacted with a primary antibody specific for the antigen of interest. Secondly, a second antibody labeled with a fluorochrome (eg Fluorescein isothiocyanate (FITC), Rhodamine, Texas Red® or Alexa Fluor®) binds to the primary antibody. Anti aSMA (smooth muscle actin) and anti-procollagen III are diluted 1/200 in Phosphate-buffered saline (PBS)+0.1% Tween20+1% Bovine serum albumin (BSA), and administered to the fibroblasts, which are incubated with said antibody overnight at 4° C. After rinsing, the secondary antibody coupled to a suitable fluorochrome—here type Alexa Fluor® 647 and Alexa Fluor® 488—is administered to the cells and incubated for 1 h at room temperature. The cells are then incubated in a dilute solution of 4', 6'-diamidino-2-phenylindole (DAPI) in PBS-BSA-Tween. DAPI is a fluorescent molecule able to bind strongly to the bases adenine and thymine in DNA. It emits bright blue fluorescence and marks the nuclei of cells in order to quantify them.

Ex-Vivo Experiments

Explants (11 mm±1 mm) were prepared from caucasian women abdominal plasties and cultured in 2 mL of conditioned medium (BEM) at 37° C., 5% CO2. Control (CTRL) explants were maintained in conditioned medium and received no treatment. Illumination by the 3LED device (520+660+780 nm light combination) was daily applied on dedicated samples for 2×15 sec. An amount of 2 gL of a commercial skin Serum (Dior Capture Totale Concentre multi-perfection or InDerm AF4036) was daily applied on dedicated samples. Other samples received 2 gL of the commercial skin Serum and 2×15 sec of illumination daily. For all samples, medium was renewed when needed.

After 10 days, explants were histologically fixed in formalin for 24 hours. Formalin-fixed paraffin-embedded tissue blocks were either sectioned to a thickness of 5 µm using microtome type Minot (Leica RM2125) and mounted on Superfrost slides or sectioned to a thickness of 7 µm using cryostat Leica CM 3050 and mounted on silanized Superfrost Plus slides. Standard microscopy observations were performed using Olympus BX34 optic microscope. Pictures and analysis were performed using Olympus DP72 camera and Cell^D software. Tissue morphology was performed by staining sections with Goldner Masson Trichrome. Total collagen was stained with Sirius red F3B. Collagen III was immunolabelled for 1 hour at room temperature with a 1/200 dilution of monoclonal anti-collagen III (Novus Biologicals, réf:AF5810) coupled to amplification biotin-streptavidin system revealed in VIP (Vectror Laboratories, Vector SK-4600). Acids glycosaminoglycans (GAGs) were stained with the combined alcian blue-PAS technique (Mowry 1956 (Mowry method).

Example 1. Irradiance has an Effect on Wound Repair

The setup of this experiment was as described in the Materials and Methods Section herein above. Essentially, keratinocytes were cultivated in DMEM until confluence as described, the confluent cell layer was damaged by scratching using a "woundmaker" as described above. Cells were then illuminated with light having the indicated wavelength characteristics.

Figure 2A:
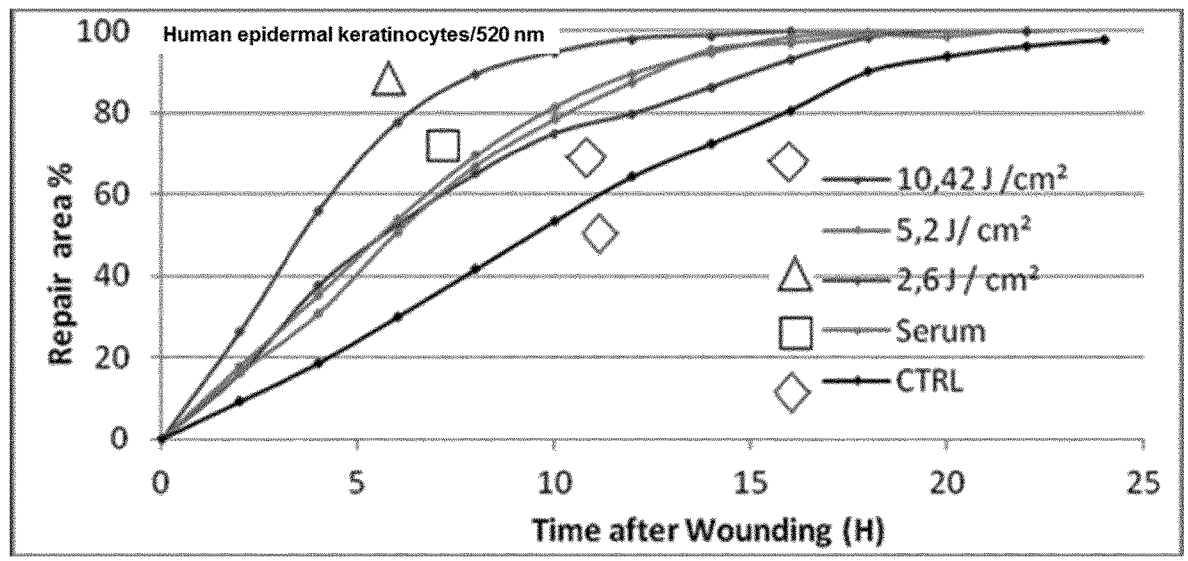
FIG. 2 shows the influence of the fluence of illumination on wound repair in the human epidermal keratinocyte cell culture model as exemplified in Example 1. Different wavelengths of illumination are indicated in panels A (520 nm), B (660 nm) and C (780 nm).
Figure 2B:
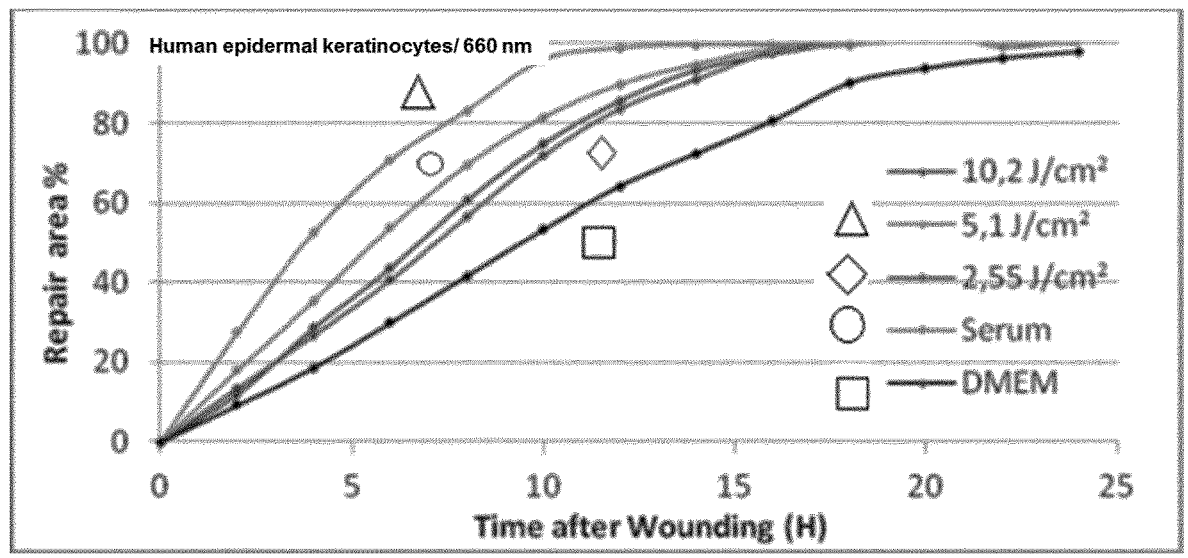
Figure 2C:
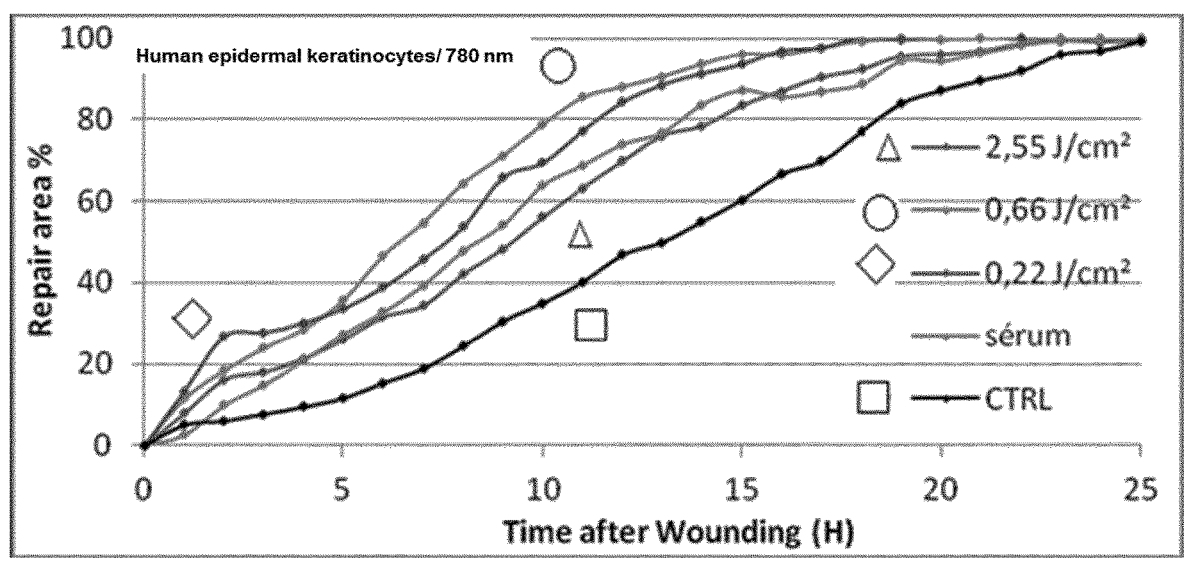

The illumination occurred by using a series of LEDs at power (irradiance) of 182 W/m$^2$ for the 520 nm LED; a power (irradiance) of 904 W/m$^2$ for the 660 nm LED, and a power (irradiance) of 62 W/m$^2$ for the 780 nm LED. Illumination was from a distance less than 1 cm. DMEM was used as the control (FIG. 2B). Serum (comprising DPHP) was added in an amount of 0.05 wt %. The illumination period was 1 times 15 seconds.

Over time, wound area or repair area (indicated by a shrinking wound area) was measured. The results of Example 1 are displayed in FIG. 2.

It was unexpectedly found that light of a specific combination of three wavelengths induces wound repair. In this Example, we demonstrate that the fluence or power (irradiance) provided to skin cells by illumination with LEDs set at emitting light of 520 nm, 660 nm and 780 nm has an effect on wound repair.

Example 2. 3-LED Lighting is Superior Over 1-LED Lighting and Alternative 3-LED Lighting The setup of this experiment was as described in the Materials and Methods Section herein above. Essentially, keratinocytes and fibroblasts were cultivated in DMEM until confluence as described, the confluent cell layers were damaged by scratching using a "woundmaker" as described above. Cells were then illuminated with light having the indicated wavelength characteristics.

The illumination occurred by using a series of LEDs at power (irradiance) of 182 W/m$^2$ for the 520 nm LED; a power (irradiance) of 904 W/m$^2$ for the 660 nm LED, and a power (irradiance) of 62 W/m$^2$ for the 780 nm LED. Illumination was for 15 seconds from a distance of less than 1 cm. DMEM was used as the control. Serum (comprising DPHP) was added in an amount of 0.05 wt %.

Figure 3:
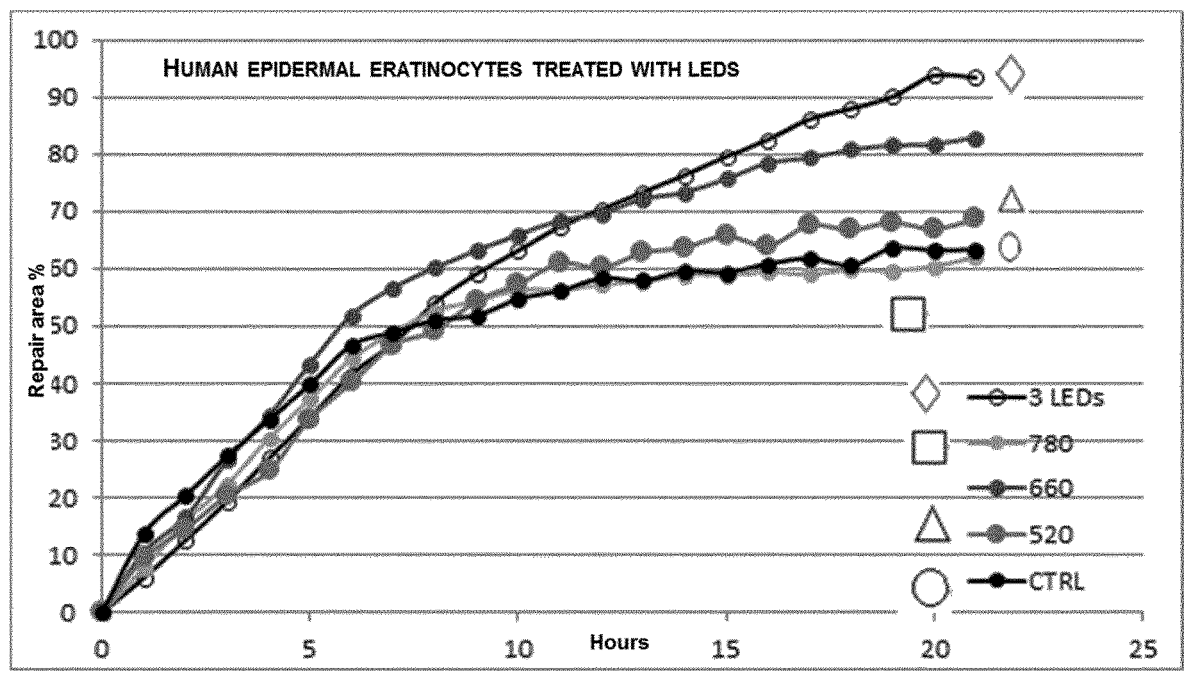
FIG. 3 shows the result of illumination of human epidermal keratinocytes (HEK) (panel A) and human skin fibroblasts (FPH) (panel B) with a combination of 3 LEDS set at emitting wavelengths of 520, 660 and 780 nm and illumination with each LED individually, as exemplified in Example 2. It clearly follows from FIG. 3 that the combination of the indicated wave lengths results in an increase in wound healing compared to illumination by a LED set at emitting light of an individual wavelength or no illumination at all (CTRL). The specific combination of 520 nm, 660 nm and 780 nm has photobiomodulatory effect on both keratinocytes and fibroblasts, superior to each single wavelength. There is faster experimental wound closure compared to control and compared to each single wavelength (780 or 660 or 520 nm).
Figure 3:
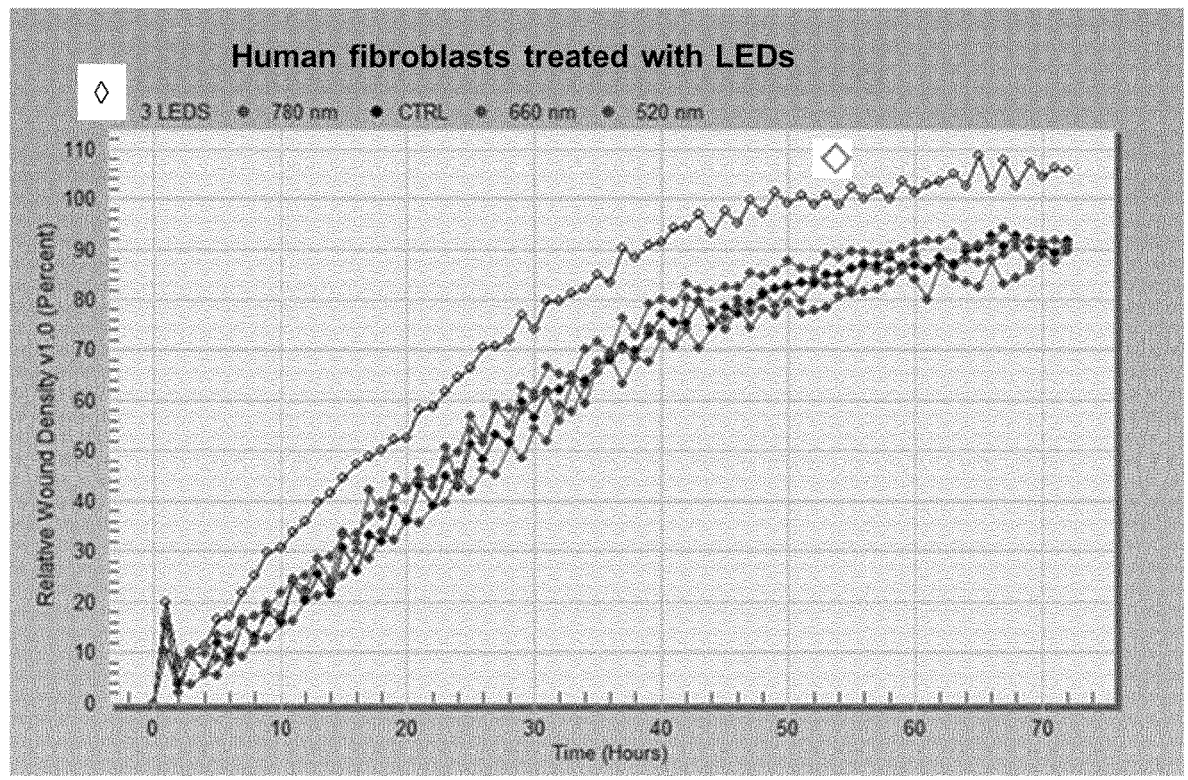

The results of Example 2 are displayed in FIG. 3. It can be clearly seen that in human epidermal keratinocytes, the illumination with the 3 LEDs of 520, 660, and 780-nm in accordance with the invention results in a higher degree of "wound" closure after 15-20 hrs following the illumination (FIG. 3A).

In human skin fibroblasts (FPH) (FIG. 3B) the illumination with the 3 LEDs of 520, 660, and 780-nm in accordance with the invention also results in a higher degree of "wound" closure after 5 hrs following the illumination. In the same manner, a comparative experiment was performed wherein a 3-LED lighting system was tested that was set at emitting wavelengths of 590 nm (0.15 A, 2 V), 635 nm (0.34 A, 2 V) and 735 nm (0.01 A, 1.7 V). The results of the comparative experiment are displayed in FIGS. 6 and 7.

Example 3. DPHP in Combination with 3-LED Lighting has a Positive Effect on Skin Wound Repair The setup of this experiment was as described in the Materials and Methods Section herein above. Essentially, keratinocytes were cultivated in DMEM in the presence or absence of a skin care active ingredient comprised in a serum (0.175 wt. % DPHP) until confluency was reached as described. The confluent cell layer was damaged by scratching using a "woundmaker" as described above. Cells were then illuminated with light having the indicated wavelength characteristics (3 LEDs).

The illumination occurred by using a series of LEDs at power (irradiance) of 182 W/m$^2$ for the 520 nm LED; a power (irradiance) of 904 W/m$^2$ for the 660 nm LED, and a power (irradiance) of 62 W/m$^2$ for the 780 nm LED). Illumination was for 15 seconds from a distance of less than 1 cm. DMEM was used as the control. Serum (comprising DPHP) was added in an amount of 0.05 wt % based on the weight of the medium.

Figure 4:
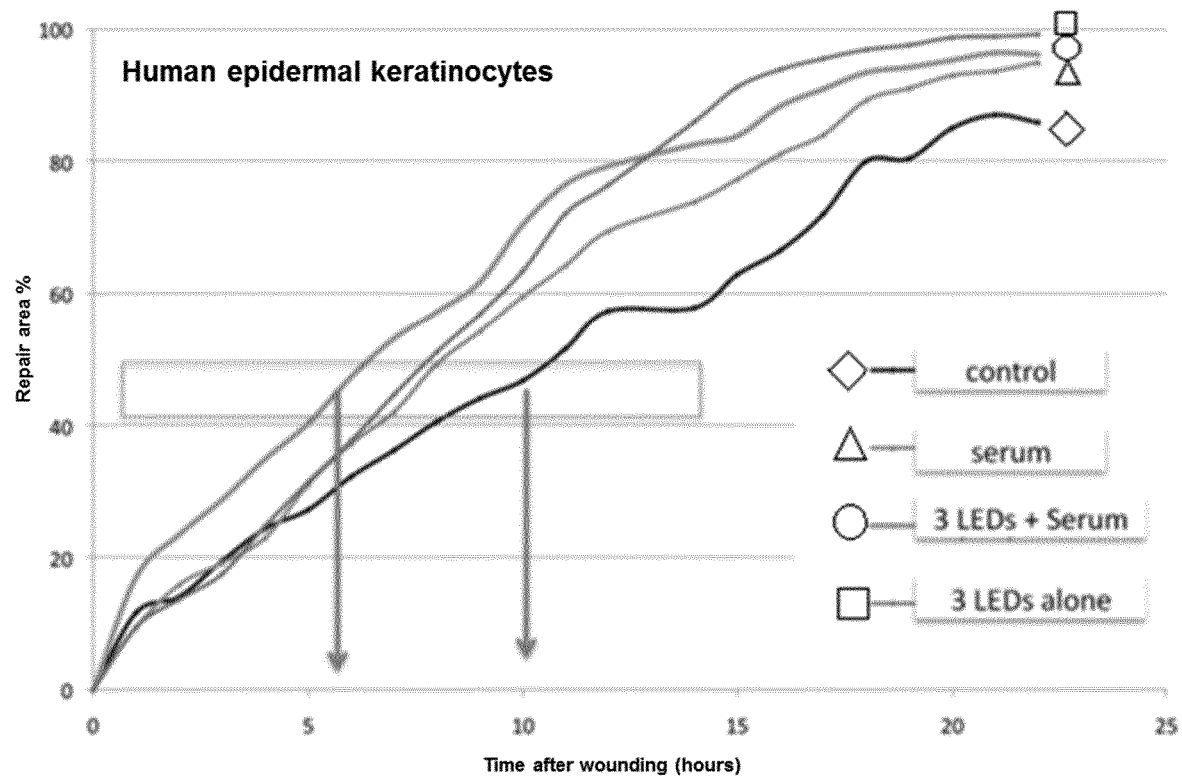
FIG. 4 shows that DPHP in combination with 3-LED lighting as disclosed herein, has a positive effect on skin wound repair. The experiment was performed as described in Example 3 using keratinocytes. CTRL, control experiment using Dulbecco's Modified Eagle's Medium; Serum, control experiment using a serum comprising DPHP as skin care active ingredient. The serum in this Example comprises a vesicular vector loaded with DPHP, such that the amount of DPHP in the serum is about 0.001-10 wt. %, preferably about 0.03-5 wt. % based on the weight of the serum. 3 LED+serum, test experiment using 3 LED illumination in the presence of serum; 3 LEDs alone, test experiment using 3 LED illumination in the absence of serum.

The results are displayed in FIG. 4. It can be clearly seen that in human epidermal keratinocytes, the presence of DPHP under illumination with the 3 LEDs of 520, 660, and 780-nm in accordance with the invention results in higher rate of "wound" closure (45% wound closure in 6 hours instead of 10 hrs).

Example 4: 3-LED Lighting Induces Collagen Production

Immuncytochemical staining of collagen III was performed as described in the Materials and Methods Section herein above. CTRL, control experiment using Dulbecco's Modified Eagle's Medium; CTRL+serum, DMEM including a serum comprising an amount of 0.1-3 wt. % of DPHP; 3LEDs+serum, LED illumination by the 3 wavelengths of 520, 660, and 780 nm while cells are cultivated in DMEM including an amount of 0.1-3 wt. % of DPHP.

The results clearly show the combined effect of illumination with wavelengths 520 nm, 660 nm and 780 nm together with serum application on the type III collagen production per fibroblast cell (expressed as the amount of collagen III in arbitrary units measured per nucleus).

Figure 5:
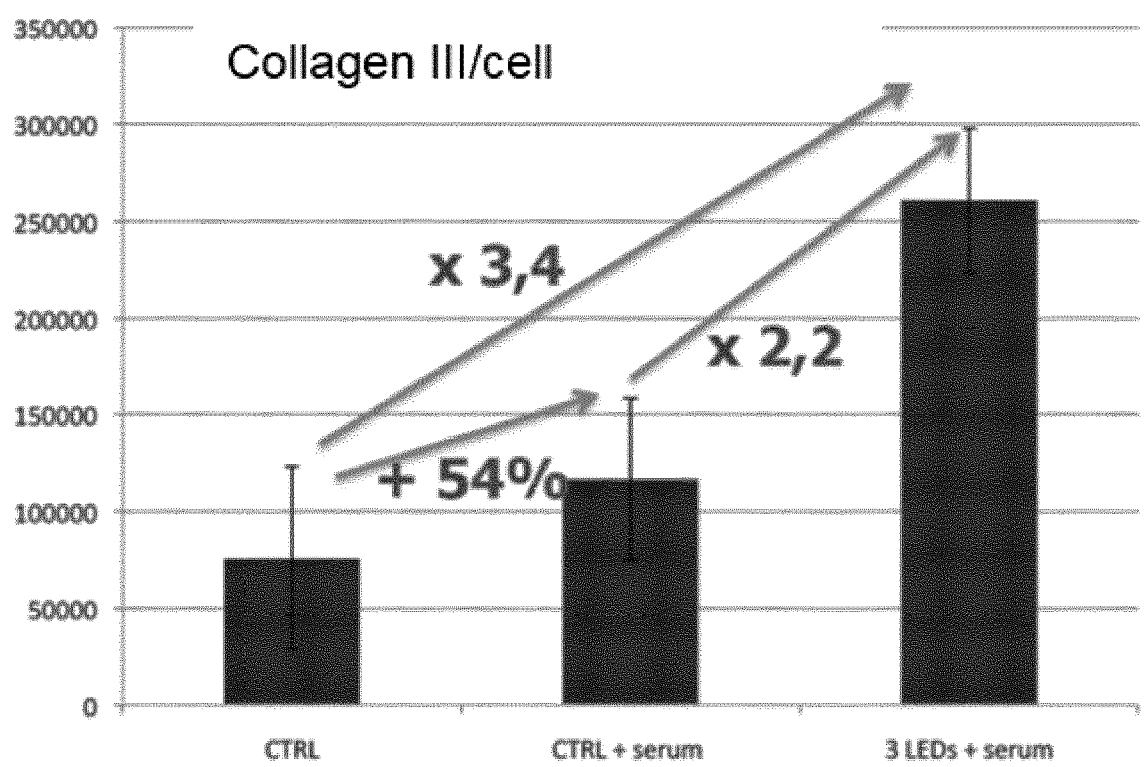
FIG. 5 shows collagen production induced by 3 LED lighting. The figure shows the combined effects of illumination by 3 distinct wavelengths together with serum application on type III collagen production per fibroblast cell (expressed as the amount of collagen III in arbitrary units measured per nucleus) as described in Example 4. CTRL, control experiment using Dulbecco's Modified Eagle's Medium; CTRL+serum, DMEM with serum including an amount of 0.03-5 wt. % of DPHP; 3LEDs+serum, LED illumination by the 3 wavelengths of 520, 660, and 780 nm while cells are cultivated in DMEM in which serum has been added including an amount of 0.03-5 wt. % of DPHP. The y-axis shows the amount of collagen III/cell.
Figure 6:
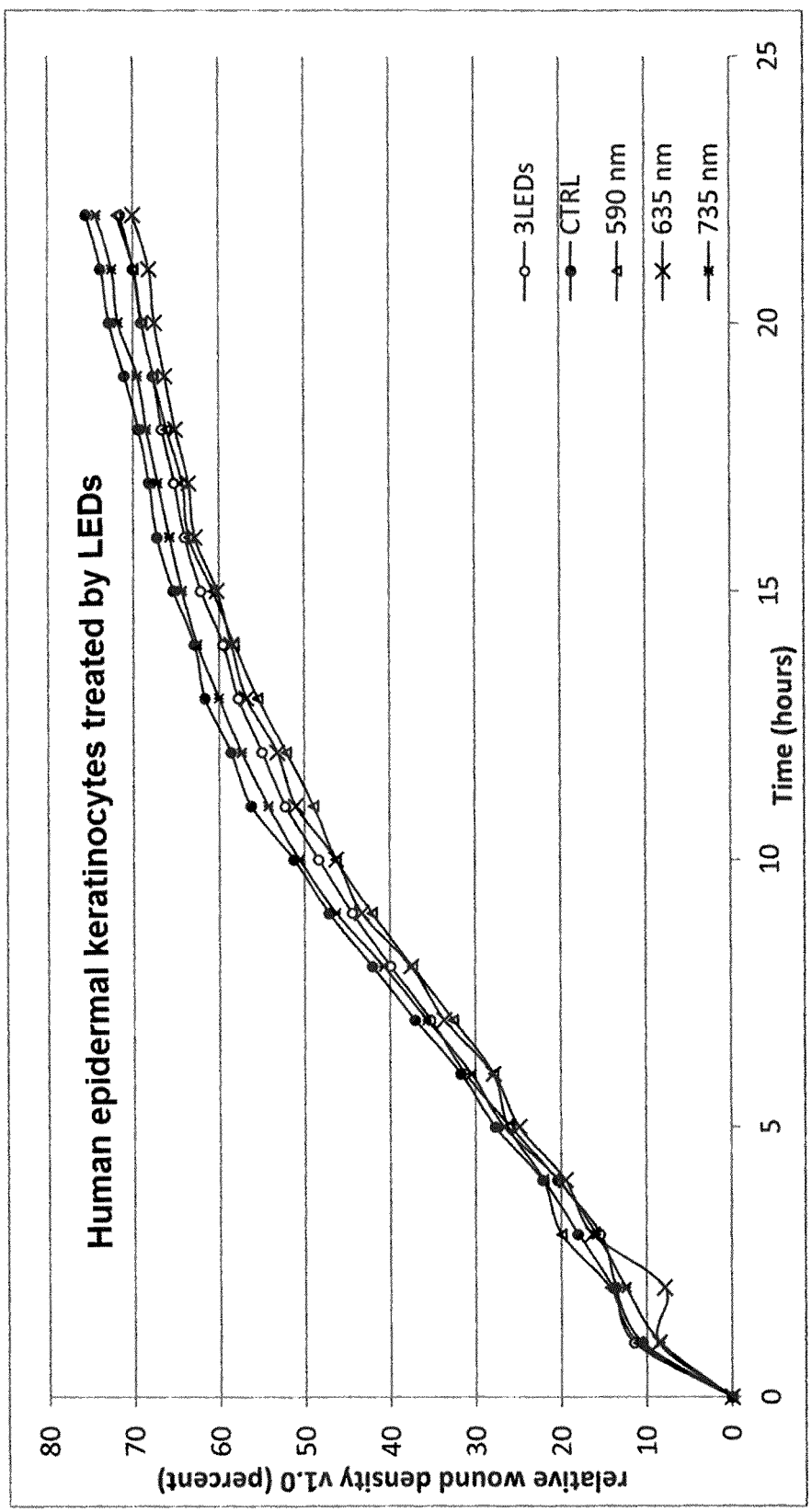
FIGS. 6 and 7 show the results of a comparative wound healing experiment wherein a different combination of wavelengths was tested as compared to the wavelengths that were found to provide for the effects as described herein. The control combination of wavelengths was provided by a 3-LED lighting system set at emitting light of 590 nm (yellow/orange light), 635 nm and 735 nm. Other parameters such as light intensity and voltage were kept essentially constant.
Figure 7:
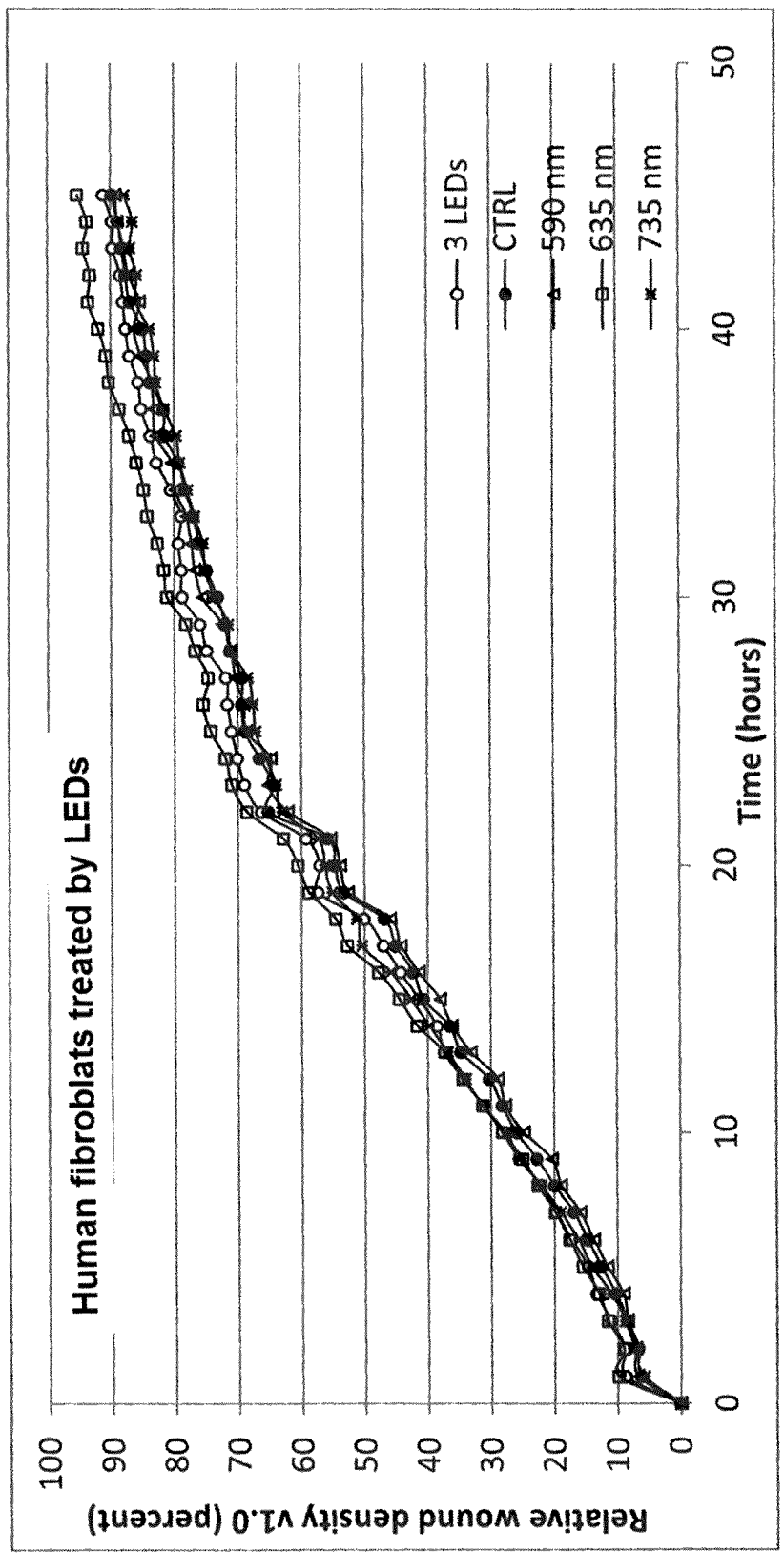

The results of Example 4 are displayed in FIG. 5.

Example 5: Illumination Period

Human skin explants were illuminated via LEDs set at emitting light of 520 nm (151 W/m$^2$), 660 nm (223.7 W/m$^2$)

or 780 nm (42.18 W/m$^2$) for either 1×15 seconds or 2×15 seconds. Collagen I and III were measured. It was found that an illumination period of 2×15 seconds increased collagen I and III production as compared to an illumination period of 1×15 seconds. This experiment can be repeated for a range of power (irradiance)s: between 113 and 189 W/m$^2$ for the 520 nm emitting LED, between 168 and 280 W/m$^2$ for the 660 nm emitting LED or between 31 and 52 W/m$^2$ for the 780 nm LED.

The results of Example 5 are displayed in FIG. 8.

Example 6: Comparative Experiment: Unpredictability of Effect of Individual Wavelengths This experiment is aimed to show that the use of one wavelength shows unpredictable effects at tissue, cellular and molecular levels. Illumination with individual wavelengths induces different responses in different cell types of the skin.

The setup of this experiment was as described in experiments 1 and 2 herein above. Essentially, keratinocytes and fibroblasts were cultivated in DMEM until confluence as described, the confluent cell layers were damaged by scratching using a "woundmaker" as described above. Cells were then illuminated with light having the indicated wavelength characteristics.

The illumination occurred by using a series of individual LEDs at power (irradiance) of 182 W/m$^2$ for the 520 nm LED; a power (irradiance) of 904 W/m$^2$ for the 660 nm LED, and a power (irradiance) of 62 W/m$^2$ for the 780 nm LED. Illumination was for 15 seconds from a distance of less than 1 cm. DMEM was used as the control.

Figure 10:
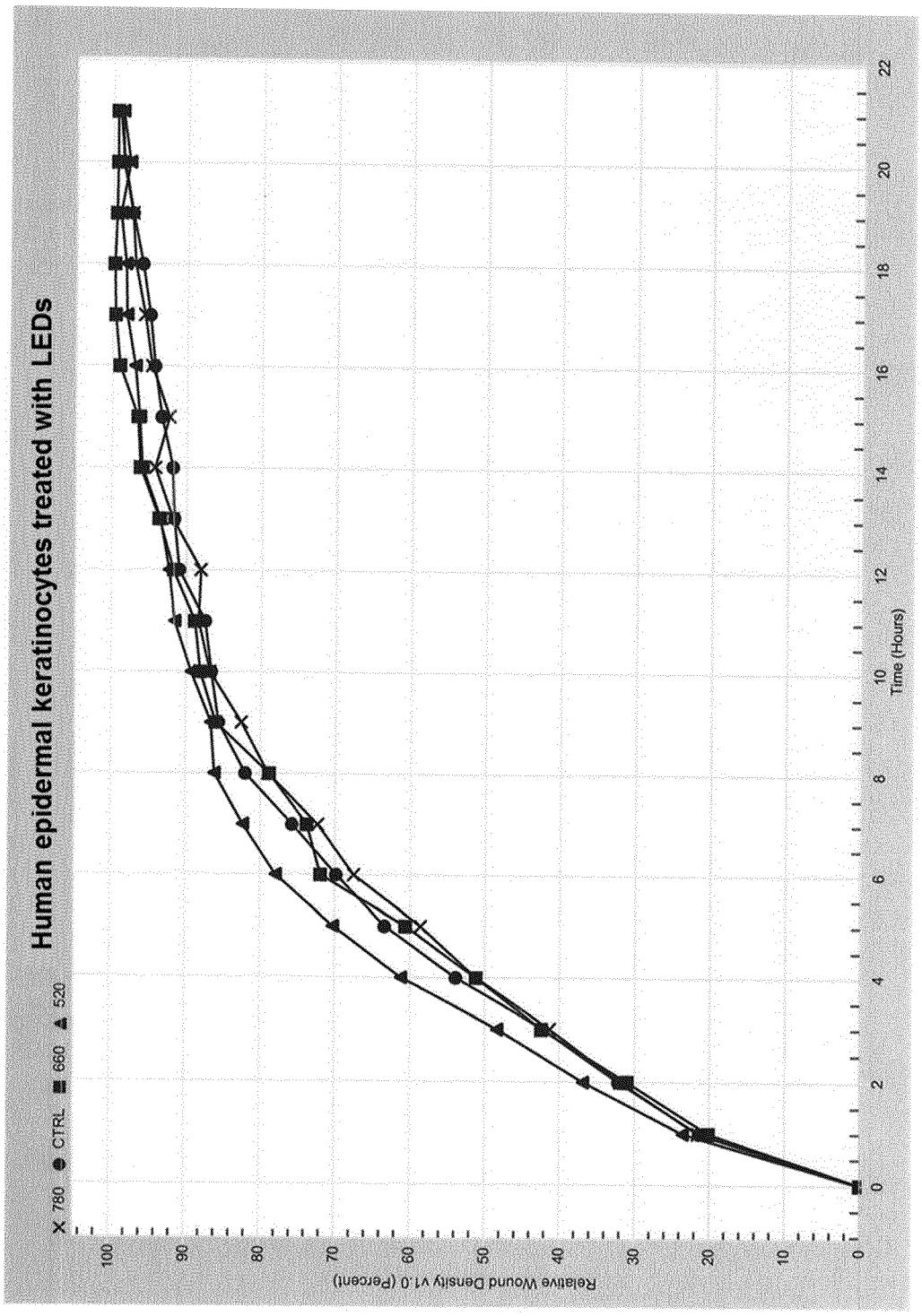
FIG. 10 shows keratinocytes illuminated with 520, 660, 780 nm LED light as described in Example 6. A LED with a wavelength of 520 nm has photobiomodulatory effect on keratinocytes. It shows faster experimental wound closure compared to control.
Figure 11:
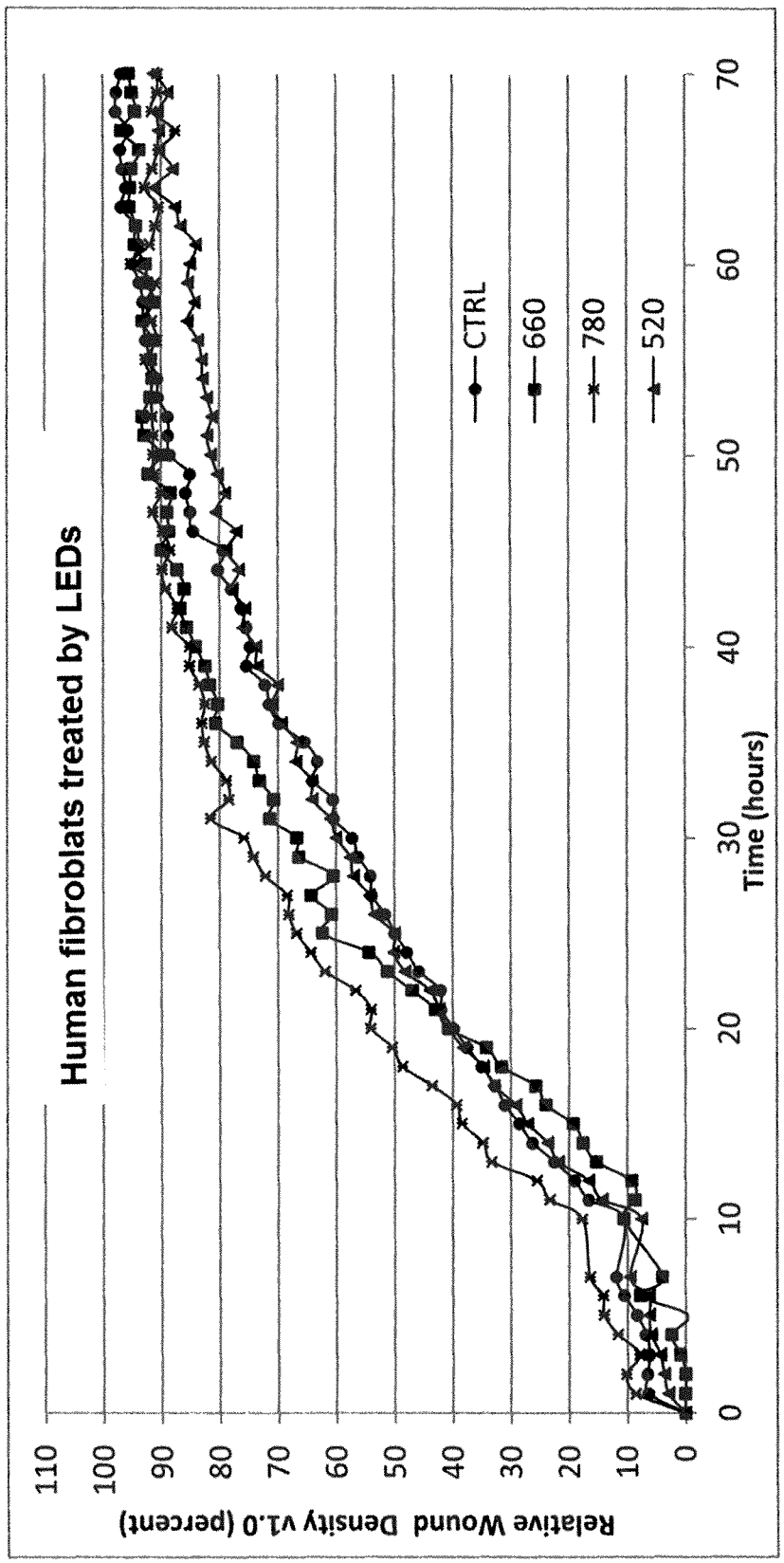
FIG. 11 shows fibroblasts illuminated with 520, 660, 780 nm LED light as described in Example 6. A LED with a wavelength of 520 nm has no photobiomodulatory effect on fibroblasts. There is similar experimental wound closure profile compared to the control.

The results show that light of 520 nm has a direct effect on keratinocytes proliferation but none on fibroblasts proliferation (FIGS. 10 and 11).

Example 7: Fibroblasts can be Activated by Illuminated Keratinocytes

This experiment was performed in accordance with Example 2. For this, Keratinocytes were illuminated with LEDs of different wavelengths (520 nm, 660 nm, and 780 nm), each wavelength separately, for a period of 15 sec. Thereafter, the keratinocytes were removed by centrifugation and the culture supernatant was used as a culture medium for the fibroblasts culture. No illumination of the fibroblast culture occurred therafter, and wound closing was measured in this fibroblast culture.

Figure 12:
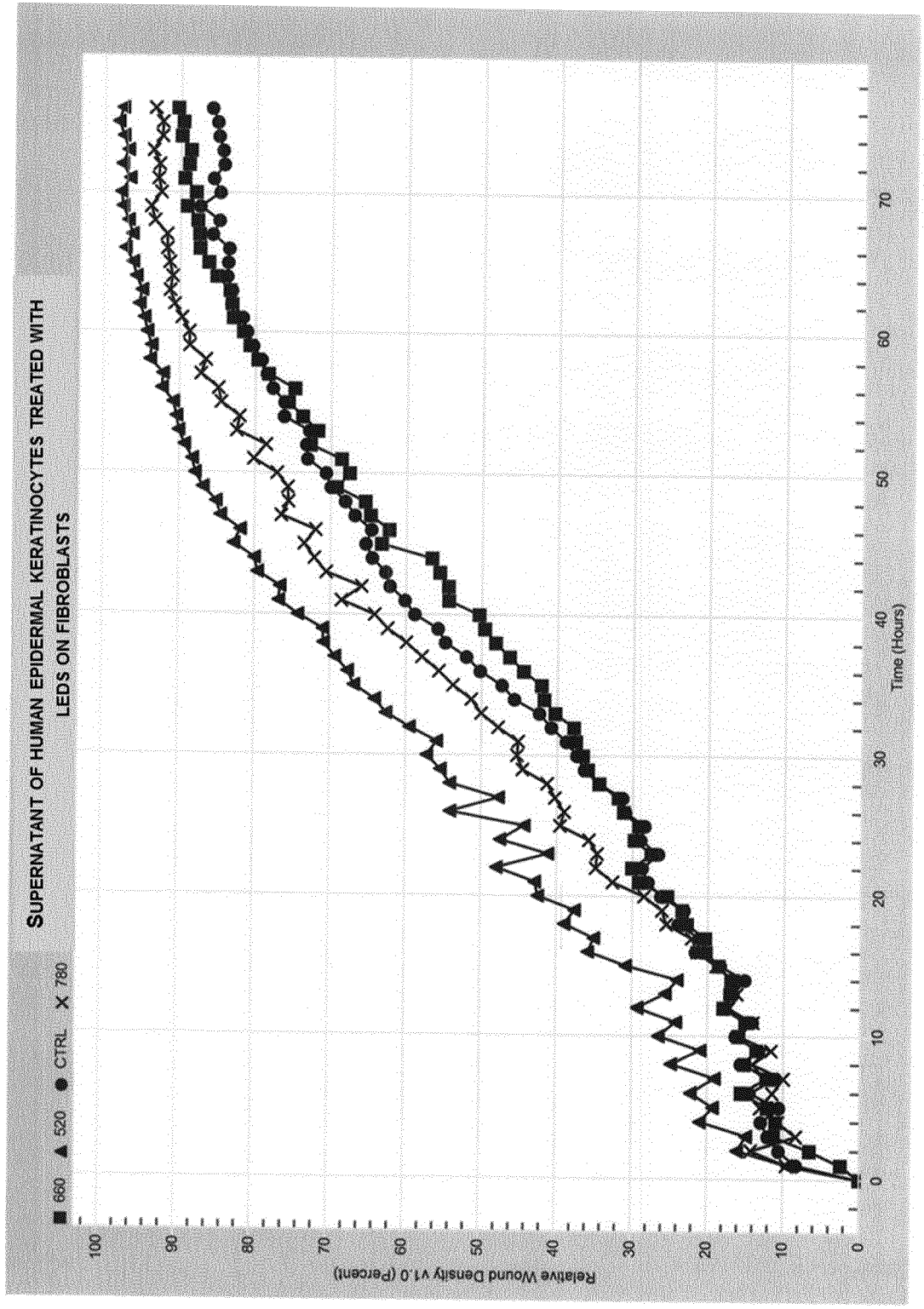
FIG. 12 shows the wound closure by fibroblasts cultured in the supernatant obtained from a keratinocyte culture that was illuminated with 520, 660, 780 nm LED light as described in Example 6. The 520 nm LED photobiomodulatory effect on keratinocytes clearly induces accelerated migration of fibroblasts and faster experimental wound closure in fibroblast culture. It is believed that this is indicative of the phenomenon that keratinocytes secrete activating factors for fibroblasts in response to 520 nm LED illumination.
Figure 13:
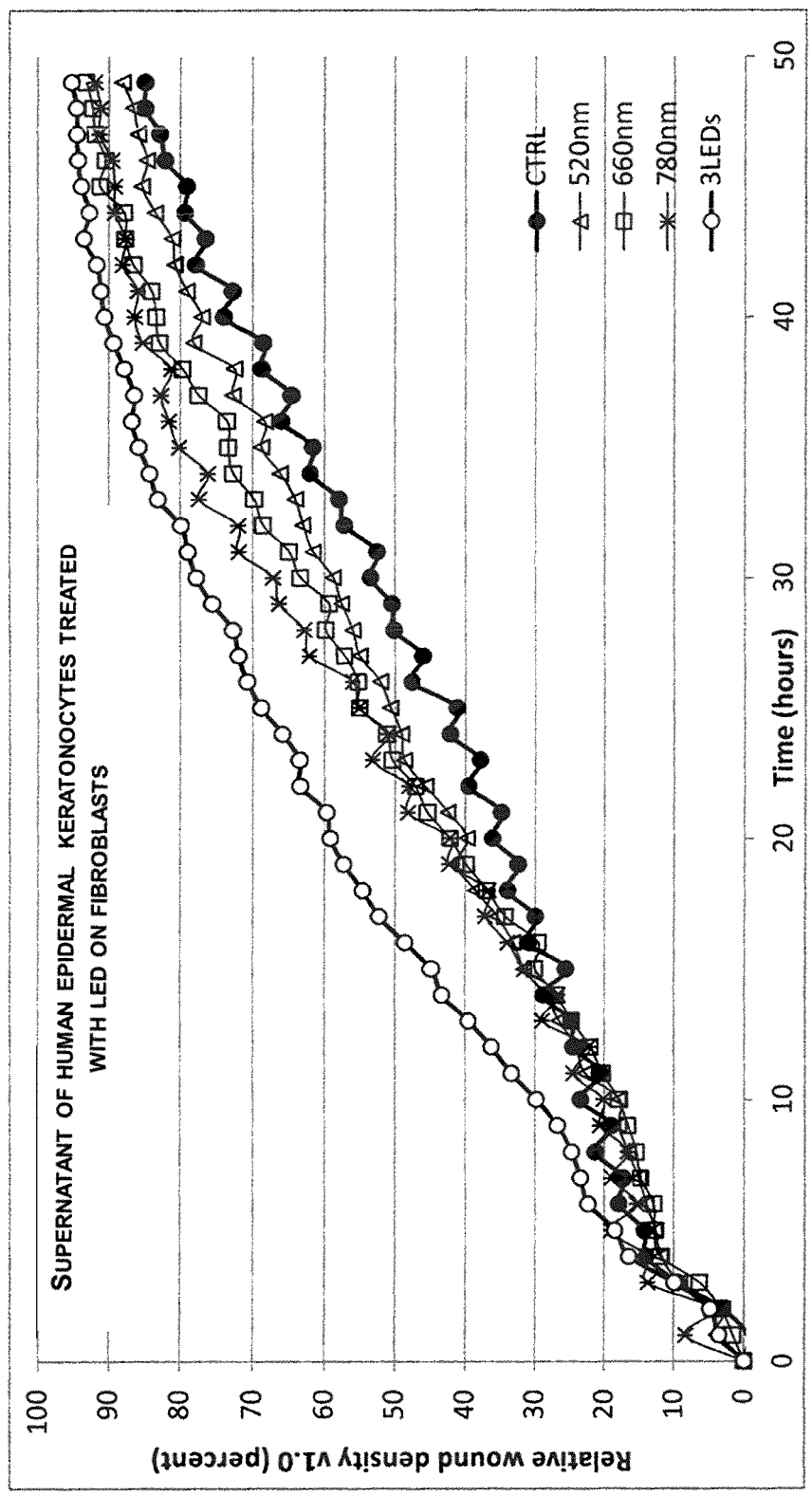
FIG. 13 shows the effect of the supernatant from keratinocyte cultures when illuminated with LED light on the growth of fibroblasts. The combination of 520 nm, 660 nm and 780 nm LED illumination results in a photobiomodulatory effect on keratinocytes, which induces accelerated migration of fibroblasts and faster experimental wound closure in fibroblast cultures. The illumination using the 3 combined wavelengths is superior to control and to each single wavelength. It is believed that keratinocytes secrete activator factors for fibroblasts in response to this specific 3-LED combination illumination.
Figure 14:
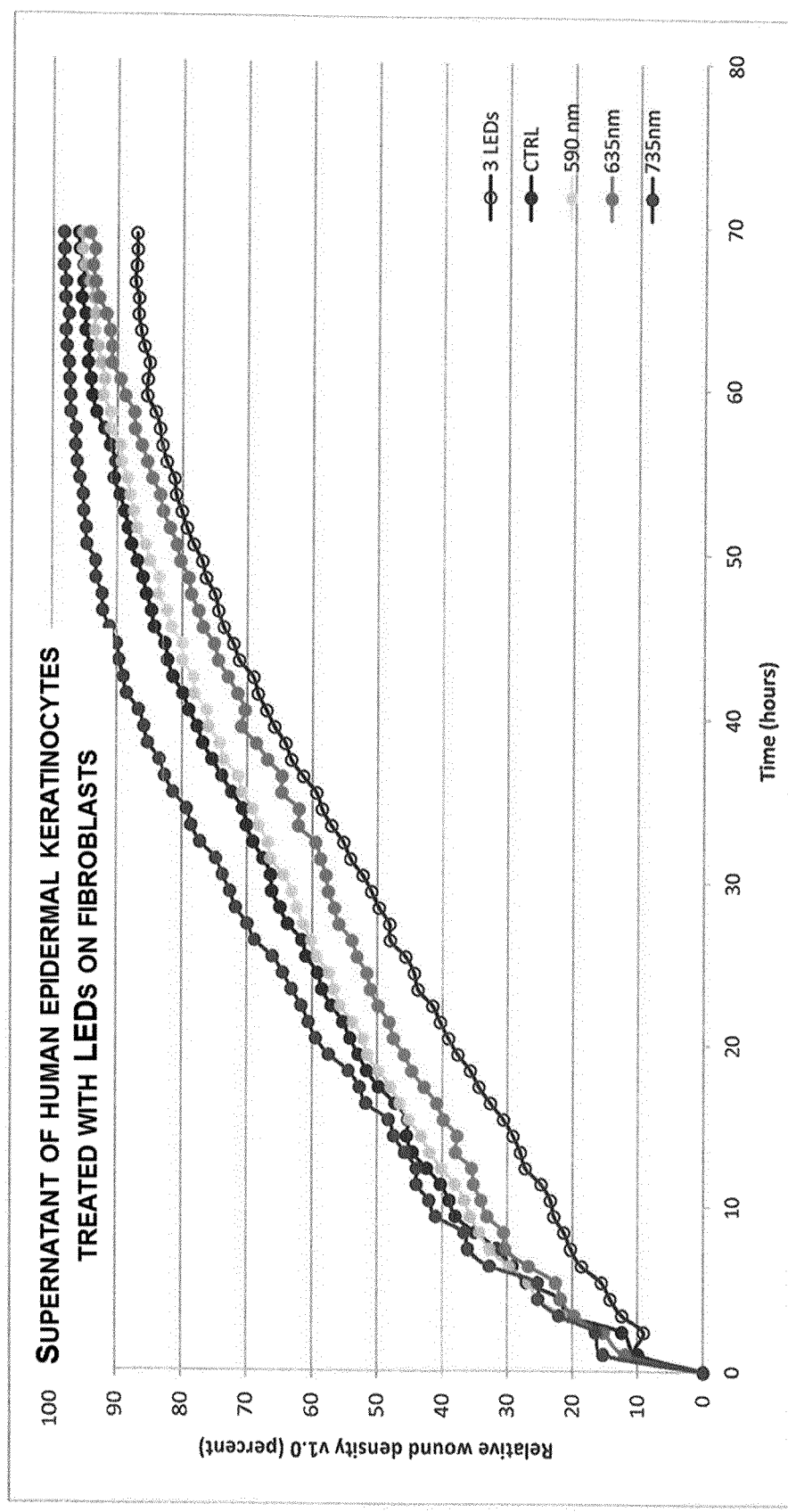
FIG. 14 shows a comparative experiment wherein the effect of supernatant of keratinocytes on migration and wound closure of fibroblasts, when illuminated with wavelengths other than 520, 660 and 780 nm, as described in Example 8.

Of the individual LED illuminations, only illumination of keratinocytes with 520 nm or 780 nm resulted in a keratinocyte culture supernatant that had a stimulatory effect on fibroblast migration and wound closures (FIG. 12).

In a further experiment, the combined effect of 520 nm, 660 nm and 780 nm 3-LED illumination according to the invention was tested and compared to illumination by LEDs set at emitting the individual wavelength values separately. The results thereof are displayed in FIG. 13. 3-LED illumination improves the keratinocyte supernatant effect as earlier observed and is superior to individual wavelength illuminations.

Example 8: Comparative Experiment: Unpredictability of Effect of Individual Wavelengths on Keratinocyte Supernatant Effect The 3-LED illumination experiment as described in Example 7 was repeated, but now with wavelengths 590 nm, 635 nm and 735 nm. The results thereof are displayed in FIG. 14. At 30 hrs, the orientation of curves from top to bottom is: 735 nm, control, 590, nm, 635 nm, and the S-LED combination 590+635+735 nm. There is no accelerated fibroblasts migration induced by keratinocytes supernatants and no faster experimental wound closure. There is even a deleterious effect resulting in delayed fibroblast migration and wound closure in the 3-LED illumination compared to control and compared to any single wavelength.

Example 9: Comparative Experiment: Dual Wavelength Illumination does not Result in the Observed Biomodulatory Effect of 3-LED Illumination The cell illumination experiments as described in Examples herein above were also evaluated for dual wavelength combinations. Keratinocyte cultures and fibroblast cultures were illuminated with two-wavelength combinations 520 nm+660 nm, 520 nm+780 nm, 660 nm+780 nm, and compared to the 3-LED illumination.

Figure 15:
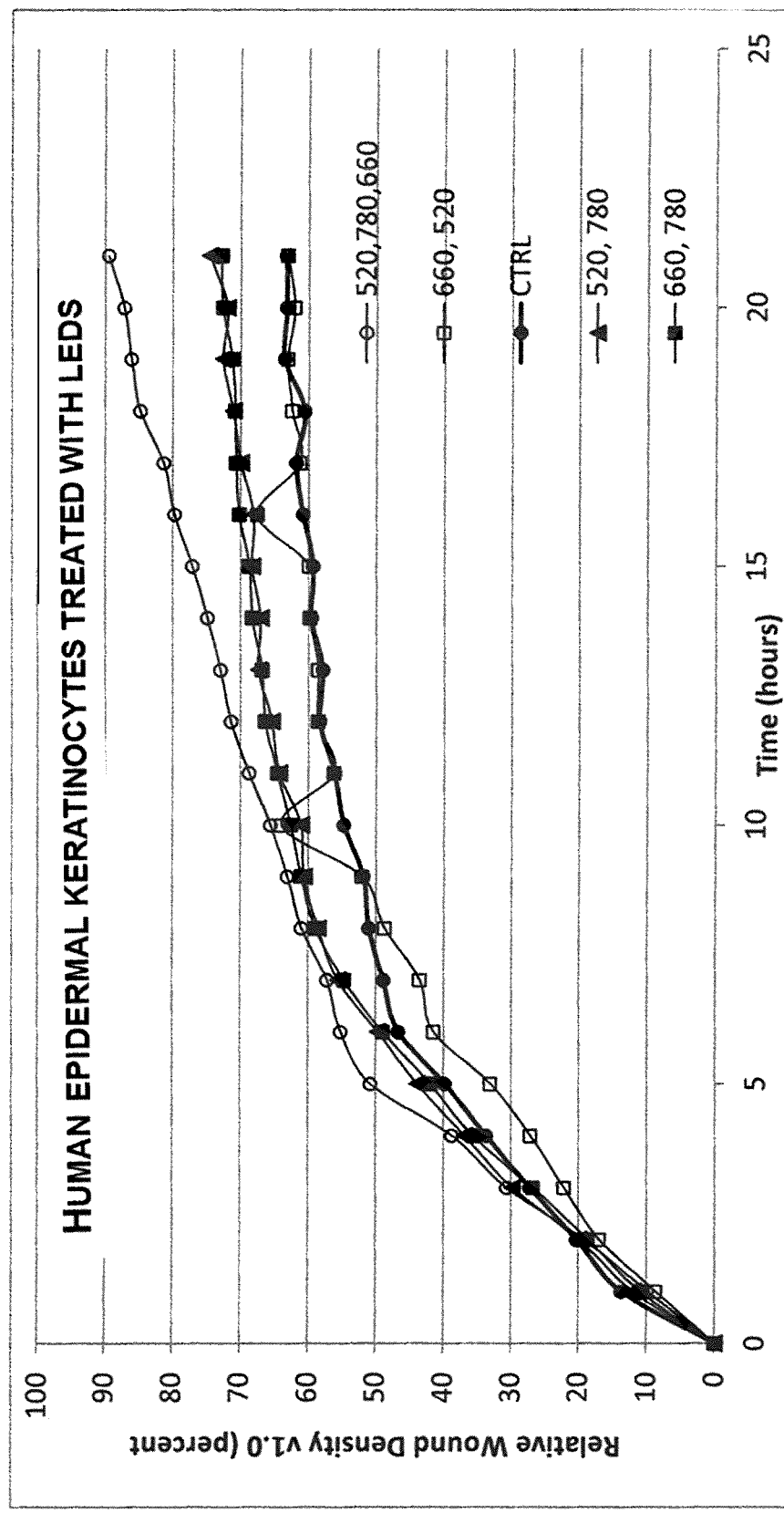
FIG. 15 shows keratinocytes treated (illuminated) with LEDs as described in Example 9.

The results on keratinocytes show that the combined illumination with 520 nm, 660 nm and 780 nm LEDs has photobiomodulatory effect on keratinocytes that is superior to each dual wavelength combination (660+780 or 520+780 or 660+520 nm). There is faster experimental wound closure compared to control and compared to each dual wavelength combination (FIG. 15).

Figure 16:
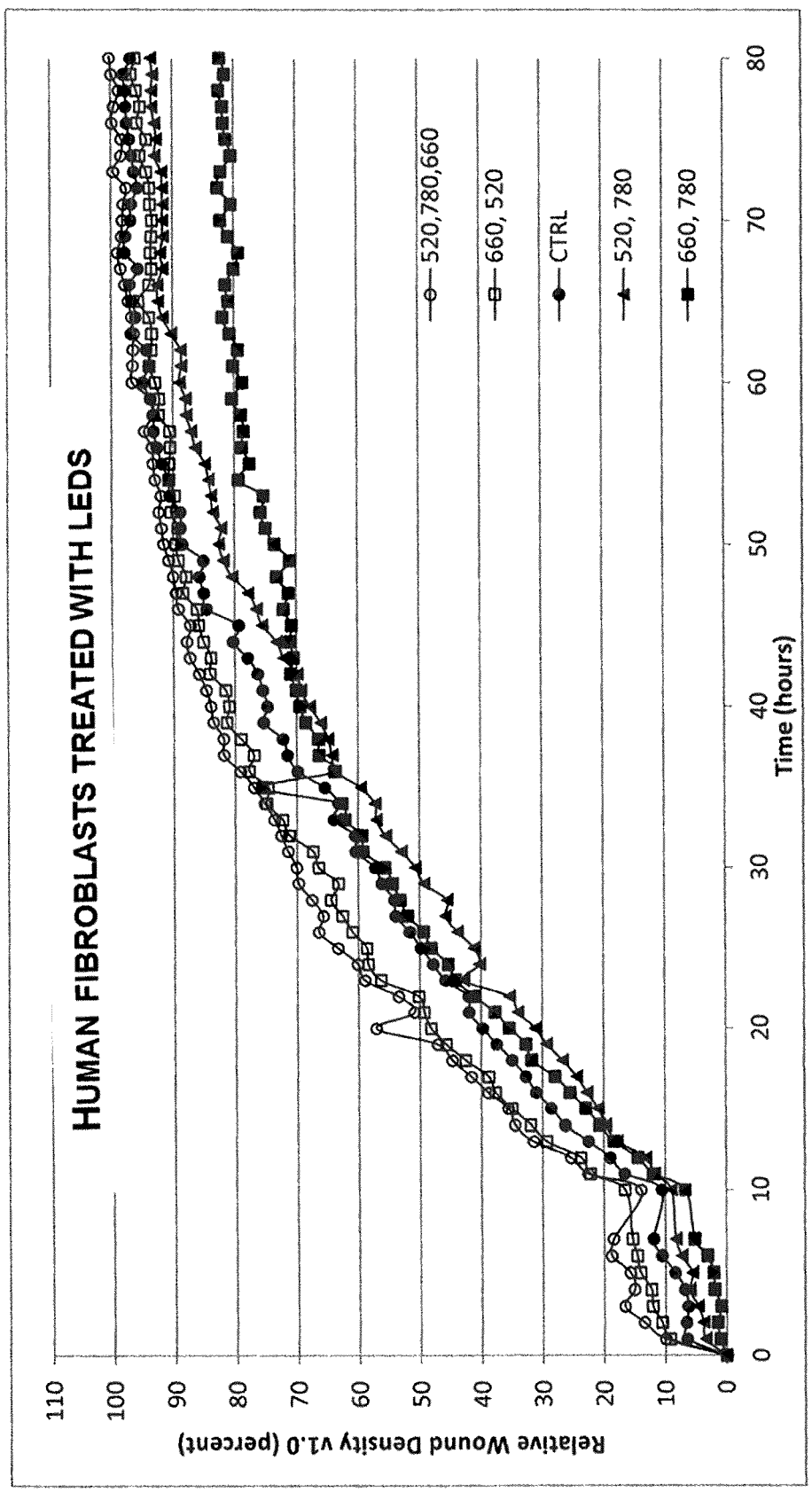
FIG. 16 shows fibroblasts treated with LEDs as described in Example 9.

The results on fibroblasts show that the specific combination of 520 nm, 660 nm and 780 nm LED illumination has photobiomodulatory effect, superior to each dual wavelength combination (660+780 or 520+780 or 660+520 nm). There is faster experimental wound closure compared to control and compared to dual wavelength combinations (FIG. 16).

Figure 17:
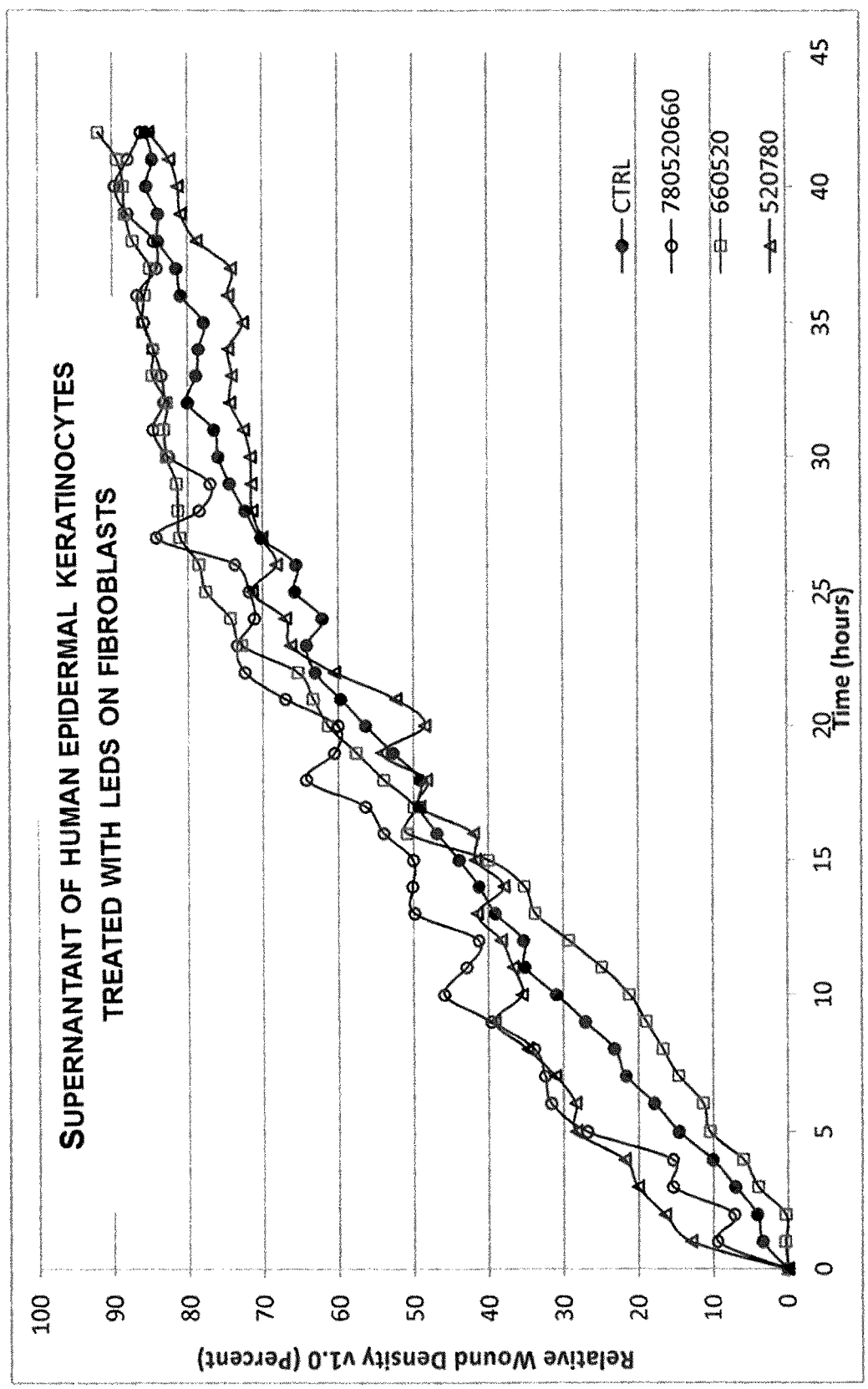
FIG. 17 shows supernatant of keratinocytes treated with LEDs on fibroblasts as described in Example 9.

There is also an accelerated fibroblasts migration induced by keratinocytes supernatants and faster experimental wound closure upon the combined illumination with 520 nm, 660 nm and 780 nm LEDs as compared to each dual wavelength combination (660+780 or 520+780 or 660+520 nm) (FIG. 17).

Example 10: Ex Vivo Experiments

Ex vivo experiments were performed as described above. The results are displayed in FIGS. 18-22.

Figure 18:
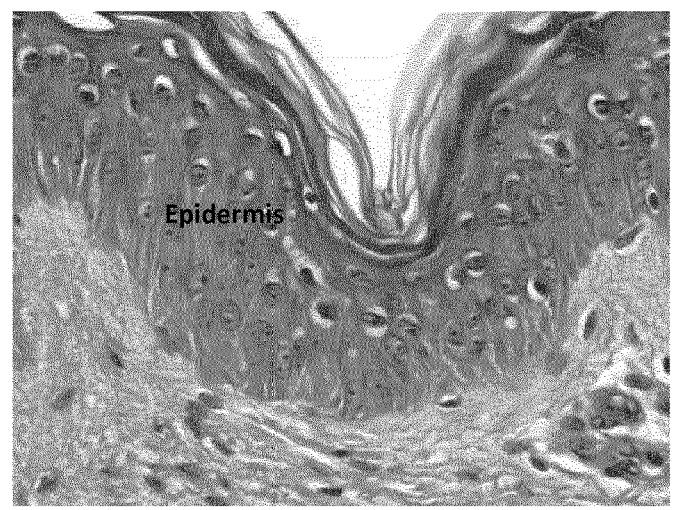
FIG. 18 shows the result of ex vivo skin illumination as exemplified in Example 10, indicating that specific combination of 520 nm, 660 nm and 780 nm LEDs also has photobiomodulatory effect on epidermis ex-vivo. In skin explants, 3-LED illumination according to the invention increases epidermis thickness via increasing the epidermis cell layer. Panel A: Control; panel B: combination of 520 nm, 660 nm and 780 nm LEDs; Panel C: graphic representation of measured values for epidermis thickness for control and experimental conditions, showing a 24% increase upon phototherapy.
Figure 18:
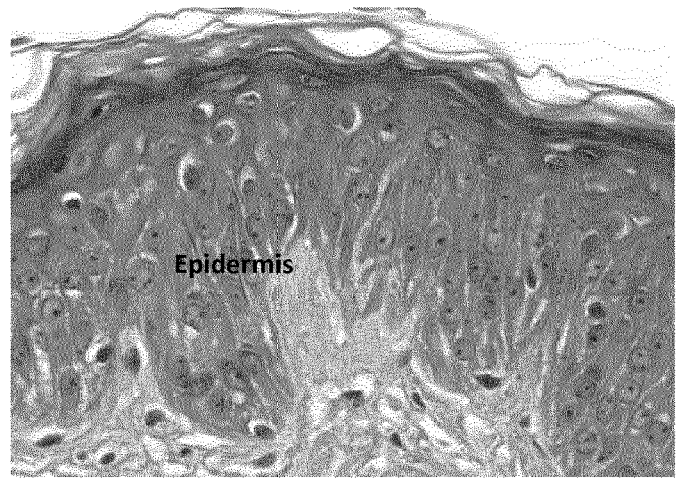
Figure 18:
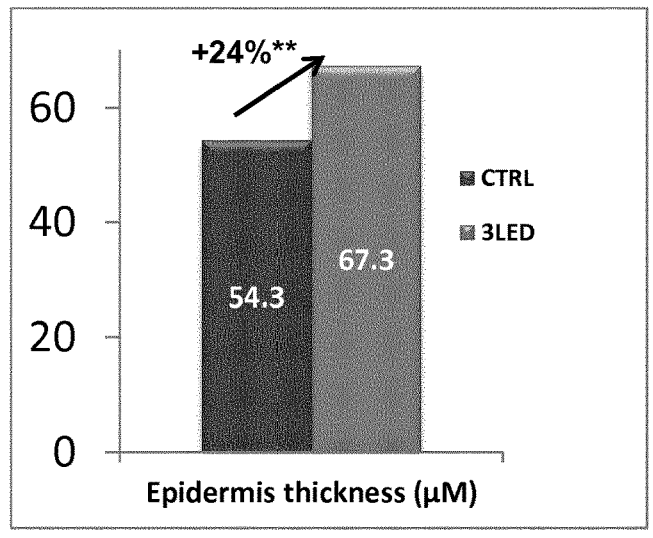

First, epidermis thickness was measured. Phototherapy alone using the inventive combination of 520 nm, 660 nm and 780 nm LEDs, was tested on skin explants (FIG. 18). Phototherapy according to the invention caused a 24% increase in epidermis thickness.

Figure 19:
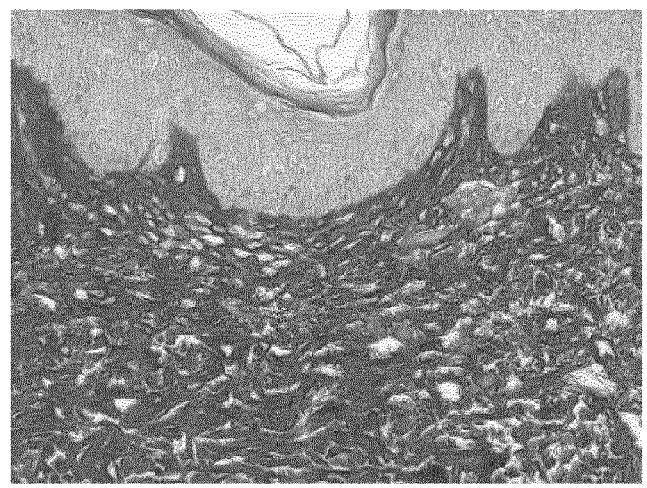
FIG. 19 shows that triple LED illumination with 520 nm, 660 nm and 780 nm LEDs has photobiomodulatory effect in skin explants as exemplified in Example 10. It increases matrix protein expression of total collagen (Panel B), compared to the control (Panel A), by some 11% (Panel C). Panel C provides a graphic representation of measured values for total collagen for control and experimental conditions, showing an 11% increase upon phototherapy.
Figure 19:
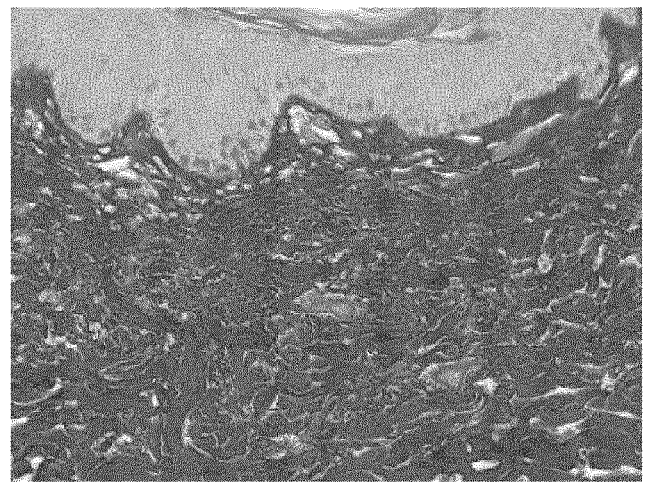
Figure 19:
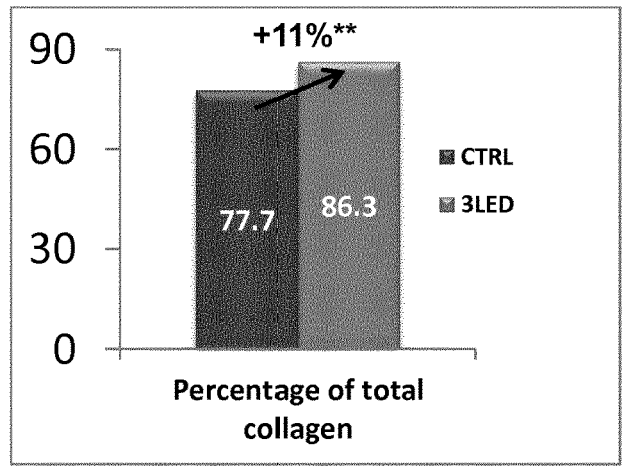
Figure 20:
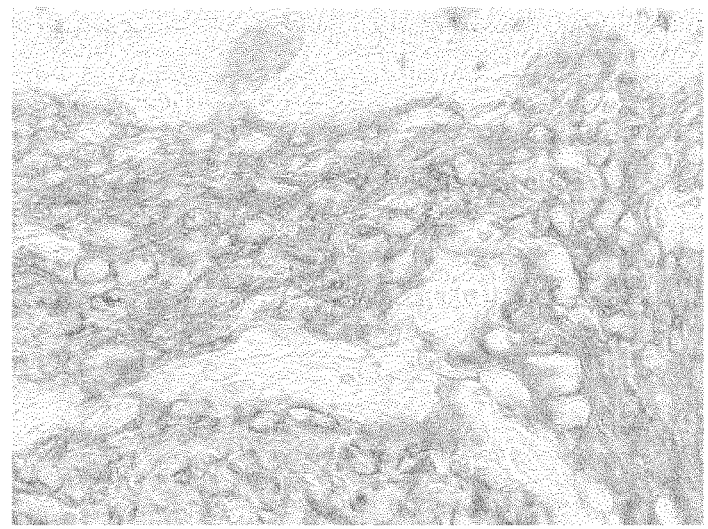
FIG. 20 shows that triple LED illumination with 520 nm, 660 nm and 780 nm LEDs has photobiomodulatory effect in skin explants as exemplified in Example 10. It increases matrix protein expression collagen III in explants (Panel B), compared to the Control (Panel A) by a factor of 3 (Panel C). Panel C provides a graphic representation of measured values for collagen III for control and experimental conditions, showing a 322% increase of collagen III in ex vivo skin experiments of phototherapy according to the present invention.
Figure 20:
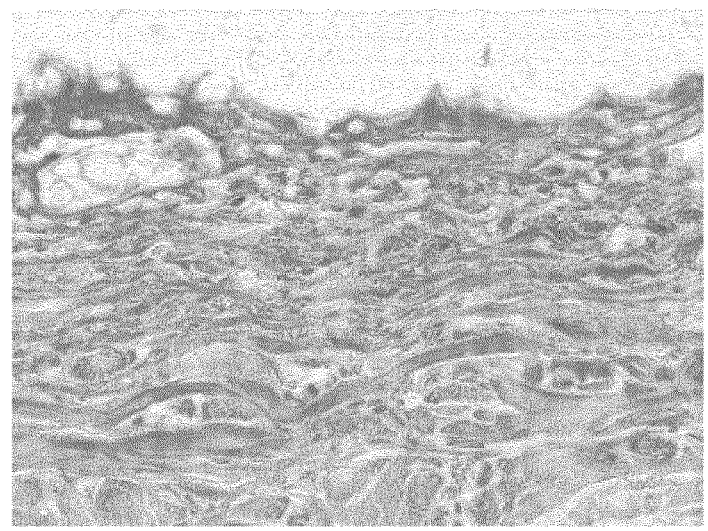
Figure 20:
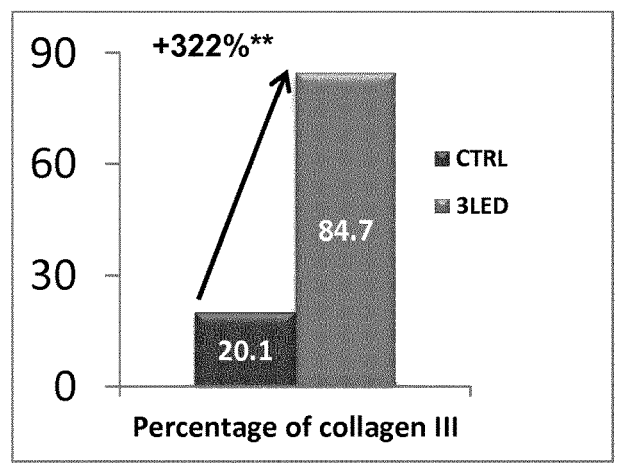

Second, matrix protein expression of total collagen was measured. Phototherapy alone using the inventive combination of 520 nm, 660 nm and 780 nm LEDs, was tested on skin explants (FIG. 19). Phototherapy according to the invention caused an 11% increase in total collagen. Next, matrix protein expression collagen III was measured. Phototherapy alone using the inventive combination of 520 nm, 660 nm and 780 nm LEDs, was tested on skin explants (FIG. 20). Phototherapy according to the invention caused a 322% increase in collagen III expression.

Figure 21:
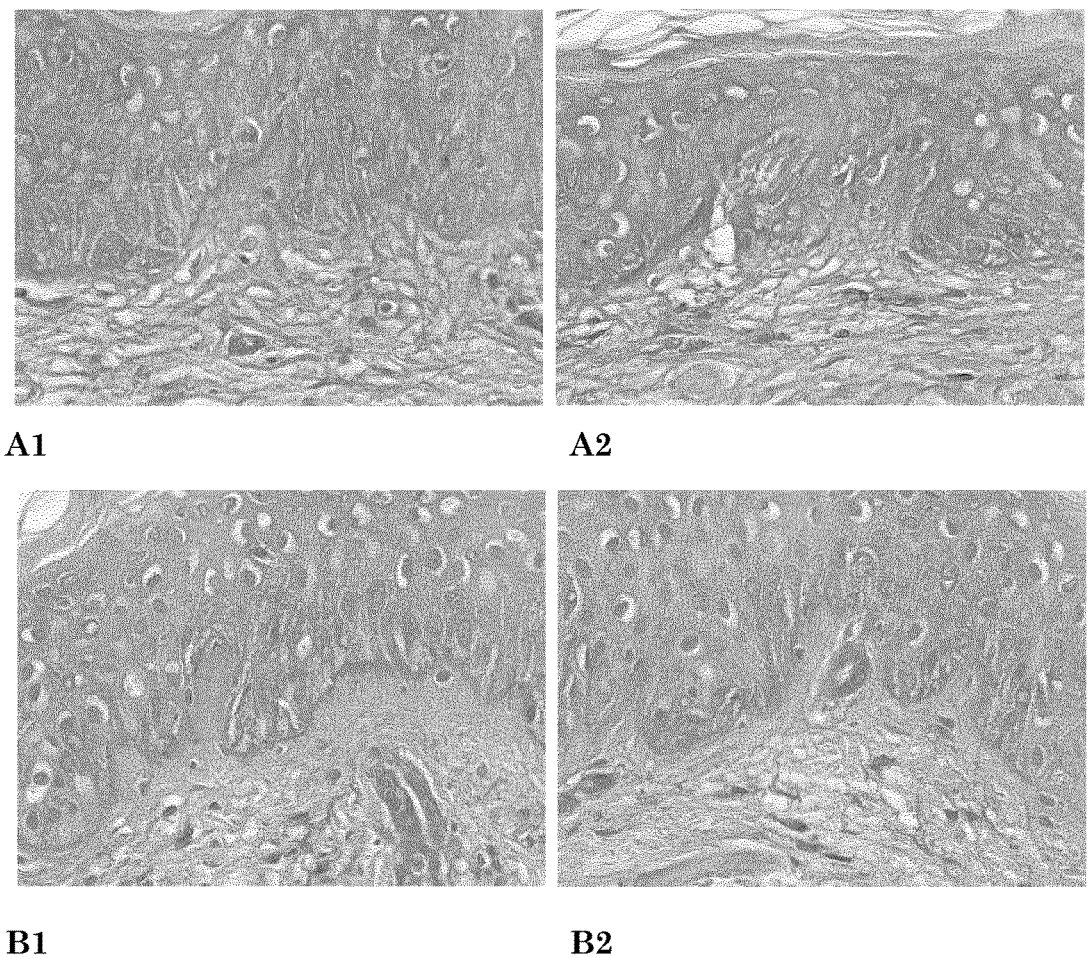
FIG. 21 shows the ability of the phototherapeutic light treatment using the specific combination of 520 nm, 660 nm and 780 nm LEDs (3LED) according to the present invention to induce acid glycosaminoglycane (GAG) expression in skin tissue explants as exemplified in Example 10. Figure A1 and A2 indicate controls (no illumination) and show no staining of skin explants after Alcian Blue-PAS staining. Figures B1 and B2 indicate blue staining throughout the dermis. The acid GAGs are mainly composed of hyaluronic acid and are involved in the dermis architecture and skin tissue moisturization.

Next, acid glycosaminoglycane (GAG) expression was measured. Phototherapy alone using the inventive combination of 520 nm, 660 nm and 780 nm LEDs, was tested on skin explants (FIG. 21). Phototherapy according to the invention resulted in detectable presence of acid GAGs mainly composed of hyaluronic acid.

Figure 22:
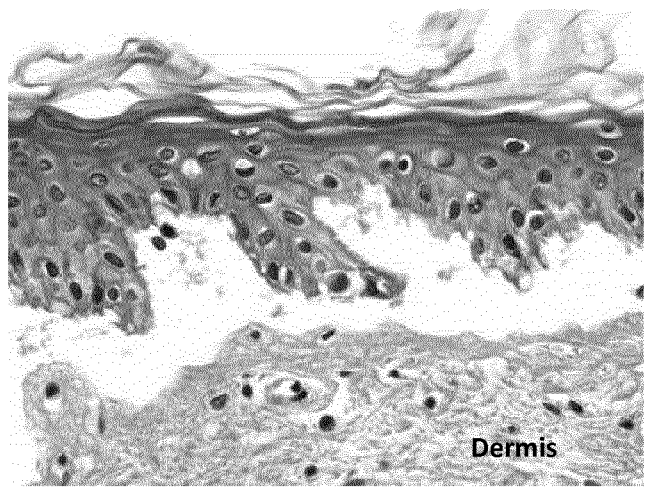
FIG. 22 shows the result of ex vivo skin illumination as exemplified in Example 10, indicating that the specific combination of 520 nm, 660 nm and 780 nm LEDS has also a photobiomodulatory effect on the dermis and on the dermo-epidermal junction appearance. In skin explants, it increases both dermis and dermo-epidermal junction dermis density (bottom tissue-type in explant photographs shown). A: Control (Serum only); panel B: 3-LED illumination (520 nm, 660 nm and 780 nm LEDs); Panel C: Combination of Serum application and 3-LED illumination. The 3-LED illumination provides protective effect on skin dermo-epidermal junction and skin tissue integrity. It protects skin explant from dermo-epidermal junction detachment and epidermis necrosis.
Figure 22:
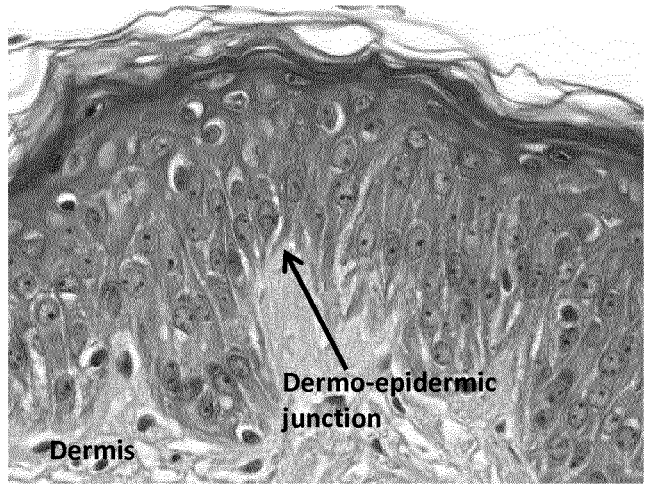
Figure 22:
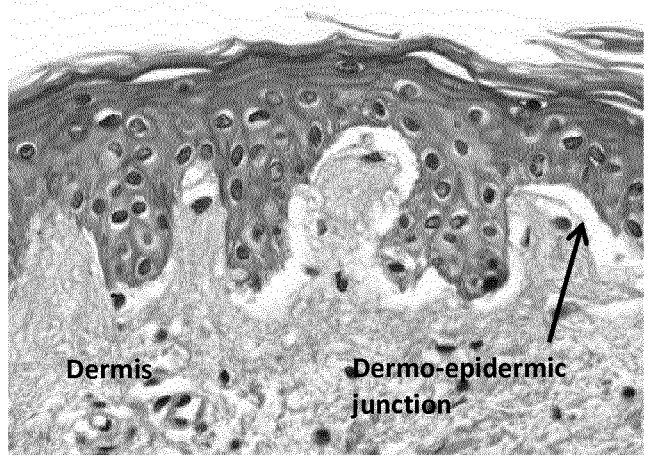

Finally, the effect on the dermis and on the dermo-epidermal junction appearance in the presence and absence of serum was determined (FIG. 22). Serum alone was not able to prevent dermo-epidermal junction detachment and epidermis necrosis in skin explants (Panel A). In contrast, 3-LED illumination (520 nm, 660 nm and 780 nm LEDs) provided a protective effect on both skin dermo-epidermal junction and skin tissue integrity (panel C).

Example 11: In Vivo Experiments

In a clinical study, female volunteers are treated split face with a combination of serum (e.g. InDerm AF4036) and the phototherapeutic device of the present invention, versus serum alone. Treatment is continued for 28 days, and a follow-up period of another 28 days is included without treatment. Facial skin wrinkles are measured using a DermaTop device (EoTech SA, Marcoussis, France) both during treatment and follow-up. Dermis density has been measured using a high frequency echograph Dermascan C® 2D Device both during treatment and follow-up. Measured parameters include average relief, relief amplitude and roughness are determined and skin dermis. A dramatic reduction of wrinkles on the facial side treated by the combination of serum and 3LED illumination according to the present invention is observed during treatment, and the effect is lasting even after treatment is stopped.

The invention claimed is:

1. A light-emitting device for illuminating the skin of a subject by phototherapy, the device consisting of one or more light sources adapted for emitting one or more beams of light having a discontinuous spectrum consisting of a combination of three peaks in wavelengths in the range of 510-536 nm, 650-670 nm and 768-792 nm.

2. The light-emitting device according to claim 1, wherein said one or more light sources are adapted for simultaneously or successively emitting said wavelength peaks in said one or more beams of light so as to illuminate the surface of the skin.

3. The light-emitting device according to claim 1, wherein said one or more light sources are adapted for emitting one or more beams of light having a discontinuous spectrum with peaks in wavelengths at 520 nm, 660 nm, and 780 nm and a half-band width between 15 and 35 nm.

4. The light-emitting device according to claim 1, wherein said one or more light sources are provided in the form of LEDs.

5. The light-emitting device according to claim 1, wherein said device
consists of a combination of at least three light-sources adapted for emitting one or more beams of light having a discontinuous spectrum with peaks in wavelengths in the range of 510-536 nm, 650-670 nm and 768-792 nm, the combination comprising a first LED set at emitting light in the range of 510-536 nm, a second LED set at emitting light in the range of 650-670 nm; and a third LED set at emitting light in the range of 768-792 nm.

6. The light-emitting device according to claim 1, wherein said device comprises a single light-source adapted for emitting a combination of peaks in wavelengths in the range of 510-536 nm, 650-670 nm and 768-792 nm simultaneously optionally by using a series of blocking filters to remove unwanted wavelength ranges, or by using a single light-source that is adapted for changing its emission spectrum between the required combination of three wavelength ranges subsequently.

7. A method for providing skin care by phototherapy consisting of illuminating the skin of a subject with light having a discontinuous spectrum consisting of a combination of three peaks in wavelengths in the range of 510-536 nm, 650-670 nm and 768-792 nm, wherein said skin is illuminated simultaneously or successively with said wavelengths.

8. The method according to claim 7, wherein said light has a discontinuous spectrum consisting of a combination of peaks in wavelengths at 520 nm, 660 nm, and 780 nm and a half-band width between 15 and 35 nm, wherein said light is provided by LED light sources.

9. The method according to claim 7, wherein the fluence or power (irradiance) provided to said skin by said illumination is sufficient to induce collagen and/or elastin production in said skin, and/or to induce activation, proliferation and/or cell migration of keratinocytes, fibroblasts, protomyofibroblast and/or myofibroblasts in said skin, when compared to a reference skin.

10. The method according to claim 7, wherein the skin care is a skin-related disorder selected from the group consisting of a disorder formed by acute skin wounds, skin ulcers, bedsores, diabetic skin sores, hypertrophic scars, keloid scars, telangiectasia (spider veins), skin atrophy, premalignant skin lesions, herpes, inflammatory acne, acne vulgaris, comedonic or polymorphic acne, nodulocystic acne, acne conglobata, senile acne, secondary acne, ichthyoses, ichthyosiform conditions, Darier's disease, palmoplantar keratoderma, leukoplakia, leucoplakiform conditions, lichen, lichen planus, cutaneous, mucosal or ungual psoriases, psoriatic rheumatism, cutaneous atopy, eczema, dry skin, inflammation of the skin, inflammation of the skin after dermatology and or aesthetic procedure, inflammation of the skin due to radiotherapy exposure, sensitive skin, red flushes, solar skin erythema, actinic keratosis, actinic lentigo, solar lentigo, freckles, brown spot, melasma, radiodermitis, skin allergies and allergic or irritant contact dermatitis, atopic dermatitis, rosacea, and lupus erythematosus.

11. The method of claim 7 wherein the skin care is cosmetic and provides to said subject skin rejuvenation, moisturization and/or tightening of skin, firming, filling, shaping and lifting skin, improving eye contour, skin radiance boost; and/or results in prevention and/or reduction of wrinkles, fine lines, age spots, scars, stretch marks, cellulite, sallow skin, eye puffiness, eye dark circles, hyperpigmented skin, lax skin, skin redness, leathery skin, or baldness.

* * * * *